United States Patent [19]

Martin et al.

[11] Patent Number: 4,933,336

[45] Date of Patent: Jun. 12, 1990

[54] THIADIAZINONE, OXADIAZINONE AND TRIAZINONE DERIVATIVES, AND THEIR USE FOR TREATING ACUTE OR CHRONIC HEART DISEASE

[75] Inventors: Michel Martin; Guy Nadler; Richard Zimmermann, all of Saint Gregoire, France

[73] Assignee: Laboratoires Sobio S.A., France

[21] Appl. No.: 230,314

[22] Filed: Aug. 9, 1988

[30] Foreign Application Priority Data

Aug. 11, 1987 [GB] United Kingdom ............... 8718957
May 12, 1988 [GB] United Kingdom ............... 8811276

[51] Int. Cl.⁵ ..................... A61K 31/38; A61K 31/53; C07D 285/16; C07D 273/04
[52] U.S. Cl. ............... 514/222.5; 514/229.2; 514/242; 544/8; 544/66; 544/68; 544/182; 546/18; 546/155; 546/158; 548/409; 548/410; 548/411; 548/485; 548/486
[58] Field of Search ............ 544/8, 66, 68, 182; 514/222.5, 229.2, 242

[56] References Cited

U.S. PATENT DOCUMENTS 4,771,048 9/1988 Muller et al. .................. 544/8

Primary Examiner—Mary C. Lee
Assistant Examiner—J. Richter
Attorney, Agent, or Firm—Jacobs & Jacobs

[57] ABSTRACT

A compound of formula (I), or a pharmaceutically acceptable salt thereof,

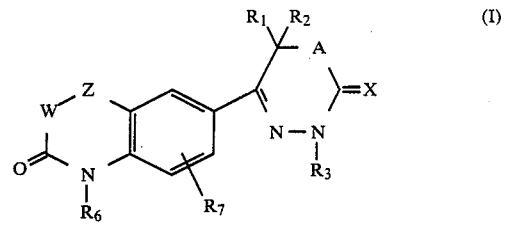

in which,
 $R_1$ is hydrogen, lower alkyl or $CH_2OR_6$;
 $R_2$ is hydrogen or lower alkyl;
 $R_3$ is hydrogen or lower alkyl;
 each of W and Z, which are different, represents —$CR_4R_5$— or —$(CR_xR_y)_n$—, in which,
 $R_4$ is hydrogen, $C_{1-3}$ alkyl, $C_{1-3}$ alkylthio or $C_{1-3}$ alkoxy;
 $R_5$ is $C_{1-3}$ alkyl, $C_{1-3}$ alkylthio or $C_{1-3}$ alkoxy; or together $R_4$ and $R_5$ form a 3 to 6 membered carbocyclic ring, or a heterocyclic ring containing one or two ring oxygen, nitrogen or sulphur atoms;
 or $R_4$ and $R_5$ together form an oxo or methylene group;
 each of $R_x$ and $R_y$ is hydrogen or $C_{1-3}$ alkyl; n is zero or 1;
 $R_6$ is hydrogen, lower alkyl, lower alkylcarbonyl, arylcarbonyl, aralkylcarbonyl, heteroarylcarbonyl, optionally substituted aminocarbonyl, lower alkoxycarbonyl and aryloxycarbonyl;
 $R_7$ is hydrogen or lower alkyl;
 X is oxygen or sulphur;
 and A is sulphur, oxygen or —NH—, is useful for the treatment of heart disease.

24 Claims, No Drawings

THIADIAZINONE, OXADIAZINONE AND TRIAZINONE DERIVATIVES, AND THEIR USE FOR TREATING ACUTE OR CHRONIC HEART DISEASE

This invention relates to compounds having pharmacological activity, pharmaceutical compositions containing them, processes for their preparation, and their use as active therapeutic agents, particularly in the treatment of acute or chronic heart disease.

EP-A-No. 0052442 discloses phenyl-thiadiazinone, oxadiazinone or triazinone derivatives which are phosphodiesterase inhibitors and are said to possess cardiotonic properties. There is no disclosure in this document of the derivatives having the property of increasing the sensitivity of myocardial contractile proteins to calcium, which is believed to be an additional, useful mechanism of action for cardiotonic agents.

It has now been discovered that certain novel phenyl-thiadiazinone, oxadiazinone and triazinone derivatives in which the phenyl nucleus forms part of a substituted 2-oxo-2,3-dihydroindole or 2-oxo-2,3,-dihydroquinone ring are phosphodiesterase inhibitors, and some of these derivatives may also increase the sensitivity of myocardial contractile proteins to calcium. The novel derivatives are therefore potentially valuable drugs in the treatment of congestive heart failure.

It has also been discovered that some of the derivatives have bronchodilator activity and are therefore of potential utility in the treatment of asthmatic conditions.

According to the present invention there is provided a compound of formula (I), or a pharmaceutically acceptable salt thereof:

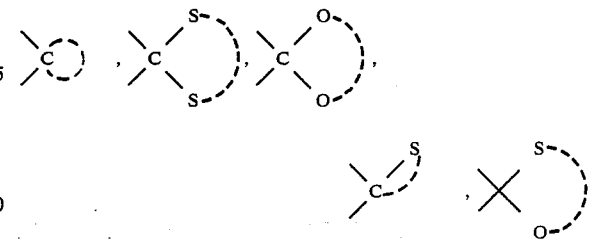

in which, $R_1$ is hydrogen, lower alkyl or $CH_2OR_6$;
$R_2$ is hydrogen or lower alkyl;
$R_3$ is hydrogen or lower alkyl;
each of W and Z, which are different, represents
—$CR_4R_5$— or —$(CR_xR_y)_n$—, in which,
$R_4$ is hydrogen, $C_{1-3}$ alkyl, $C_{1-3}$ alkylthio or $C_{1-3}$ alkoxy;
$R_5$ is $C_{1-3}$ alkyl, $C_{1-3}$ alkylthio or $C_{1-3}$ alkoxy;
or together $R_4$ and $R_5$ form a 3 to 6 membered carbocyclic ring, or a heterocyclic ring containing one or two ring oxygen, nitrogen or sulphur atoms,
or $R_4$ and $R_5$ together form an oxo or methylene group;
each of $R_x$ and $R_y$ is hydrogen or $C_{1-3}$ alkyl; n is zero or 1;
$R_6$ is hydrogen, lower alkyl, lower alkylcarbonyl, arylcarbonyl, aralkylcarbonyl, heteroarylcarbonyl, optionally substituted aminocarbonyl, lower alkoxycarbonyl and aryloxycarbonyl;
$R_7$ is hydrogen or lower alkyl;
X is oxygen or sulphur;
and A is sulphur, oxygen or —NH—.

Preferably, n is zero and/or X is oxygen and/or A is sulphur.

When $R_4$ and $R_5$ form a carbocyclic or heterocyclic ring, the ring may be saturated or unsaturated and substituted or unsubstituted. When the heterocyclic ring is substituted, suitable substituents include one or more oxo groups.

Examples of such rings are:

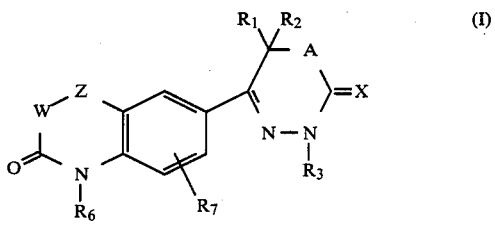

in which the dotted lines represent an alkylene linkage.

The terms 'lower alkyl' and 'lower alkoxy' are used herein to mean straight or branched chain alkyl and alkoxy groups having up to 6, preferably up to 4, carbon atoms.

The term 'aryl' is used herein to include carbocyclic aromatic groups, preferably having single or fused rings with 6 to 12 ring carbon atoms. Examples are phenyl and substituted phenyl.

The term 'aralkyl' is used herein to include carbocyclic aromatic groups linked to an alkylene group which suitably contains from 1 to 6 carbon atoms. The alkylene group may itself be optionally substituted by, for example, a further aryl group. Examples are benzyl and substituted benzyl.

The term 'heteroaryl' is used herein to include single or fused ring systems having 5 to 12 ring atoms, and comprising up to four hetero-atoms in the or each ring selected from oxygen, nitrogen and sulphur. An example of heteroaryl is pyridyl.

Preferred $R_1$ to $R_7$ substituents may be listed as follows:

$R_1$ is hydrogen or methyl;
$R_2$ is hydrogen or methyl;
$R_3$ is hydrogen or methyl;
$R_4$ is hydrogen, methyl, methylthio, hydroxy, methoxy or ethoxy;
$R_5$ is methyl, methylthio, methoxy or ethoxy; or
$R_4$ and $R_5$ together are oxo, ethylenedithio, propylenedithio, propylenethio, cyclopropyl, cyclopentyl, cyclohexyl, or imidazolidine-dione. $R_6$ is hydrogen, methyl, acetyl, aminocarbonyl, benzoyl, p-nitrobenzoyl, p-aminobenzoyl, 3,4-dimethoxybenzoyl, pyridylcarbonyl, benzylcarbonyl, ethoxycarbonyl, phenyloxycarbonyl or 2,4-dioxo-1,3-diphenyl butyl; and $R_7$ is hydrogen or methyl.

Preferably, when n is 1, each of $R_x$ and $R_y$ is hydrogen.

Particular compounds of the invention are:
1,3-dihydro-5-(3,6-dihydro-2-oxo-2H-1,3,4-thiadiazin-5-yl)-3-methyl-3-methylthio-2H-indol-2-one;
1,3-dihydro-5-(3,6-dihydro-2-oxo-2H-1,3,4-thiadiazin-5-yl)-3,3-dimethyl-2H-indol-2-one;
1,3-dihydro-5-(3,6-dihydro-6-methyl-2-oxo-2H-1,3,4-thiadiazin-5-yl)-3,3-dimethyl-2H-indol-2-one;

1,3-dihydro-5-(3,6-dihydro-2-oxo-2H-1,3,4-thiadiazin-5-yl)-3-methyl-2H-indol-2-one;

1,3-dihydro-5-(3,6-dihydro-6-methyl-2-oxo-2H-1,3,4-thiadiazin-5-yl)-3-methyl-3-methylthio-2H-indol-2-one;

5'-(3,6-dihydro-6-methyl-2-oxo-2H-1,3,4-thiadiazin-5-yl)-spiro[cyclopentane-1,3'-[3H]-indol]- 2'(1'H)one;

1-acetyl-1,3-dihydro-5-(3,6-dihydro-6-methyl-2-oxo-2H-1,3,4-thiadiazin-5-yl)-3,3-dimethyl-2H-indol-2-one;

1-Acetyl-1,3-dihydro-5-(3,6-dihydro-2-oxo-2H-1,3,4-thiadiazin-5-yl)-3-methyl-2H-indol-2-one 1-Acetyl-1,3-dihydro-5-(3,6-dihydro-2-oxo-2H-1,3,4-thiadiazin-5-yl)-3-methyl-3-methylthio-2H-indol-2-one 1,3-Dihydro-5-(3,6-dihydro-6-methyl-2-oxo-2H-1,3,4-thiadiazin-5-yl)-3-methylthio-2H-indol-2-one 1,3-Dihydro-5-(3,6-dihydro-2-oxo-2H-1,3,4-thiadiazin-5-yl)-3-methylthio-2H-indol-2-one 5-(3,6-Dihydro-6-methyl-2-oxo-2H-1,3,4-thiadiazin-5-yl)1H-indole-2,3-dione 5'-(3,6-Dihydro-6-methyl-2-oxo-2H-1,3,4 thiadiazin-5-yl)-spiro[1,3-dithiolane-2,3'-[3H]indol]-2(1'H)-one 5'-(3,6-Dihydro-6-methyl -2-2-oxo-2H-1,3,4-thiadiazin-5-yl)-spiro[1,3-dithiane-2,3'-[3H]indol-2'(1'H)-one 1,3-Dihydro-5-(3,6-dihydro-6-methyl-2-oxo-2H-1,3,4-thiadiazin-5-yl)-3,3-di(methylthio)-2H-indol-2-one 5-(3,6-Dihydro-6-methyl-2-oxo-2H-1,3,4-thiadiazin-5-yl)-spiro[cyclopropane-1,3'-[3H]indol]-2'-(1'H)-one 5'-(3,6-Dihydro-6-methyl-2-oxo-2H-1,3,4-thiadiazin-5-yl)-spiro[cyclohexane-1,3'-[3H]indol]-2'-(1'H)-one 1,3-Dihydro-5-(3,6-dihydro-6-methyl-2-oxo-2H-1,3,4-thiadiazin-5-yl)-1,3,3-trimethyl-2H-indol-2-one 5'-(3,6-dihydro-3,6-dimethyl-2-oxo-2H-1,3,4-thiadiazin-5-yl)-1'-methyl-spiro[cyclopentane-1,3'-[3H]indol]-2'(1'H)-one 5'-(3,6-Dihydro-2-oxo-2H-1,3,4-thiadiazin-5-yl)-spiro[thiolane-2,3'-[3H]-indol]-2'(1'H)-one 5'-(3,6-Dihydro-6-methyl-2-oxo-2H-1,3,4-thiadiazin-5-yl)-spiro[thiolane-2,3'-[3H]-indol]-2'(1'H)-one 1-Benzoyl-1,3-dihydro-5-(3,6-dihydro-6-methyl-2-oxo-2H-1,3,4-thiadiazin-5-yl)-3,3-dimethyl-2H-indol-2-one 1,3-Dihydro-5-(3,6-dihydro-6-methyl-2-oxo-2H-1,3,4-thiadiazin-5-yl)-3,3-dimethyl-1-[(4-pyridyl)carbonyl-2H-indol]-2-one 1,3-Dihydro-5-(3,6-dihydro-6-methyl-2-oxo-2H-1,3,4-thiadiazin-5-yl)-3,3-dimethyl-1-[(3-pyridyl)carbonyl]-2H-indol-2-one 1,3-Dihydro-5-(3,6-dihydro-6-methyl-2-oxo-2H-1,3,4-thiadiazin-5-yl)-3,3-dimethyl-1-(4-nitrobenzoyl)-2H-indol-2-one 1,3-Dihydro-5-(3,6-dihydro-6-methyl-2-oxo-2H-1,3,4-thiadiazin-5-yl)-3,3-dimethyl-1-(phenylmethylcarbonyl)-2H-indol-2-one 5'-(3,6-Dihydro-6-methyl-2-oxo-2H-1,3,4-thiadiazin-5-yl-1'-[(4-pyridyl)carbonyl]-spiro[cyclopentane-1,3'-[3H]indol]-2'(1'H)-one 1-[2,3-Dihydro-5-(3,6-dihydro-6-methyl-2-oxo-2H-1,3,4-thiadiazin-5-yl)-3,3-dimethyl-2-oxo-1H-indol-1-yl]-2,4-diphenyl-1,3-butanedione 1,3-Dihydro-5-(3,6-dihydro-6-methyl-2-oxo-2H-1,3,4-thiadiazin-5-yl)-3,3,4-trimethyl-2H-indol-2-one 1,3-Dihydro-5-(3,6-dihydro-6-methyl-2-oxo-2H-1,3,4-thiadiazin-5-yl)-3,3,6-trimethyl-2H-indol-2-one 1,3-Dihydro-5-(3,6-dihydro-6-methyl-2-oxo-2H-1,3,4-thiadiazin-5-yl)-3,3,7-trimethyl-2H-indol-2-one 1,3-Dihydro-5-(3,6-dihydro-6,6-dimethyl-2-oxo-2H-1,3,4-thiadiazin-5-yl)-3,3-dimethyl-2H-indol-2-one 1,3-Dihydro-5-(3,6-dihydro-6-methyl-2-oxo-2H-1,3,4-thiadiazin-5-yl)-3-hydroxy-3-methyl-2H-indol-2-one Ethyl 2,3-dihydro-5-(3,6-dihydro-6-methyl-2-oxo-2H-1,3,4-thiadiazin-5-yl)-3,3-dimethyl-2-oxo-1H-indol-1carboxylate 1,3-Dihydro-5-(1,2,3,6-tetrahydro-6-methyl-2-oxo-1,3,4-triazin-5-yl)-3,3-dimethyl-2H-indol-2-one 1,3-Dihydro-5-(3,6-dihydro-6-methyl-2-oxo-2H-1,3,4-oxadiazin-5-yl)-3,3-dimethyl-2H-indol-2-one 1,3-Dihydro-5-(3,6-dihydro-6-methyl-2-oxo-2H-1,3,4-thiadiazin-5-yl)-1-(3,4-dimethoxybenzoyl)-3,3-dimethyl-2H-indol-2-one Phenyl 2,3-dihydro-5-(3,6-dihydro-6-methyl-2-oxo-2H-1,3,4-thiadiazin-5-yl)-3,3-dimethyl-2-oxo-1H-indole-1-carboxylate 3,4-Dihydro-6-(3,6-dihydro-6-methyl-2-oxo-2H-1,3,4-thiadiazin-5-yl)-4,4-dimethyl-2(1H)-quinolinone 3,4-Dihydro-6-(3,6-dihydro-6-methyl-2-oxo-2H-1,3,4-thiadiazin-5-yl)-3,3-dimethyl-2(1H)-quinolinone 5'-(3,6-Dihydro-6-methyl-2-oxo-2H-1,3,4-thiadiazin-5-yl)-1'[(4-nitrophenyl)carbonyl]-spiro[cyclopentane-1,3'-[3H]indol]-2'(1'H)-one 1,3-Dihydro-5-(3,6-dihydro-6-methyl-2-oxo-2H-1,3,4-thiadiazin-5-yl)-3,3-dimethyl-1-[4-aminophenyl]carbonyl-2H-indol-2-one 2,3-Dihydro-5-(3,6-Dihydro-6-methyl-2-oxo-2H-1,3,4-thiadiazin-5-yl)-3,3-dimethyl-2-oxo-1H-indol-1-carboxamide Ethyl 1,2,3,4-tetrahydro-6-(3,6-dihydro-6-methyl-2-oxo-2H-1,3,4-thiadiazin-5-yl)-4,4-dimethyl-2-oxo-1-quinoline carboxylate 5'-(3,6-Dihydro-6-methyl-2-oxo-2H-1,3,4-thiadiazin-5-yl)-spiro[imidazolidine-4,3'-[3H]indole]-2,2'(1'H),5-trione The compounds of the invention have two potential chiral centres at the $R_4/R_5$ and $R_1/R_2$ substituted positions, and can therefore exist in more than one stereoisomeric form. The invention extends to all such forms and to mixtures thereof, including all enantiomers, diastereomers, and racemates.

The pharmaceutically acceptable salts of the compounds of formula (I), (when the compound contains a salifiable group) include acid addition salts with conventional acids such as hydrochloric, hydrobromic, boric, phosphoric, sulphuric and pharmaceutically acceptable organic acids such as acetic, tartaric, maleic, citric, succinic, benzoic, ascorbic, methanesulphonic, α-keto-glutaric, α-glycerophosphoric, and glucose-1-phosphoric acids. Preferably the acid addition salt is a hydrochloride.

The compounds of the formula (I) and their pharmaceutically acceptable salts may also form solvates with pharmaceutically acceptable solvents, and such solvates are included within the expression 'a compound of formula (I)' used herein.

Salts of the compounds of the formula (I) which are not pharmaceutically acceptable may be useful as intermediates in the preparation of pharmaceutically acceptable salts of compounds of the formula (I) or the compounds of the formula (I) themselves, and as such form an aspect of the present invention.

The compounds of formula (I) in which A is sulphur may be prepared by treating a compound of formula (II)

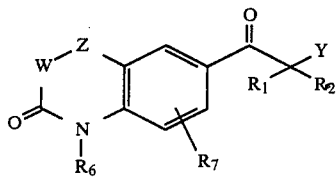
(II)

in which $R_1$, $R_2$, $R_6$, $R_7$, W and Z are as defined in formula (I), and Y is a leaving group, with a compound of formula (III)

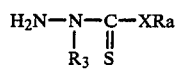
(III)

in which $R_3$ and X are as defined in formula (I), and $R_a$ is an alkyl group, preferably $C_{1-6}$ alkyl, for example methyl or ethyl, or an ammonium or alkali metal ion, and thereafter optionally converting a compound wherein X is oxygen to a compound wherein X is sulphur by, for example, treatment with Lawessons reagent, and thereafter if desired converting a compound of formula (I) thereby produced to a pharmaceutically acceptable salt thereof or to a further compound of formula I.

Y is preferably a halogen atom, an alkanesulphonyloxy group (such as methylsulphonyloxy) or arylsulphonyloxy (such as benzenesulphonyloxy or p-toluenesulphonyloxy).

The reaction is preferably carried out in an organic solvent, for example ethanol, acetonitrile or dimethylformamide, at between room temperature and the boiling point of the solvent.

The compounds of formula (I) in which A is oxygen may be prepared by cyclising a compound of formula (IV):

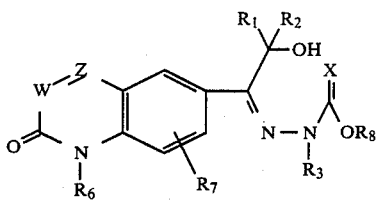
(IV)

in which $R_1$, $R_2$, $R_6$, $R_7$, X, W and Z are as defined in formula (I), and $R_8$ is an alkyl group, preferably $C_{1-6}$ alkyl such as methyl or ethyl. The cyclisation may be carried out in the presence of a base, such as sodium ethoxide, in a diluent or solvent, such as ethanol, at about ambient temperature.

The compounds of formula (I) in which A is —NH— may be prepared by treating a compound of formula (V):

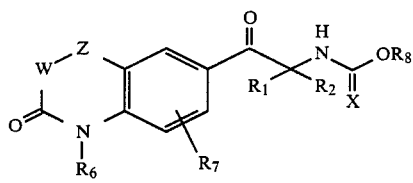
(V)

in which $R_1$, $R_2$, $R_6$, $R_7$, X, W and Z are as defined in formula (I) and $R_8$ is as defined in formula (IV), with a compound of formula (VI):

(VI)

in which $R_3$ is as defined in formula (I).

The reaction may be carried out in a diluent or solvent, such as ethanol, and suitably at a temperature up to the boiling point of the diluent or solvent.

The compounds of formula (I) may be converted into pharmaceutically acceptable salts in conventional manner by, for example, treatment with an appropriate acid.

Compounds of formula (I) may be converted to other compounds of formula (I) in accordance with known methods.

For example, compounds of formula (I) in which $R_6$ is lower alkylcarbonyl, arylcarbonyl, aralkylcarbonyl, heteroarylcarbonyl, lower alkoxycarbonyl or aryloxycarbonyl may be prepared by treating the corresponding compound of formula (I) in which $R_6$ is hydrogen, with an acid chloride of formula $R_6$-Hal, where Hal is halogen, preferably chlorine.

Also, compounds of formula (I) in which $R_4$ and $R_5$ together form a heterocyclic ring containing two sulphur atoms may be prepared by treating the corresponding compound of formula (I) in which $R_4$ and $R_5$ together form an oxo group, with an alkanedithiol.

The compounds of formula (II) may themselves be prepared by treating a compound of formula (VII):

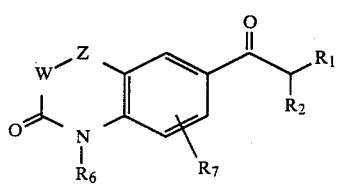
(VII)

in which $R_1$, $R_2$, $R_6$, $R_7$, W and Z are as defined in formula (I), with a compound containing the leaving group Y or, when Y is halogen, with the halogen itself.

When Y is halogen, it is preferably bromine or chlorine.

The compounds of formula (VII) may be prepared in several ways, as summarised in the following Schemes A, B and C.

Scheme A

This Scheme may be used for preparing compounds of formula (VII) in which $R_4$ or $R_5$ is $C_{1-3}$ alkylthio and n is zero, and is exemplified by $R_4$ as methyl, and $R_5$ as methylthio.

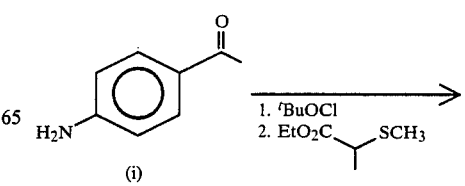
(i)

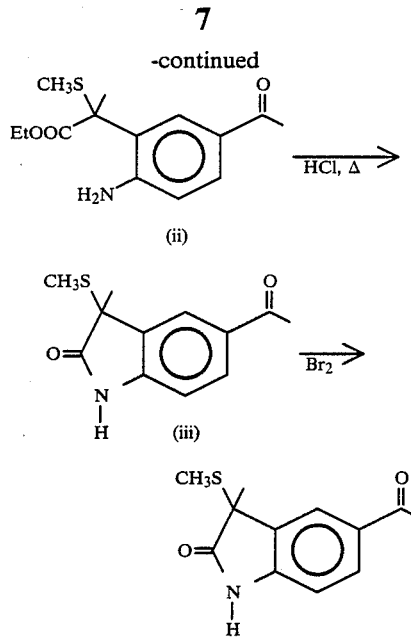

A reaction of this type is described in J. Am. Chem. Soc., 96, 5508, 1974 (Gassman and Bergen).

Scheme B

This scheme is suitable for preparing compounds in which one or both of R₄ and R₅ are C₁₋₃ alkyl, or R₄ and R₅ together form a ring as defined in formula (II), and n is zero, and is exemplified by R₄ and R₅ as methyl.

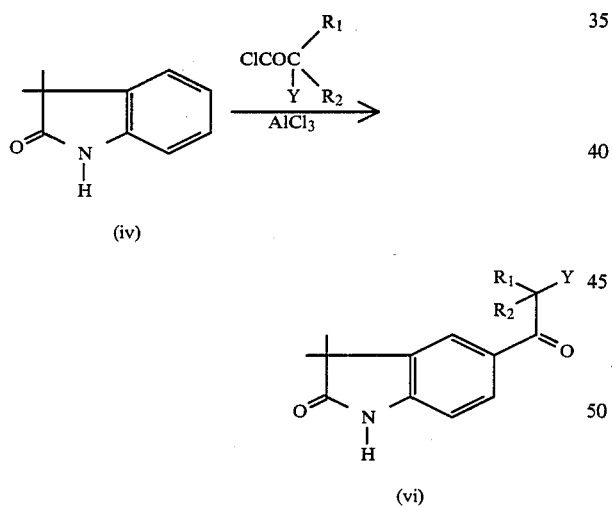

Scheme C

This is a variant of Scheme B, in which an additional step is present

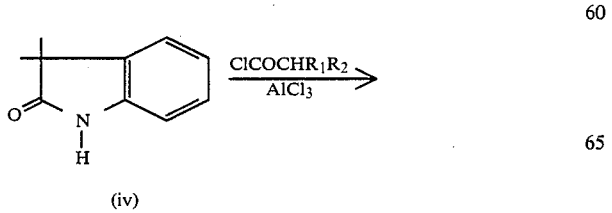

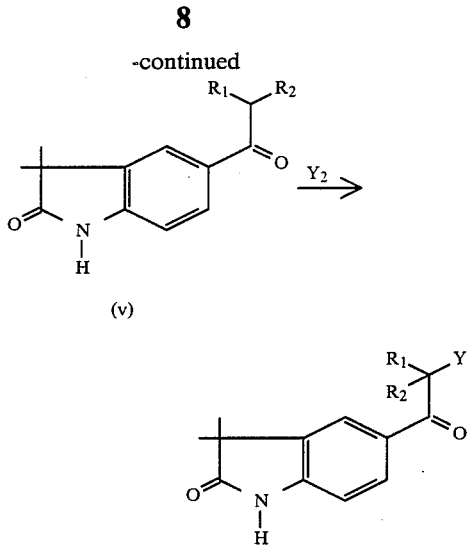

In the above schemes, the starting compounds of formulae (i) and (iv) are known compounds; compound (iv) is disclosed in Monatsh., 58, 369–398, 1931 and spiro analogues thereof (when R₄ and R₅ form a ring) are described in Beilstein 21 II 269–268.

The compounds of formulae (III) are also known compounds, or are preparable in analogous manner to the known compounds of formula (III).

Compounds of formula (IV) may be prepared by treating a compound of formula (VIII):

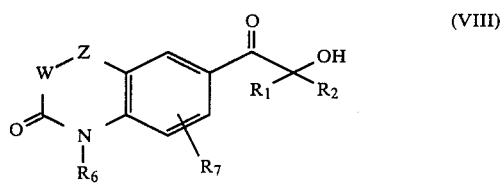

in which R₁, R₂, R₆, R₇, W and Z are as defined in formula (I), with an alkyl carbazate of formula (IX):

in which X, R₃ and R₈ are as defined in formula (IV).

Compounds of formula (VIII) may themselves be prepared by hydrolysing a compound of formula (II).

Compounds of formula (V) may be prepared by treating a compound of formula (X):

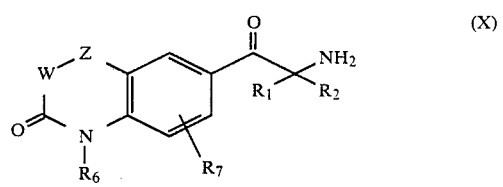

in which R₁, R₂, R₆, R₇, W and Z are as defined in formula (I), with a compound of formula (XI):

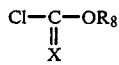

in which X and $R_8$ are as defined in formula (IV).

Compounds of formula (X) may themselves be prepared by treating a compound of formula (II) with sodium azide, and reducing the thus formed azide with hydrogen in the presence of a palladium/charcoal catalyst.

Compounds of formula (VI), (IX) and (XI) are known compounds, or can be prepared from known compounds by known methods.

A number of the intermediate compounds of formulae (II), (IV), (V), (VII), (VIII) and (X) are novel and form a further aspect of the invention.

In order to utilise the potential cardiotonic and antiasthmatic activities of the compounds of formula (I) the invention also provides a pharmaceutical composition comprising a compound of formula (I), or a pharmaceutically acceptable salt thereof, and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate.

Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved.

Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

In addition such compositions may contain further active agents such as vasodilator agents and diuretics.

As is common practice, the compositions will usually be accompanied by written or printed directions for use in the medical treatment concerned.

The invention further provides a method of treatment or prophylaxis of heart disease or asthmatic conditions in mammals, such as humans, which comprises the administration of an effective amount of a compound of formula (I), or a pharmaceutically acceptable salt thereof, to the sufferer.

An amount effective to treat the disorders hereinbefore described depends on the relative efficacies of the compounds of the formula (I), the nature and severity of the disorders being treated and the weight of the mammal. However, a unit dose will normally contain 1 to 100 mg for example 2 to 50 mg, of the compound of the invention. Unit doses will normally be administered once or more than once a day, for example 2,3,4,5 or 6 times a day, more usually 2 to 4 times a day, such that the total daily dose is normally in the range, for a 70 kg adult of 1.0 to 2500 mg, more usually 50 to 2000 mg, for example 10 to 75mg, that is in the range of approximately 0.002 to 35 mg/kg/day, more usually 1 to 30 mg/kg/day, for example 0.15 to 1 mg/kg/day.

In an additional aspect of the invention there is provided a compound of formula (I) or a pharmaceutically acceptable salt thereof, for use as an active therapeutic substance, and in particular for the treatment of heart disease or asthmatic conditions.

Furthermore, the invention provides the use of a compound of formula (I) or a pharmaceutically acceptable salt thereof in the manufacture of a medicament for the treatment of heart disease or asthmatic conditions.

The following examples illustrate the compounds of the invention and the following descriptions illustrate intermediates thereto. The following pharmacological data illustrate the activity of the compounds of the invention.

DESCRIPTION 1

Ethyl 2-[(3-acetyl-6-amino)phenyl]-2-methylthiopropionate

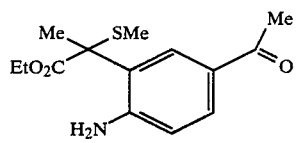
(D1)

To a stirred solution of 11.9 g 1-(4-aminophenyl) ethanone in 300ml methylene chloride at −65° C. was added dropwise a solution of 9.55 g of t-butyl hypochlorite in 40 ml dichloromethane. After 10 min., 13 g of ethyl methylthioacetate (A. Schoenberg, K. Pfaecke, Chem. Ber. 1966, 99, 2321) dissolved in 30 ml methylene chloride were added in 45 min. and stirring at −65° C. was continued for 1 h. Subsequently, 8.8 g of triethylamine in 40 ml methylene chloride were added. After addition was completed, the cooling bath was removed and the solution was allowed to warm to room temperature. A 100 ml portion of water was added and the organic layer was separated and washed with another 100 ml portion of water. The organic layer was treated with charcoal, dried over MgSO$_4$ and evaporated to dryness. 7 g of ethyl 2-[(3-acetyl-6-amino)phenyl]-2-methylthiopropionate, m.p. 114° C. was isolated after trituration with ether and standing 48 h. at 0° C. The ether solution afforded another 4.0 g crop.

IR (KBr) ν: 3,400; 3,310; 3,200; 1,720; 1,650; 1,640; 1,270; 1,240 cm$^{-1}$.

DESCRIPTION 2

5-Acetyl-1,3-dihydro-3-methyl-3-methylthio-2H-indol-2-one

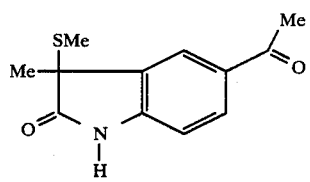
(D2)

7 g of ethyl 2-[(3-acetyl-6-amino)phenyl]-2-methylthiopropionate and 40 ml of a 2N solution of HCl were stirred for 2 hrs. at room temperature. Filtration and washing with water yielded 5.2 g of 5-acetyl-1,3-dihydro-3-methyl-3-thiomethy-2H-indol-2-one.

m.p. = 165° C.

IR (KBr) ν: 3,250; 1,735; 1,695; 1,670; 1,615; 1,355; 1,280; 1,190; 1,125 cm$^{-1}$.

NMR (DMSO-d$_6$): δ=1.55 (s,3H,C$\underline{H}_3$); 1.90 (s,3H,C$\underline{H}_3$S); 2.50 (s,3H,C$\underline{H}_3$CO); 7.00 (d,1H,J=8 Hz,Ar); 8.1 (d,1H,J=8 Hz,Ar); 8.00 (s,1H,Ar); 10.90 (s,1H,exch.D$_2$O,N$\underline{H}$).

DESCRIPTION 3

5-(2-Bromoacetyl)-1,3-dihydro-3-methyl-3-methylthio-2H-indol-2-one

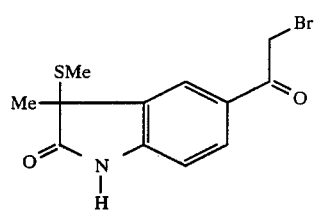
(D3)

1.17 g 5-acetyl-1'3-dihydro-3-methyl-3-thiomethyl-2H-indol-2-one in 20 ml CHCl$_3$ were cooled to 0.5° C. Bromine (0.8 g) in 5 ml CHCl$_3$ was added dropwise. The solution was allowed to return to room temperature (15 min.) and washed with 2×50 ml water, 50 ml of a saturated solution of NaHCO$_3$ and 50 ml of brine. The organic layer was dried over MgSO$_4$ and evaporated to dryness. Trituration with ethyl ether afforded 1.0 g of compound used directly in the next reaction.

DESCRIPTION 4

5-(2-Chloroacetyl)-1,3-dihydro-3,3-dimethyl-2H-indol-2-one

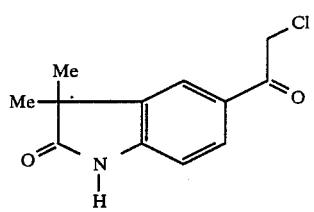
(D4)

13.3 g aluminium chloride and 2.2 ml DMF were mixed and heated with stirring, at 70° C. during 15 min. After cooling to 40° C., 1.5 g 1,3-dihydro-3,3-dimethyl-2H-indol-2-one and 1.1 g 2-chloroacetyl chloride were added and stirred at 70° C. for 45 min. The mixture was poured onto 50 g ice and 10 ml 10N HCl and extracted with 3×75 ml ethyl acetate.

The organic layer was washed with 2×100 ml water, dried over MgSO$_4$ and evaporated to dryness. Trituration with ether afforded 1.6 g of compound used directly in the next step.

DESCRIPTION 5

5-[(2-Chloro-1-oxo)propyl]-1,3-dihydro-3,3-dimethyl-2H-indol-2-one

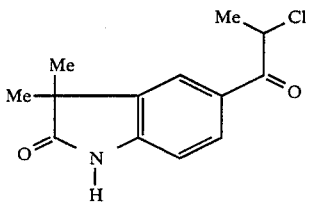
(D5)

13.3 g aluminium chloride and 2.2 ml DMF were mixed and heated with stirring at 70° C. during 15 min. After cooling to 40° C., 1.5 g 1,3-dihydro-3,3-dimethyl-2H-indol-2-one and 1.25 g 2-chloropropionyl chloride were added and stirred at 70° C. for 1 h. The mixture was poured onto 100 g ice and 10 ml 10N HCl, then extracted with 3×75 ml ethyl acetate.

The organic layer was washed with 2×100 ml water, dried over MgSO₄ and evaporated to dryness. Trituration with ether afforded 1.25 g of compound used directly in the next step.

DESCRIPTION 6

Methyl 1,3-dihydro-3-methyl-2-oxo-2H-indole-3-carboxylate

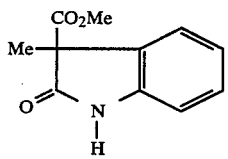
(D6)

5 g oxindole, 60 ml dimethyl carbonate and 2.32 g sodium methylate were refluxed for 18 hrs. under nitrogen. 50 ml methanol was added to dissolve the precipitate, followed by 8.73 g methyl iodide. Stirring overnight yielded a mixture which was concentrated, partitioned between water and dichloromethane, and extracted with dichloromethane. Treatment of the organic layer with charcoal, yielded, after removal of the solvent, 5.4 g of green crystals. This compound was purified by chromatography (silica; eluent=ether/hexane: 10/90 to 100/0) and washed with isopropyl ether to yield 3.48 g of pale yellow crystals,
m.p.=130° C.

IR (KBr) $\nu=3,250$; 1,750; 1,705; 1,610; 1,470; 1,390; 1,325; 1,235; 1,115 cm$^{-1}$.

NMR (DMSO-d₆) $\delta=1.50$ (s,3H,C$\underline{H}_3$; 3.60 (s,3H,OC$\underline{H}_3$); 6.8–7.3 (m,4H,Ar); 10.7 (s,1H,exch.-D₂O,N$\underline{H}$).

DESCRIPTION 7

5-(2-Chloroacetyl)-1,3-dihydro-3-methyl-2H-indol-2-one

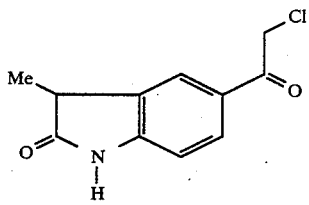
(D7)

1.70 ml DMF was added dropwise to 10.35 g crushed aluminium chloride. The mixture which became liquid was stirred for 15 min. at 70° C. and then cooled. 1.5 g of methyl 1,3-dihydro-3-methyl-2-oxo-2H-indol-3-carboxylate was added followed by 0.9 g chloroacetyl chloride. The mixture was heated to 70° C. for 18 hrs., then poured onto crushed ice (50 g) containing 7 ml 10N HCl. A yellow precipitate formed. Extraction with ethyl acetate, washing with water until neutral and drying over MgSO₄ sulphate gave compound pure enough for the next step.

Yield 1.15 g.

IR (KBr) $\nu=3,000$; 1,710; 1,690; 1,610 cm$^{-1}$.

NMR (0.5 CDCl₃+0.1 (DMSO-d₆) $\delta=1.42$ (d,J=9 Hz,3H, C$\underline{H}_3$); 3.40 (q,J=9 Hz 1H,C$\underline{H}$); 4.85 (s,2H,C$\underline{H}_2$Cl); 6.9 (d,1H,Ar); 7.85 (m,2H,Ar); 10.60 (s,1H,exch.D₂O,N$\underline{H}$).

DESCRIPTION 8

1-Acetyl-5-[(2-chloro-1-oxo)propyl]-1,3-dihydro-3,3-dimethyl-2H-indol-2-one

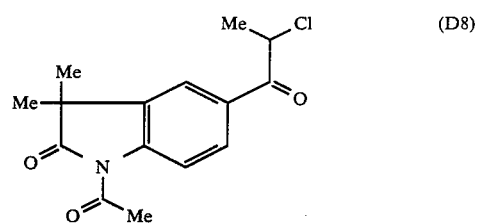
(D8)

2 g of 5-[(2-chloro-1-oxo)propyl]-1,3-dihydro-3,3-dimethyl-2H-indol-2-one (compound of Description 5) was dissolved in 40 ml acetic anhydride and refluxed for 5 hrs.

The excess anhydride was evaporated under vacuum. The residual oil was triturated with ether yielding 2 g of compound, used directly in the next step.
m.p.=130° C.

DESCRIPTION 9

5-[(2-Bromo-1-oxo) ethyl-1,3-dihydro-3-methyl-2H-indol-2-one

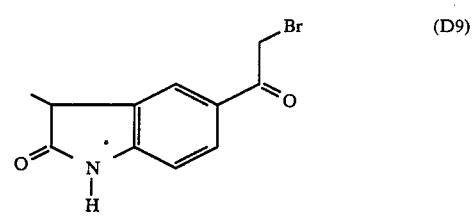
(D9)

Starting from 1,3-dihydro-3-methyl-2H-indol-2-one (Monat. Chem.,18,533,1897), and following the procedure of Description 4. but using 2-bromoacetyl chloride, afforded, the desired compound after trituration of the residue in isopropyl ether. This compound was directly used in the next step.

IR (KBr) $\nu=3,200$: 1,715; 1,685; 1,615; 1,225; 1,135 cm$^{-1}$.

NMR (DMSO-d₆) $\delta=1.37$ ppm (d,3H,J=7.6 Hz,C$\underline{H}_3$); 5.53 (q,1H,J=7.6 Hz,C$\underline{H}$); 4.84 (s,2H,C$\underline{H}_2$); 6.95 (d.1H,J=8.7 Hz,Ar); 7.93 (m, 2H,Ar); 10.84 (s,1H,exch.D₂O,N$\underline{H}$).

DESCRIPTION 10

1-Acetyl-5-[(2-bromo-1-oxo)ethyl]-1,3-dihydro-3-methyl-2H-indol-2-one

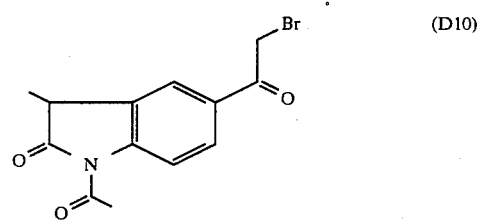
(D10)

2 g (7.4mmol) 5-[(2-bromo-1-oxo) ethyl]-1,3-dihydro-3-methyl-2H-indol-2-one (Description 9) and 20 ml acetic anhydride are heated at reflux for 2 hrs. The excess of reagent is distilled off under vacuum. The residue is dissolved in water and extracted twice with 50 ml of ethyl acetate. The organic phase is washed twice with 100 ml of water, dried over MgSO4 and evapored to dryness leaving 0.8 g (yield 35%), of a compound used directly in the next step.

IR (KBr) ν=1,765; 1,700; 1,680; 1,610; 1,305; 1,280 cm$^{-1}$.

NMR (CDCl3) δ=1.60 ppm (d,3H,J=7.5 Hz,CH3); 2.71 (s,3H, CH3); 3.74 (q,1H,J=7.5 Hz,CH); 4.45 (s,2H,CH3); 7.95 (m,2H, Ar); 8.34 (m,1H,Ar).

DESCRIPTION 11

5[(2-Chloro-1-oxo)propyl]-1,3-dihydro-3-methylthio-2H-indol-2-one

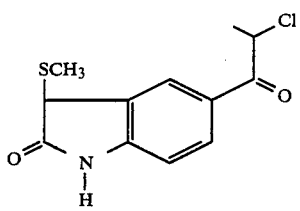

(D11)

A solution of 20 g (0.11 mol) 1-(4-aminophenyl)-2 chloro propanone (Kulkarni B.S. et al., J.Pharm.-Sci.,58,(7)852-7, 1969) in 290 ml methylene chloride was cooled to −65° C. 11.80 g (0.11 mol) t-butyl hypochlorite in 40 ml methylene chloride were added dropwise. Stirring is continued for 15 mn. A solution of 14.6 g (0.11 mol) ethyl methylthioacetate in 40 ml methylene chloride was then added dropwise at −65° C. Stirring is continued for 1.5 hrs at this temperature. 11 g triethylamine (0.11 mol) in 40 ml methylene chloride were then added and the reaction temperature slowly raised to ambiant. 100 ml of water were added and the reaction mixture extracted with methylene chloride. The organic layer was washed with water and concentrated. The oily residue was taken up in 100 ml ethyl ether and 50 ml 2N hydrochloric acid were added. Stirring overnight. Extraction of the aqueous layer with ethyl acetate. Washing with water. The organic layers were decolorized with charcoal and dried over magnesium sulfate. Elimination of the solvent afforded 16.0 g of an oil used in the next step without further purification. A small amount can be purified for analytical purpose by column chromatography (silica, eluent:Hexane/ethyl acetate:1/1)

Yield:64 %.

IR (film)ν=3,250; 1,700; 1,620; 1,495; 1,445; 1,235 cm$^{-1}$.

NMR (CDCl3)δ=1.75 ppm (d,3H,J=6.5Hz,CH3-CH); 2.08 (s,3H, CH3S); 4.35 (s,1H,exch.-D2O,CH3SCH); 5.22 (q,1H,J=6.5Hz, CHCH3); 7.03 (d,1H,J=8.7Hz,Ar); 8.05 (m,2H,Ar); 9.34 (m,1H, exch.-D2O,NH).

DESCRIPTION 12

5-[(2-Chloro-1-oxo)ethyl]-1,3 dihydro-3-methylthio-2H-indol -2-one

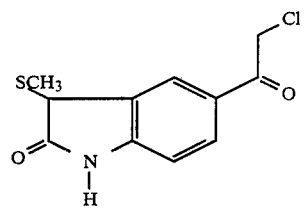

(D12)

Starting from 1-(4 aminophenyl)-2-chloro ethanone (Described in Beilstein 14,49,I,367) and ethyl methyl thioacetate and following the procedure of Description 11 afforded the desired compound.

Yield=50%.

m.p.=175° C.

IR (KBr)ν=3,250; 1,725; 1,685; 1,605; 1,487; 1,415; 1,230; 1,120 cm$^{-1}$.

NMR (DMSO-d6)δ=2.00 (s,3H,CH3S); 4.54 (s,1H,exch.D2O,SCH); 5.09 (s,2H,CHHD 2Cl); 6.98 (d,1H,J=8 Hz,Ar); 7.90 (m,2H,Ar); 10.94 (m,exch.-D2O, 1H,NH).

DESCRIPTION 13

5′-[(2-Chloro-1-oxo)ethyl]-spiro- thiolane-2,3′- 3H-indol 2(1′H)-one

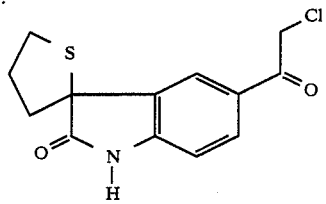

(D13)

Starting from 1-(4-aminophenyl)-2-chloroethanone (Described in Beilstein 14,49,I,367) and methyl 2-thiolane carboxylate (Ernst, Chem.Ber.,20,519,1887) and following the procedure of Description 11, afforded the desired compound, which was used crude in the next step.

Yield:12%.

NMR (CDCl3)δ=2.0-3.5 ppm (m,6H,SCH2CH2CH2); 4.65 (s,2H, CH2Cl):7.05 (d,J′=8 Hz,1H,Ar); 7.86 (dd,J=1.8 Hz,J′=8 Hz,1H, Ar); 7.99 (d,J=1.8 Hz,1H,Ar); 9.24 (s,1H,exch.D2O,NH).

DESCRIPTION 14

5′-[2-Chloro-1-oxo)propyl]-spiro- thiolane-2,3′- 3H -indol -2(1′H)-one

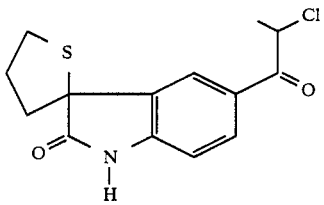

(D14)

Starting from 1-(4-aminophenyl)-2 chloropropanone and methyl 2-thiolane carboxylate (Ernst, Chem.-

Ber.,20,519,1887), and following the procedure of Description 11, afforded the desired compound.
Yield:57%.
m.p.: 129° C.
IR (KBr)ν=3,150; 1,735; 1,682; 1,615; 1,175 cm⁻¹.
NMR (CDCl₃)δ=1.75 ppm (d,J=7Hz,3H,CH₃CH); 2.2-2.7 (m,4H, SCH₂CH₂CH₂S—); 3.2-3.5 (m,2H,CH₂S); 5.23 (qd,J=7Hz,J'=2Hz, 1H,CH₃-CH.); 7.02 (dd,J=8. Hz,J'=1.6Hz,1H,Ar); 7.97 (m,1H, Ar); 8.06 (dd,J''=5 Hz,J'=1.6 Hz); 9.30 (s,1H,exch.-D₂O,NH).

DESCRIPTION 15

1-(cyclohexyl carbonyl)-2-phenyl hydrazine

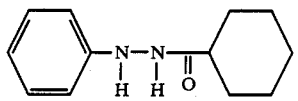
(D15)

To a cooled (0-5° C.) solution of 43.2 g (0.4mol) phenylhydrazine and 35.2 g (0.44 mol) pyridine in 300 ml DMF were added slowly 51 g (0.35 mol) cyclohexane carboxylic acid chloride. The solution was stirred 30 mn more after the end of the addition and concentrated under vacuum. The residue was poured in 300 ml water and stirred 30 mn. Filtration, washing with water and drying led to 74.5 g (98%) of the desired compound. The compound contained traces of starting material and was used without further purification. An analytical sample was obtained from isopropyl ether/ethyl ether
m.p.:207° C.
IR (KBr)ν=3,250; 2,940; 2,860; 1,652; 1,605; 1,498 cm⁻¹.
NMR (CDCl₃)δ=1.2-2.0 ppm (m,10H,cyclohexyl); 2.1-2.3 (m, 1H,CHCO); 6.7-7.3 (m,5H,Ar); 7.52 (s,1H,exch.D₂O,NH). Another NH seems to be present between 3.0 and 4.5 ppm as a very flat m. (exch.D₂O).

DESCRIPTION 16

Spiro cyclohexane-1,3'- 3H indol -2'(1H)-one

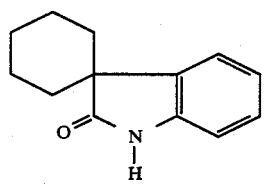
(D16)

An intimate mixture of 7 g (32mol) 1-cyclohexyl carbonyl 2-phenyl hydrazine (Description 15) and 2.3 g (54 mol) calcium hydride was heated to 230° C. with stirring during 45 mn. After cooling, 20 ml water and 30 ml methanol were added. After 1 hr stirring, hydrochloric acid was added until mixture reached pH 1 (15 ml). 10 ml more water were added and the mixture was refluxed 1 hr. After cooling, a 10% sodium hydroxyde solution was added to increase the pH to 3-4. Extraction, with ethyl acetate. The organic layers were washed with water, treated with charcoal and dried over magnesium sulfate. After concentration, the oily residue was purified by chromatography on silica (eluent: methylene chloride/ethyl acetate:9/1).
Yield:3,3 g (51%) of a solid, m.p.:171° C.

IR (KBr)ν=3,150; 3,075; 2,940; 2,860; 1,705; 1,618; 1,470; 1,325; 1,,232 cm⁻¹.
NMR (CDCl₃)δ=1.5-2.0 ppm (m,10H,cyclohexyl). 6.95 (dd,J=8.5 Hz,J'=2.0 Hz,1H,Ar); 7.04 (dd,J=7.6 Hz, J'=1.2 Hz,1H,Ar); 7.20 (dd,J=1.2 Hz,J'=1.7 Hz,1H,Ar); 7.46 (d,J=7.0 Hz,1H,Ar); 8.85(m,1H,exch.-D₂O,NH).

DESCRIPTION 17

5'-[(2-Bromo-1-oxo)propyl]-spiro cyclohexane-1,3'- 3H indol -2'(1H)-one

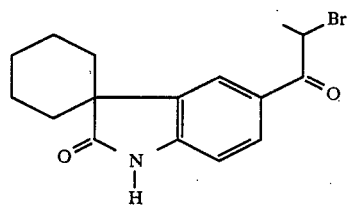
(D17)

5,5 ml DMF were added dropwise to a flask containing 26 g aluminum chloride. The mixture was heated to 70° C. during 0.5 hr. Then 3.5 g (17.3mmol) spiro cyclohexane-1,3'- 3H indol -2'(1H)-one (Description 16) and 3,0 g (17.3 mmol) bromopropionyl chloride were added. The mixture was heated to 80° C. during 1.5 hrs, and then poured on 500 g ice containing 15 ml conc. hydrochloric acid. Stirring 15 mn. The solution was extracted with ethyl acetate. The organic layers were washed with water, dried on magnesium sulfate. After concentration, the residue was triturated with isopropyl ether, filtered and retreated with a mixture of hexane/ethyl acetate: 2/1. After filtration and drying under vacuum, 2.5 g of the desired pure compound was isolated
Yield:43%.
m.p.:187° C.
IR (KBr)ν=3,150; 2,940; 2,860; 1,712; 1,670; 1,610; 1,450; 1,230 cm⁻¹.
NMR (CDCl₃)δ=1.5-2.1 ppm (m,10H,cyclohexyl); 1.91 (d, J=7 Hz,3H,CH₃-CH); 5.28 (q,J=7 Hz,1H,CH₃-CH); 7.02 (d,J=8 Hz, 1H,Ar); 7.97 (dd,J=7 Hz,J'=1.4 Hz,1H,Ar); 7.99 (d,J'=1 Hz,1H, Ar); 8.97 (s,1H,exch.D₂O,NH).

DESCRIPTION 18

5-[(2-Chloro-1-oxo)propyl]-spiro[cyclopropane-1,3'-[3H] indol-2'(1'H)-one

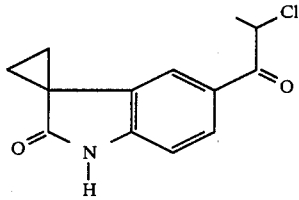
(D18)

Starting from spiro[cyclopropane-1,3'-[3H]-indol]-2'(1'H) -one (m.p.:190° C.; Lit.:180°-187° C.; JACS 71,2031-5 1943) and following the procedure of Description 5 afforded the desired compound.
m.p.=163° C.
IR (KBr)ν=3,000; 1,715; 1,680; 1,615; 1,235; 1,190 cm⁻¹.

NMR (DMSO-d6)δ=1.74 (m,7H,CH3,CH2-CHHD 2); 5.20 (q,1H,J=6.7 Hz,CH); 7.03 (d,1H,J=8.2 Hz,Ar);7.54 (d,1H,J'=1.8 Hz,Ar) ; 7.93 (dd,1H,J=8.2 Hz,J'=1.8 Hz,Ar); 8.7 (s,1H,exch.D2O,NH).

DESCRIPTION 19

1-Benzoyl-5-(2-Chloro-1-oxo)propyl-1,3-dihydro-3,3-dimethyl-2H-indol-2-one

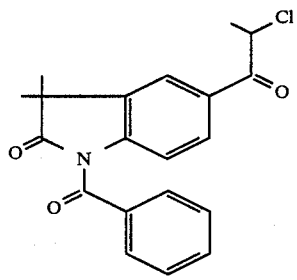

(D19)

2.51 g (1 mmol) 5-[(2 Choro-1-oxo)propyl]-1,3-dihydro-3,3 -dimethyl-2H-indol-2-one (Description 5) and 5 ml benzoylchloride were mixed and heated at reflux (198° C.) for 2 hrs. The excess reagent is distilled off under vacuum. The residue is dissolved in 100 ml ether, quickly washed with a cold diluted solution of sodium hydroxide and twice with water.

The organic phase is dried over MgSO4, treated with activated carbon and evaporated to dryness. Trituration with ispropyl ether afforded 1.3 g of compound used directly in the next step.

NMR (DMSO-d6)δ=1.51 ppm (s,6H,CH3); 1.69 (d,3H,J=6.5 Hz, CH3); 5.84 (q,1H,J=6.5 Hz,CH); 7.5–8.3 (m,8H,Ar).

DESCRIPTION 20

5-[(2-Chloro-1-oxo)propyl]-1,3-dihydro-1,3,3-trimethyl-2H-indol-2-one

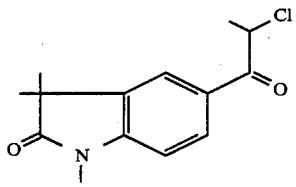

(D20)

Starting from 1,3,3-trimethyl-2H-indol-2-one (m.p.53° C; Lit:55-56° C.; Gazz.Chim.Ital.27,I,72,1897) and following the procedure of Description 5 afforded, after trituration of the residue in isopropyl ether, the desired compound.

m.p.=135° C.

IR (KBr)ν=2,950; 1,720; 1,680; 1,615; 1,500 cm$^{-1}$.

NMR (DMSO-d6)δ1.47 ppm (s,6H,CH3); 1.77 (d,3H,J=6.6 Hz, CH3); 3.35 (s,3H,CH3); 5.91 (q,1H,J=6.6 Hz,CH); 7.3 (m,1H, Ar); 8.16 (m,2H,Ar).

DESCRIPTION 21

1,3-Dihydro-3,3,4-trimethyl-2H-indol-2-one and 1,3-Dihydro3,3,6-trimethyl-2H-indol-2-one

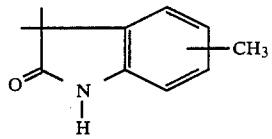

(D21)

A mixture of 19.8 g (0.113mol)-(2-methyl propanoic acid) 2-(3-methyl phenyl) hydrazide, 8.4 g (0.2mol) calcium hydride and 100 ml 1,2,3,4 tetrahydronaphtalene were heated at 190° C. for 2 hrs. The solid was filtered off and the solvent concentrated under reduced pressure. The residue was dissolved in a mixture of methanol (45 ml), water (11 ml) and 10 N hydrochloric acid (22 ml) and left overnight at room temperature. This mixture was then diluted with 500 ml water and extracted twice with 250 ml ethyl acetate. The organic phase was washed twice with 100 ml water dried over MgSO4 and concentrated to dryness. Trituration of the residue with ether afforded 11.2 g (yield 56%) of a cristalline mixture of the two isomers (60/40) used directly in the next step (Description 22).

DESCRIPTION 22

5-[(2-Bromo-1-oxo)propyl]-1,3-dihydro-3,3,4-trimethyl-2H-indol-2-one and 5- (2-Bromo-1-oxo)propyl -1,3-dihydro-3,3,6-trimethyl-2H-indol-2-one

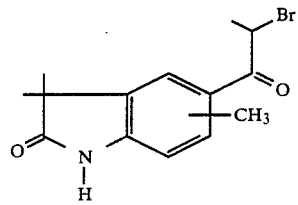

(D22 a and b)

3,5 g Dimethylformamide were added dropwise to 83 g anhydrous aluminum chloride and the exothermic reaction was then allowed to cool to room temperature. Then 10.85 g (62mol) of the mixture obtained in Description 21 and 10.6 g (62mmol) of 2-bromopropionyl chloride were added and stirred at 80° for 1.5 hrs. The reaction mixture was poured on 700 g crushed ice containing 25 ml 10 N hydrochloric acid. The mixture was extracted twice with 250 ml ethyl acetate and washed with water until neutral. The organic phase was dried over MgSO4 and concentrated to dryness. Trituration of the residue with isopropyl ether afforded a cristalline mixture. Recristallization in 75 ml absolute ethanol afforded 6 g of the 6 methyl isomer. (D22 b)

m.p.=220° C.

IR (KBr)ν=3,200; 1,720; 1,675; 1,635; 1,205 cm$^{-1}$.

NMR (CDCl3)δ=1.42 ppm (s,3H,CH3); 1.44 (S.3H,CH3); 1.89 (d,3H,J=6.6 Hz,CH3); 2.54 (s,3H,CH3-Ar); 5.20 (q,1H,J=6.6 Hz, CH); 6.87 (s,1H,Ar); 7.53 (s,1H,Ar); 8.58 (s,1H, exch.D2O, NH).

The mother liquors were concentrated and triturated with ether to afford 4 g of the 4 methyl isomer. (D22 a)

m.p.=170° C.

IR (KBr)ν=3,200; 1,725; 1,680; 1,615; 1,225 cm$_{-1}$.

NMR (CDCl$_3$)δ=1.53 ppm (s,3H,CH$_3$); 1.54 (s,3H,CH$_3$); 1.89 d,3H,J=6.6 Hz,CH$_3$); 2.53 (s,3H,CH$_3$-Ar); 5.22 (q,1H,J=6.6 Hz,C/ ); 6.87 (d,1H,J=8.4 Hz,Ar); 7.58 (d,1H,J=8.4 Hz,Ar); 9.25 (s,1H,exch.D$_2$O,NH).

DESCRIPTION 23

5-[(2-Bromo-1-oxo)propyl]-1,3-dihydro-3,3,7-trimethyl-2H-indol-2-one

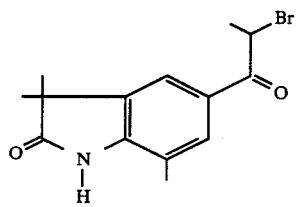
(D23)

Starting from 3,3,7-trimethyl-2H-indol-2-one (Monat.Chem., 27,1184,1906) and following the procedure of description 22, except the final recrystallization step afforded the desired compound, used directly in the next reaction.

m.p.=192°-3° C.

IR (KBr)ν=3,150; 1,715; 1,670; 1,605 ;1,320 ;1,185 cm$^{-1}$.

NMR (CDCl$_3$)δ=1.44 ppm (s,6H,CHHD 3); 1.90 (d,3H, J=6.6 Hz, CH3); 2.40 (s,3H,CH$_3$-Ar); 5.30 (q,1H,J=6.6 Hz,CH); 7.76 (s, 1H,Ar); 7.78 (s,1H,Ar); 9.34 (s,1H,exch.D$_2$O,NH)

DESCRIPTION 24

5-[(2-Bromo-2-methyl-1-oxo)propyl]-1,3-dihydro-3,3-dimethyl- 2H-indol-2-one

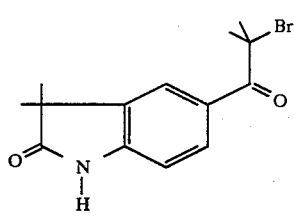
(D24)

2.7 ml Dimethyl formamide were added dropwise to 16.6 g anhydrous aluminum chloride and the exothermic reaction was then allowed to cool to room temperature. Then 2 g (12.4mmol) 3,3-dimethyl-2H-indol-2-one and 2.86 g (12.5mol) 2-bromo-2 methyl propionyl bromide were added and stirred for 1 hr at room temperature. The reaction mixture was poured on 250 g crushed ice containing 25 ml 10N hydrochloric acid. The mixture was extracted twice with 50 ml ethyl acetate and washed three times with water. The organic phase was dried over MgSO$_4$ and concentrated to dryness. The residue was purified by chromatography on silica (hexane/ethyl acetate: 1/1.5) to yield 2 g (52%) of the desired compound.

IR (KBr)ν=3,100; 1,720; 1,665; 1,615; 1,150 cm$^{-1}$.

NMR (CDCl$_3$)δ=1.44 ppm (s,6H,CH3); 2.05 (s,6H,CH3); 6.95 (d,1H,J=8.3 Hz,Ar); 8.02 (d,1H,J'=1.5 Hz,Ar); 8.24 (dd,J=8.3, J'=1.5 Hz,Ar); 8.38 (s,1H,exch.D$_2$O,NH).

DESCRIPTION 25

5-[(2-Bromo-1-oxo)propyl]-1,3-dihydro-3,3-dimethyl-2H-indol-2-one

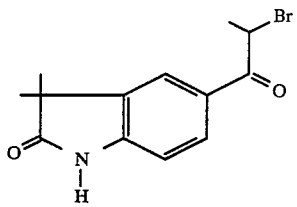
(D25)

100 g anhydrous aluminum chloride and 17 ml dimethyl formamide were mixed and heated with stirring at 70° C. for 30 mn. After cooling at room temperature 12 g (74 mmol) 1,3-dihydro-3,3-dimethyl-2H-indol-2-one and 16.1g (74 mol) 2-bromo propionyl bromide were added and stirred at 80° C. for 1.5 hrs. The mixture was poured onto 600 g crushed ice containing 60 ml 10 N HCl and stirred for 15 mn. The mixture was extracted twice with 250 ml ethylacetate, the organic phase washed twice with water and dried over MgSO$_4$. The solvent is evaporated to dryness. Trituration of the residue with isopropyl ether afforded 12.5 g (57%) of the desired compound used directly in the next step.

IR (KBr)ν=3,300; 1,730; 1,680; 1,620; 1,595; 1,200; 1,155 cm$^{-1}$.

NMR (CDCl$_3$)δ=1.45 (s,6H,CH$_3$); 1.91 (d.3H,J=6.6 Hz,CH$_3$); 5.29 (q,1H,J=6.6 Hz,CH); 7.04 (d,1H,J=8.2 Hz,Ar); 7.95 (m,2H, Ar); 9.25 (s,1H,exch.-D$_2$O,NH).

DESCRIPTION 26

5-[(2-Azido-1-oxo)propyl]-1,3-dihydro-3,3-dimethyl-2H-indol-2-one

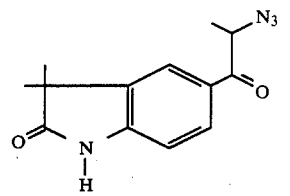
(D26)

20 ml water and 3.2 g sodium azide were added to a solution of 5 g 5-[(2-bromo-1-oxo)propyl]-1,3-dihydro-3,3-dimethyl-2H-indol-2-one (D25) in 45 ml dioxane at room temperature. The reactional mixture was stirred for 1.5 hrs, then 120 ml water were added. The mixture was extracted with 2×200 ml chloroform and the organic solutions were washed with water, dried over Mg SO$_4$ and evaporated to dryness. The residue was crystallised from ligroin to yield 4.19 g of crystals.

m.p.=95° C.

IR (KBr)ν=3,100; 3,000; 2,880; 2,070; 1,715; 1,680; 1,610; 1,215 cm$^{-1}$.

NMR (CDCl$_3$)δ=1.45 ppm (s,6H,CH$_3$); 1.59 (d,3H,J=7.0 Hz, CH$_3$); 4.69 (q,1H,J=7.0 Hz,CH); 7.05 (d,1H,J=8.6 Hz,Ar); 7.85–7.88 (m,2H,Ar); 9.25 (s,1H,exch.D$_2$O,NH).

DESCRIPTION 27

5-[(2-Amino-1-oxo)propyl)]-1,3-dihydro-3,3-dimethyl-2H-indol-2-one, hydrochloride

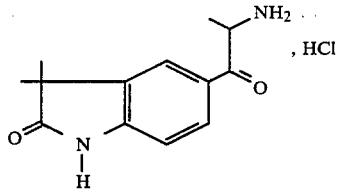

(D27)

4.15 g 5-[(2-azido-1-oxo)propyl]-1,3-dihydro-3,3-dimethyl-2H-indol-2-one (D26), and 0.81 g 10% palladium on charcoal in a mixture of 1.85 ml 12N HCl, 30 ml ethanol and 30 ml chloroform where vigorously stirred at room temperature under hydrogen atmosphere (1 Bar) for about 20 hrs. 250 ml water and 250 ml chloroform were added and the resulting mixture was filtered. The organic phase was extracted with water and the mixed aqueous phases were evaporated to dryness. The residue was triturated in ligroin to yield, 4.23 g of crystals used in the next step without further purification.

m.p. (dec)=about 190° C.

IR (KBr)$\nu$=3,400; 2,950; 1,715; 1,680; 1,615; 1,490; 1,315; 1,200 cm$^{-1}$.

NMR (DMSO-d$_6$)$\delta$=1.32 (s,6H,CH$_3$); 1.44 (d,3H,J=7.1 Hz,CH$_3$); 5.04–5.08 (s,broad,1H,CH); 7.05 (d,1H,J=8.2 Hz,Ar); 7.98 (d,1H,J=8 Hz,Ar); 8.07 (s,1H,Ar); 8.53 (s,broad,2H,exch.D$_2$O, NH$_2$); 11.01 (s,1H,exch.D$_2$O,NH).

DESCRIPTION 28

Ethyl 2-[2-(3,3-dimethyl-2-oxo-1H-indol-5-yl)-1-methyl-2-oxo ethyl]carbamate

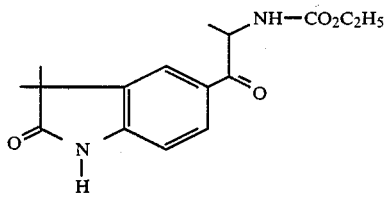

(D28)

16.5 g 5-[(2-Amino-1-oxo)propyl]-1,3-dihydro-3,3-dimethyl-2H-indol-2-one, hydrochloride (D27) was dissolved in a mixture of 35 ml water, 10.4 ml pyridine and 150 ml ethanol. 7.3 g ethyl chloroformate in 15 ml ethanol were added dropwise at room temperature under stirring. The stirring was maintained for 17 hrs and the solvent was evaporated. The residue was taken up in 300 ml water which were then extracted with 2×300 ml methylene chloride. The combined organic phases were washed with water, dried over Mg SO$_4$ and evaporated. The residue was triturated in ligroin to yield 6.3 g of crystals.

m.p.=61°–62° C.

IR (KBr)$\nu$=3,300: 2,970; 1,720; 1,675; 1,615; 1,500; 1,205 cm$^{-1}$.

NMR (CDCl$_3$)$\delta$=1.27 (t,3H,J=7.1 Hz,CH$_3$); 1.43–1.46 (m,9H, CH$_3$); 4.15 (q,2H,J=7.1 Hz,CH$_2$); 5.29–5.36 (m,1H,CH); 5.80 (d,1H,J=7.5 Hz,exch.-D$_2$O,NH); 7.03 (d,1H,J=8.1 Hz,Ar); 7.91 (m,2H,Ar); 8.94 (s,1H,exch.D$_2$O,NH).

DESCRIPTION 29

1,3-Dihydro-5[(2-hydroxy-1-oxo)propyl]-3,3-dimethyl-2H-indol-2-one

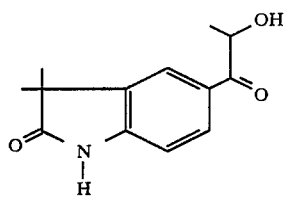

(D29)

10 g 5-[(2-Bromo-1-oxo)propyl]-1,3-dihydro-3,3-dimethyl-2H-indol-2-one (D25), 30 ml DMF and 20 ml water were mixed and heated at 100° C. under stirring during 4 hrs. The solvent was evaporated and the residue purified by chromatography on silica (methylene chloride-acetone: 8/2) to yield 2 g of crystals.

m.p=173° C.

IR (KBr)$\nu$=3,300; 3,170; 2,980; 1,710; 1,680; 1,615; 1,485; 1,210 cm$^{-1}$.

NMR (CDCl$_3$)$\delta$=1.45–1.50 ppm (m,9H,CH$_3$); 3.87 (d,1H, exch. D$_2$O,OH); 5.09–5.23 (m,1H,CH); 7.06 (d,1H,J=8.6 Hz,Ar); 7.80–7.86 (m,2H,Ar); 9.34 (s,1H,exch.D$_2$O,NH).

DESCRIPTION 30

Ethyl 2-[1-(2-hydroxy-propyliden)-1-(3,3-dimethyl-2-oxo-1H--indol-5-yl)]hydrazinecarboxylate.

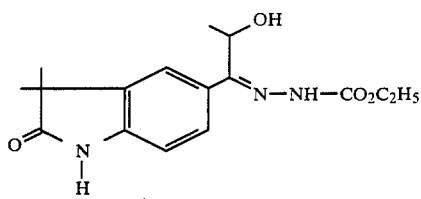

(D30)

2.5 g 1,3-Dihydro -5-[(2-hydroxy-1-oxo)propyl]-3,3-dimethyl-2H-indol-2-one, (D29), 1.29 g ethyl carbazate, 6.25 ml ethanol and 6 drops 0.1 NHCl were mixed and heated to reflux for 10 mn with stirring. The reactional mixture was evaporated to dryness and the residue was triturated in diethyl ether to yield 2.55 g of crystals.

m.p.=213° C.

IR (KBr)$\nu$=3400; 3150; 2970; 1720; 1635; 1510; 1490; 1230 cm$^{-1}$.

NMR (DMSO-d$_6$)$\delta$=1.20–1.37 ppm (m,12H,CH$_3$); 4.14 (q,2H, J=7.0 Hz,CH$_2$); 5.16 (qd,1H,J$_1$=3.2 Hz,CH); 6.51 (d,1H,J=2.8 Hz exch.D$_2$O,OH); 6.86 (d,1H,J=8.1 Hz,Ar); 7.52 (d,1H,J=8.1 Hz, Ar); 7.60 (s,1H,Ar); 10.50 (s,1H,exch.D$_2$O,NH); 11.04 (s,1H, exch.D$_2$O,NH).

DESCRIPTION 31

6-[(2-Bromo-1-oxo)propyl)]-3,4-dihydro-3,3-dimethyl-2(1H)-quinolinone

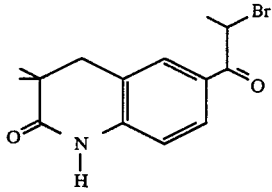
(D31)

1.5 ml DMF were dropwise added to 8.67 g aluminium chloride with external cooling. The corresponding mixture was heated to 70° C. under stirring for 0.5 hr. After cooling to 20° C., 1.15 g 3,4-dihydro-3,3-dimethyl-2-(1H)-quinoline (D. W. Robertson et al., J.Med.Chem.29,1832,1986) and 1.15 g 2-bromopropionyl chloride were added and stirred at room temperature for 15 hrs then poured onto crushed ice. The white precipitate was filtered off, washed with 2N HCl then with water and dried to yield 1.9 g of crystals.

m.p.=224° C.

IR (KBr)$\nu$=3,170; 3,060; 2,960; 1,670; 1,600; 1,510; 1,390; 1,355; 1,300, 1,250 cm$^{-1}$.

DESCRIPTION 32

6-[(2-Bromo-1-oxo)propyl)]-3,4-dihydro-4,4-dimethyl-2(1H)-quinolinone

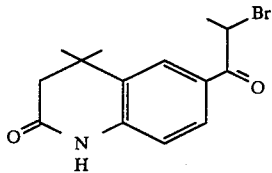
(D32)

2.6 ml DMF were added dropwise to 15.22 g aluminium chloride with external cooling. The corresponding mixture was heated to 70° C. with stirring for 0.5 hr. After cooling to 20° C., 2 g -3,4-dihydro-4,4-dimethyl-2 (1H)-quinolinone (J. Colonge et al. Bull.Soc.Chim.Fr.,982,1953) and 2 g 2-bromopropionyl chloride were added and stirred at room temperature for 1 hr, then poured onto crushed ice. The precipitate was filtered off, washed with 2N HCl then with water, dried and recrystallised from methanol to give 2.3 g of crystals.

m.p.=168° C.

IR (KBr)$\nu$=3,050; 2,950; 1,695; 1,675; 1,590; 1,345; 1,240; cm$^{-1}$.

NMR (CDCl$_3$)$\delta$=1.39 ppm (s,6H,CH$_3$); 1.90 (d,3H,J=6.6 Hz, CH$_3$); 2.55 (s,2H,CH$_2$); 5.26 (q,1H,J=6.6 Hz,CH); 6.93 (d,1H, J=8.3 Hz,Ar); 7.87 (dd,1H,J$_1$=1.9 Hz,J$_2$=8.3 Hz,Ar); 8.03 (d,1H,J=1.9 Hz, Ar); 9.43 (s,1H,exch.D$_2$O,NH).

EXAMPLE 1

1,3-Dihydro-5-(3,6-dihydro-2-oxo-2H-1,3,4-thiadiazin-5-yl)-3-methyl-3-methylthio-2H-indol-2-one

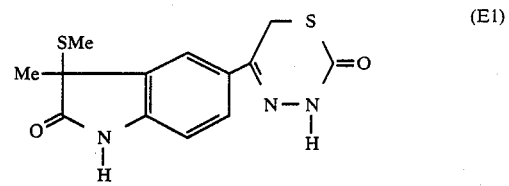
(E1)

0.9 g 5-(2-bromoacetyl)-1,3-dihydro-3-methyl-3-methylthio-2H-indol-2-one, 1.0 g 0-methyl thiocarbazate, and 10 ml acetonitrile were refluxed for 3 hrs. The mixture was purified by chromatography on silica, (hexane/methylene chloride : 1/1; Rf : 0.46) to yield 250 mg of the title compound.

m.p.=213° C.

IR (KBr)$\nu$: 3,150; 1,728; 1,690; 1,635; 1,490; 1,190; 1,128 cm$^{-1}$.

NMR (DMSO-d$_6$)$\delta$=1.55 ppm (s,3H,CH$_3$); 1.90 (s,3H,SCH$_3$); 4.20 (s,2H,CH$_2$S); 6.90 (d,1H,J=8 Hz,Ar); 7.70 (d,1H, J=8 Hz, Ar); 7.75 (s,1H,Ar); 10.75 (s,1H,exch.D$_2$O,NH); 11.45 (s,1H,exch.D$_2$O,NH).

EXAMPLE 2

1,3-Dihydro-5-(3,6-dihydro-2-oxo-2H-1,3,4-thiadiazin-5-yl)-3,3,-dimethyl-2H-indol-2-one

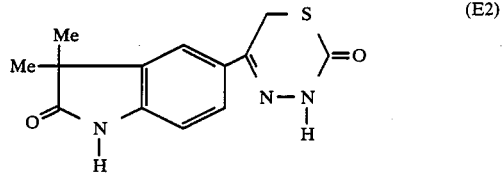
(E2)

1.4 g of 5-(2-chloroacetyl)-1,3-dihydro-3,3-dimethyl-2H-indol-2-one, 0.63 g 0-methyl thiocarbazate, and 20 ml acetonitrile were refluxed for 2 hrs.

After cooling, the crystalline compound was filtered and dried affording 1.1 g of crystals.

m.p.=280° C.

IR (KBr)$\nu$=3,150; 1,720; 1,680; 1,630; 1,495, 1,225 cm$^{-1}$.

NMR (DMSO-d$_6$)$\delta$=1.29 ppm (s,6H,CH$_3$); 4.2 (s,2H,CH$_2$-S); 6.92 (d,1H, J=8 Hz, Ar); 7.7 (m,2H,Ar); 10.5 (s,1H, exch. D$_2$O,NH); 11.42 (s,1H, exch, D$_2$O, NH).

EXAMPLE 3

1,3-Dihydro-5-(3,6-dihydro-6-methyl)-2-oxo-2H-1.3,4-thiadiazin-5-yl)-3,3-dimethyl-2H-indol-2-one

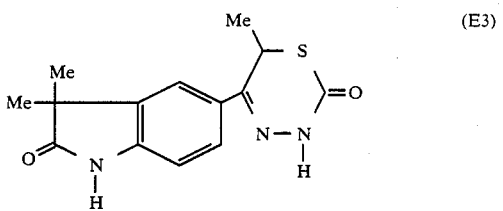
(E3)

1.25 g of 5-[(2-chloro-1-oxo)propyl]-1,3-dihydro-3,3-dimethyl-2H-indol-one, 0.53 g 0-methyl thiocarbazate, and 10 ml acetonitrile were refluxed for 2 hours.

After evaporation to dryness the residual oil was purified by chromatography on silica (hexane/ethylacetate: 1/1) to yield 0.4 g of a crystalline compound.
m.p.=270° C.

IR (KBr)$\nu$=3,170; 1,725; 1,680; 1,620; 1,495; 1,220 cm$^{-1}$.

NMR (DMSO-d$_6$)$\delta$=1.29 ppm (s,6H,CH$_3$); 1.50 (d,3H,J=7.1 Hz,CH$_3$); 4.70 (q,1H, J=7.1 Hz,CH); 6.92 (d,2H,J=8.1 Hz,Ar); 7.70 (m,2H,Ar); 10.51 (s,1H,exch.-D$_2$O,NH); 11.51 (s,1H,exch.D$_2$O,NH).

EXAMPLE 4

1,3-Dihydro-5-(3,6-dihydro-2-oxo-2H-1,3,4-thiadiazin-5-yl)-3-methyl-2H-indol-2-one

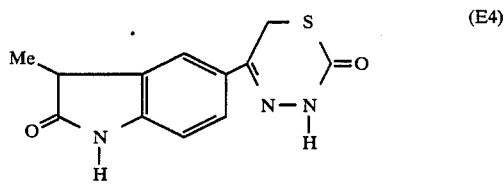
(E4)

1.0 g 5-(2-chloroacetyl)-1,3-dihydro-3-methyl-2H-indol-2-one, 0.37 g O-methyl thiocarbazate, and 20 ml acetonitrile were refluxed for 2 hrs. The precipitate was isolated by filtration and washed with hot acetonitrile to yield a yellowish powder, 450 mg.
m.p.=276° C.

IR (KBr)$\nu$=3,450; 3,200; 1,690; 1,665; 1,620 cm$^{-1}$.

NMR (DMSO-d$_6$)$\delta$=1.32 (d,J=9 Hz,3H,CH$_3$; 3.45 (q,J=9 Hz,1H,CH); 4.15 (s,2H,CH$_2$S); 6.85 (d,1H,Ar); 7.62 (d,1H,Ar); 7.70 (s,1H,Ar); 10.50 (s,1H,exch.-D$_2$O,NH).

EXAMPLE 5

1,3-Dihydro-5-(3,6-dihydro-6-methyl-2-oxo-2H-1,3,4-thiadiazin-5-yl)-3-methyl-3-methylthio-2H-indol-2-one

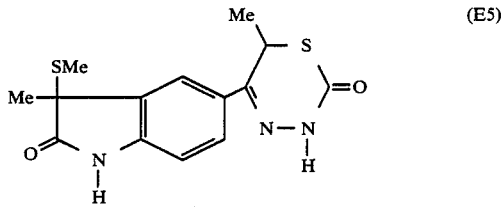
(E5)

Starting from 1-(4-aminophenyl)-2-propanone and following the procedure of Descriptions 1,2 and 3 and Example 1 afforded the desired compound.
m.p.=250° C.

IR (KBr)$\nu$=3,170; 1,725; 1,685; 1,620; 1,490 cm$^{-1}$.

NMR (DMSO-d$_6$)$\delta$=1.49 ppm (d,3H,J=7.2 Hz,CH$_3$; 1.58 (s,3H,CH$_3$); 1.92 (s,3H,SCH$_3$); 4.74 (q,1H,J=7.2 Hz,CH); 6.85 (d,1H,J=8 Hz,Ar); 7.71 (d,1H,J=8 Hz,Ar); 7.8 (s,1H,Ar); 10.74 (s,1H,exch.D$_2$O,NH); 11.55 (s,1H,exch.D$_2$O,NH).

EXAMPLE 6

5'-(3,6-Dihydro-6-methyl-2-oxo-2H-1,3,4-thiadiazin-5-yl)-spiro[cyclopentane-1,3'-[3H]-indol]-2'(1'H)one

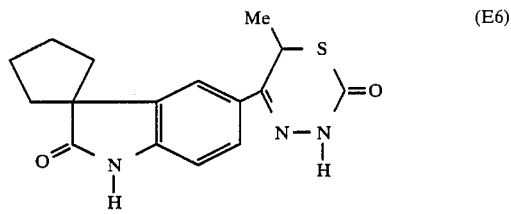
(E6)

Starting from spiro[cyclopentane-1,3'-[2H]indol]-2'-one and following the procedure of Description 5 and Example 3, afforded the desired compound.
m.p.=275° C.

IR (KBr)$\nu$=3,200; 1,705; 1,690; 1,620; 1,485; 1,240 cm$^{-1}$.

NMR (DMSO-d$_6$)$\delta$=1.61 ppm (d,3H,J=7.2 Hz,CH$_3$: 2.00 (m,8H,cyclopentane); 4.36 (q,1H,J=7.2 Hz,CH); 7.00 (d,1H,J=8 Hz,Ar); 7.49 (d,1H,J=8 Hz,Ar); 7.65 (s,1H,Ar); 10.15 (s,1H,exch.D$_2$O,NH); 11.07 (s,1H,exch.D$_2$O,NH).

EXAMPLE 7

1-Acetyl-1,3-dihydro-5-(3,6-dihydro-6-methyl-2-oxo-H-1,3,4-thiadiazin-5-yl)3,3-dimethyl-2H-indol-2-one

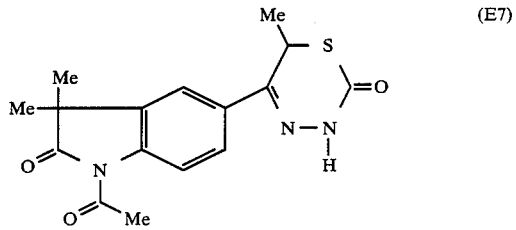
(E7)

Starting from 1-acetyl-5-[(2-chloro-1-oxo)propyl]-1,3-dihydro-3,3-dimethyl-2H-indol-2-one (compound of Description 8) and following the procedure of Example 3 afforded the desired compound.

IR (KBr)$\nu$=3,200; 1,760; 1,705; 1,630, (broad); 1,460; 1,300; 1,270 cm$^{-1}$.

NMR (DMSO-d$_6$)$\delta$=1.46 ppm (s,3H,CH$_3$); 1.62 (d,3H,J=7.2 Hz); 2.67 (s,3H,CH$_3$); 4.44 (q,1H,J=7.2 Hz); 7.68 (d,1H,J=8 Hz,Ar); 7.7 (s,1H,Ar); 8.23 (d,1H,J=8 Hz,Ar); 11.36 (s,1H,exch. D$_2$O,NH).

EXAMPLE 8

1-Acetyl-1,3-dihydro-5-(3,6-dihydro-2-oxo-2H-1,3,4-thiadiazin-5-yl)-3-methyl-2H-indol-2-one

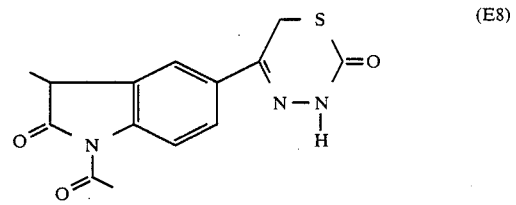
(E8)

0.7 g (2.25 mmol) 1-Acetyl-5-[(2-bromo-1-oxo)ethyl]-1.3-dihydro-3-methyl-2H-indol-2-one (D10), 0.3 g (3.2 mmol) methoxy thiocarbonyl hydrazine and 20 ml acetonitrile were refluxed for 5 hrs. The mixture was concentrated to dryness. The residue, dissolved in 50 ml ethylacetate was washed twice with 50 ml of water, dried over Mg SO$_4$ and evapored to dryness. The residue was purified by chromatography on silica (hexane/ethylacetate:1.5/1) to yield 0.075 g, (yield 10%), of the desired compound.

m.p.=223° C.

IR (KBr)ν=3,200; 1,760; 1,715; 1,650; 1,615; 1,310; 1,180 cm$^{-1}$.

NMR (CDCl$_3$)δ=1.47 ppm (d,3H,J=7.5 Hz,CH$_3$; 3.87 (q,1H, J=7.5 Hz,CH); 4.25 (s,2H,CH$_2$); 7.82 (m,2H,Ar); 8.15 (m,1H, Ar); 11.63 (s,1H,exch. D$_2$O,NH).

EXAMPLE 9

1-Acetyl-1,3-dihydro-5-(3,6-dihydro-2-oxo-2H-1,3,4-thiadiazin-5-yl)-3-methyl-3-methylthio-2H-indol-2-one

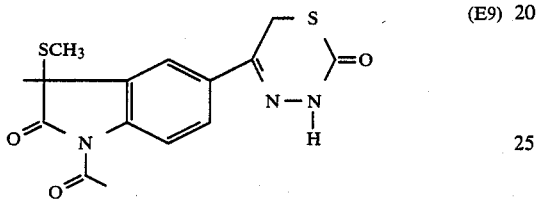

(E9)

0.131 g sodium hydride from a 55% dispersion in mineral oil was added during 0.5 hr to a solution of 0.921 g of 1,3-dihydro-5-(3,6-dihydro-2-oxo-2H-1,3,4-thiadiazin-5-yl)-3-methyl-3-methylthio-2H-indol-2-one (compound of Example 1) in 25 ml DMF at 5° C. The mixture was stirred for 0.5 hr at 5° C. then 0.5 hr at 20° C. and cooled at 5° C. 0.215 ml of acetyl chloride in 1 ml DMF was added dropwise under stirring. The mixture was stirred for 0.5 hr at 5° C. then 1.5 hrs at 20° C. 250 ml ethylacetate was added and the corresponding organic solution was washed with water, dried and evaporated to dryness. The residual oil was purified by chromatography on silica (methylene chloride-ethylacetate: 9/1) to yield 0.4 g of white crystalline compound.

m.p.=198° C.

IR (KBr)ν=3,270; 1,740; 1,710; 1,660; 1,380; 1,300 cm$^{-1}$.

NMR (CDCl$_3$)δ=1.78 ppm (s,3H,CH$_3$); 2.06 (s,3H,SCH$_3$); 2.72 (s,3H,N(CO)CH$_3$); 4.01 (s,2H,CH$_2$-S); 7.68 (dd,1H,J$_1$=1.9 Hz, J$_2$=8.6 Hz,Ar); 7.81 (d,1H,J=1.9 Hz,Ar); 8.31 (d,1H,J=8.6 Hz, Ar); 8.91 (s,1H,exch.D$_2$O,NH).

EXAMPLE 10

1,3-Dihydro-5-(3,6-dihydro-6-methyl-2-oxo-2H-1,3,4-thiadiazin-5-yl)-3-methylthio-2H-indol-2-one

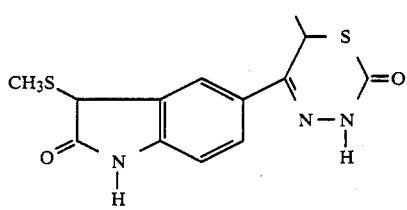

(E10)

A mixture of 20 g (crude; 74 mmol) 5- (2-chloro-1-oxo)propyl-1,3-dihydro-3-methylthio-2H-indol-2-one (D11), 7.9 g, (74 mmol) methoxy thiocarbonylhydrazine (K. A. Jensen, U. Anthoni, A. Holm, Acta Chem.- Scand.,23,1916,1969). In 300 ml acetonitrile were refluxed overnight. Concentration followed by trituration in hexane/ethyl acetate: 1/1 yielded 18 g of yellow crystals. The filtrate after concentration and chromatography on silica gel (eluent: Hex/AcOEt:1/1) afforded another 2 g crop.

Yield: 20 g (88%).

m.p.=159° C.

IR (KBr)ν=3,200; 1,700; 1,620; 1,495 cm$^{-1}$.

NMR (DMSO-d$_6$)δ=1.48 ppm (d,J=7 Hz,3H,CH$_3$CH); 2.23 (s,3H, CH$_3$S); 4.57 (s,1H,exch.- D$_2$O,CHS); 4.69 (q,J=7 Hz,1H,CHCH$_3$); 6.91 (d,J=8 Hz,1H,Ar); 7.70 (d,J=8 Hz,1H,Ar); 7.75 (s,1H,Ar); 10.72 (s,1H,exch.D$_2$O,NH); 11.55 (s,1H,exch.D$_2$O,NH).

EXAMPLE 11

1,3-Dihydro-5-(3,6-dihydro-2-oxo-2H-1,3,4-thiadiazin-5-yl) -3-methylthio-2H-indol-2-one

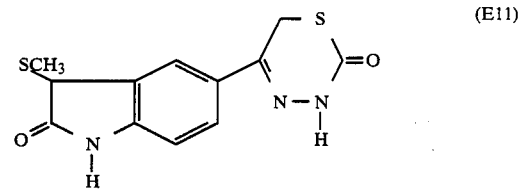

(E11)

Starting from 5- (2-Chloro-1-oxo)ethyl -1,3-dihydro-3-methylthio-2H-indol-2-one (D12) and methoxy thiocarbonylhydrazine and according to the procedure described in Example 10, afforded the desired compound.

Yield: 55% m.p.=201°-204° C.

IR (KBr)ν=3,200; 1,715; 1,640; 1,625; 1,500 cm$^{-1}$.

NMR (DMSO-d$_6$)δ=1.99 (s,3H,CH$_3$S); 4.14 (s,2H,COCH$_2$S); 4.54 (s,1H,CHS); 6.93 (d,J=8 Hz,1H,Ar); 7.70 (d,J=8 Hz,1H,Ar); 7.76 (s,1H,Ar); 10.73(s,1H,exch.D$_2$O,NH); 11.46 (s,1H,exch. D$_2$O,NH).

EXAMPKE 12

5-(3,6-Dihydro-6-methyl-2-oxo-2H-1,3,4-thiadiazin-5-yl)-1H-indole-2,3-dione

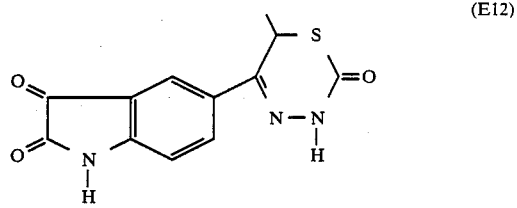

(E12)

3.30 g (10.8 mmol) 1,3 Dihydro-5-(3,6-dihydro-6-methyl-2-oxo-2H-1,3,4-thiadiazin-5-yl)-3-methylthio-2H-indol-2-one, (Example 10), 1.89 g (14 mmol) N-chlorosuccinimide and 250 ml methylene chloride were stirred overnight at room temperature. After concentration the residue was taken up in a minimum volume of THF. This solution was added to a suspension of 2.34 g (10.8 mmol) mercury (II) oxide, 1.52 g (10.8 mmol) boron trifluoride etherate in 75 ml THF and 75 ml water. After 1 hr stirring, 100 ml chloroform were added and the suspension was filtered. The filtrate was extracted with chloroform. The organic layers were washed with water, and dried over magnesium sulfate.

The compound was purified by column chromatography (silica, eluent:chloroform/methanol:97/3).
Yield: 60% red crystals.
m.p.=131° C.
IR (KBr)=3,280; 1,745; 1,655; 1,620; 1,495; 1,200 cm$^{-1}$.
NMR (DMSO-d$_6$)=1.52 (d,J=7 Hz,3H,CH$_3$CH); 4.62 (q,J=7 Hz,1H, CHCH$_3$); 6.97 (d,J'=8 Hz,1H,Ar); 7.96 (dd,J=1.5 Hz,J'=8 Hz,1H, Ar); 8.10 (d,J=1.5 Hz,1H,Ar); 11.18 (s,1H,exch.D$_2$O,NH); 11.45(s,1H,exch.D$_2$O,NH).

EXAMPLE 13

5'-(3,6-Dihydro-6-methyl-2-oxo-2H-1,3,4 thiadiazin-5-yl) -spiro 1,3-dithiolane-2,3'- 3H indol-2(1'H)-one

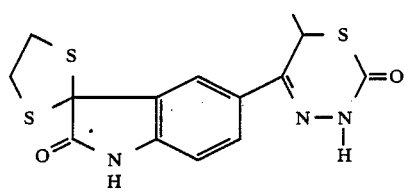

(E13)

500 mg (1.8 mmol) 5-(3,6-Dihydro-6-methyl-2-oxo-2H-1,3,4-thiadiazin-5-yl)-1H-indole-2,3-dione (Example 12) were suspended in 80 ml acetic acid and 1 ml boron trifluoride etherate and 500 mg ethanedithiol were added. The suspension was stirred overnight and then poured in 350 ml water. The white precipitate was filtered, washed with water, then with ether and dried under vacuum.
Yield: 260 mg (40%)
m.p.=157° C.
IR(KBr)=3,200; 1,720; 1,620; 1,595 cm$^{-1}$.
NMR (DMSO-d$_6$)=1.54 (d,J=7 Hz,3H,CH$_3$CH); 3.75 (A$_2$B$_2$,J=2 Hz,4H,CH$_2$-CH$_2$); 4.54 (q,J=7 Hz,1H,CHCH$_3$); 6.88 (d,J=8 Hz,1H,Ar); 7.65 (dd,J=8 Hz,J'=1.5 Hz,1H,Ar); 7.87 (d,J=1.5 Hz,1H,Ar); 10.66 (s,1H,exch.D$_2$O,NH); 11.35 (s, 1H,exch.D$_2$O,NH).

EXAMPLE 14

5'-(3,6-Dihydro-6-methyl-2-oxo-2H-1,3,4-thiadiazin-5-yl)-spiro[1,3-dithiane-2,3'-[3H]indol]-2(1'H)-one

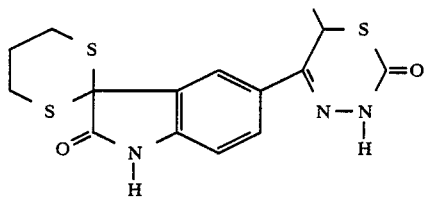

(E14)

Starting from 5-(3,6-Dihydro-6-methyl-2-oxo-2H-1,3,4-thiadiazin-5-yl)-1H-indole-2,3-dione (Example 12), following the procedure of Example 13, but using propanedithiol instead of ethanedithiol, afforded the desired compound.
Yield: 15%.
m.p.=286° C.
IR (KBr)ν=3,200; 1,710; 1,645; 1,615; 1,495; 1,272 cm$^{-1}$.
NMR (DMSO-d$_6$)δ=1.47 ppm (d,J=7 Hz,3H,CH$_3$CH); 1.8-2.3 (m,2H,SCH$_2$CH$_2$CH$_2$S); 2.7-2.9 (m,2H,SCH$_2$); 3.7-3.9 (m,2H, SCH$_2$); 4.74 (q,J=7 Hz,1H,CHCH$_3$); 6.98 (d,J=8 Hz,1H,Ar); 7.75 (d,J=8 Hz,1H,Ar); 7.78 (s,1H,Ar); 11.0 (m,1H,exch.-D$_2$O,NH); 11.66 (s,1H,exch.D$_2$O,NH).

EXAMPLE 15

1,3-Dihydro-5-(3,6-dihydro-6-methyl-2-oxo-2H-1, 3,4-thiadiazin-5-yl)-3.3-di(methylthio)-2H-indol-2 one

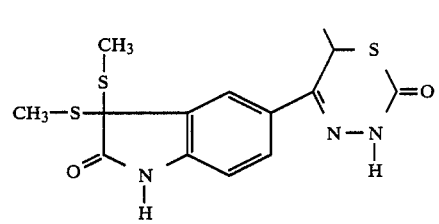

(E15)

In a pressure vessel were introduced at −50° C., 1 g (3.6 mmol) 5-(3,6-dihydro-6-methyl-2-oxo-2H-1,3,4 thiadiazin-5-yl)-1H-indole-2,3-dione (Example 12), 75 ml acetic acid, 2 ml boron trifluoride etherate and 5 g methanethiol. The reactor was closed and stirred at room temperature during 24 hrs. The mixture was poured in 500 ml water. The precipitate was filtered, washed with water and dried under vacuum.
Yield: 450 mg (35%) beige crystals.
m.p.=99°dec.
IR (KBr)ν=3,250; 1,720; 1,620; 1,495; 1,290; 1,245; 1,205 cm$^{-1}$.
NMR (CDCl$_3$)δ=1.69 (d,J=7 Hz,3H,CH$_3$CH); 2.22 (s,6H,CH$_3$S); 4.27 (q,J=7 Hz,1H,CH$_3$CH); 7.02 (d,J=8 Hz,1H,Ar); 7.68 (d,J=8 Hz, 1H,Ar); 7.82 (s,1H,Ar); 9.16 (s,1H exch.D$_2$O,NH); 9.35 (s,1H,exch.D$_2$O,NH).

EXAMPLE 16

5'-(3,6-Dihydro-6-methyl-2-oxo-2H-1,3,4 thiadiazin-5-yl) -spiro[cyclopropane-1,3'-[3H]indol]-2'-(1'H)-one

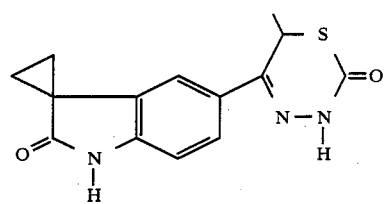

(E16)

0.5 g (2 mmol) 5-[(2-Chloro-1-oxo)propyl]-spiro [cyclopropane-1,3'-[3H]-indol]-2'-(1'H)-one (D18), 0.3 g (3.2 mmol) methoxy thiocarbonylhydrazine and 6 ml acetonitrile were refluxed for 6 hrs. The precipitate was isolated by filtration and washed with ether to yield 0.28 g.
Yield: 49%.
m.p.=281° C.
IR (KBr)ν=3,175; 1,720; 1,620; 1,605; 1,230 cm$^{-1}$.
NMR (DMSO-d$_6$)δ=1.54 ppm (m,7H,CH$_3$,CH$_2$-CH$_2$); 4.64 (q,1H,J=7.2 Hz,CH); 6.97 (d,1H,J=8.2 Hz,Ar); 7.40 (d,1H,J'=1.2 Hz,Ar); 7.64 (dd,1H,J=8.2,J'=1.2 Hz,Ar); 10.70 (s,1H,exch.-D$_2$O,NH).

EXAMPLE 17

5'-(3,6-Dihydro-6-methyl-2-oxo-2H-1,3,4 thiadiazin-5-yl) -spirocyclohexane-1,3'-[3H]indol]-2'-(1'H)-one

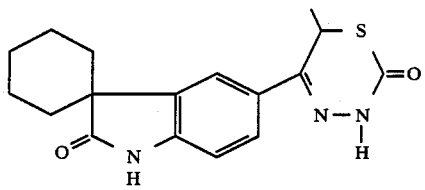
(E17)

Starting from 5'-[(2-Bromo-1-oxo)propyl]-spiro[cyclohexane -1,3'-[3H]-indol]-2'(1H)-one (D17) and following the procedure of Example 10, the desired compound was obtained.

Yield: 21% m.p.=235° C.

IR (KBr)$\nu$=3,175; 3,075; 2,920; 2,850; 1,705; 1,645; 1,615 1,500; 1,445 cm$^{-1}$.

NMR (DMSO-d$_6$)$\delta$=1.48 ppm (d,J=7 Hz,3H,CH$_3$CH); 1.4-2.0 (m, 10H,cyclohexyl); 4.77 (q,J=7 Hz,1H,CH$_3$-CH); 6.92 (d,J=8.2 Hz, 1h,Ar); 7.66 (dd,J'=1.4 Hz,J=8.2 Hz,1H,Ar); 7.90 (s,1H,Ar); 10.60 (s,1H,exch.D$_2$O,NH); 11.60 (s,1H,exch.D$_2$O,NH).

EXAMPLE 18

1,3-Dihydro-5-(3,6-dihydro-6-methyl-2-oxo-2H-1,3,4-thiadiazin-5-yl)-1,3,3-trimethyl-2H-indol-2-one

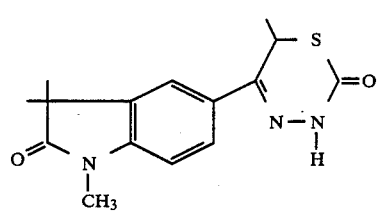
(E18)

Starting from 5-[(2-Chloro-1-oxo)propyl]-1,3-dihydro-1,3,3-trimethyl-2H-indol-2-one (D20), and following the procedure of Example 3 afforded the desired compound.

m.p.=125° C.

IR (KBr)$\nu$=3,175; 1,705; 1,620; 1,500; 1,225 cm$^{-1}$.

NMR (DMSO-d$_6$)$\delta$=1.34 ppm (s,6H,CH$_3$); 1.53 (d,3H,J=7.1 Hz, CH$_3$); 3.20 (s,3H,CH$_3$); 4.76 (q,1H,J=7.1 Hz,CH); 7.11 (m,1H,Ar): 7.78 (m,2H,Ar); 11.55 (s,1H,exch.D$_2$O,NH).

EXAMPLE 19

5'-(3,6 Dihydro-3,6-dimethyl-2-oxo-2H-1,3,4-thiadiazin-5-yl)-1'-methyl-spiro[cyclopentane-1,3'-[3H]-indol]-2'-(1'H)-one

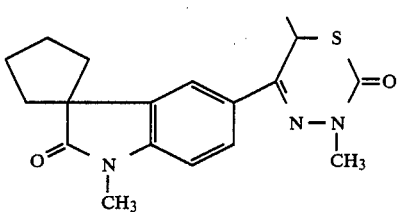
(E19)

0.76 g (19 mmol) washed potassium hydride, 75 ml dry DMF and 3 g (9.5 mmol) 5'-(3,6-dihydro-6-methyl-2-oxo-2H-1,3,4-thiadiazin-5-yl)-spiro-[cyclopentane-1,3'-[3H]-indol]-2'(1'H)-one (Example 6) were stirred at room temperature during 30mn. 2.8 g (20 mmol) methyliodide were added and the stirring was continued for 1 hr. 150 ml water were added and the mixture was extracted with ethyl acetate. The organic layer was dried over magnesium sulfate. The crude product was purified by column chromatography on silica (eluent-:methylen chloride/methanol: 99.5/0.5).

Yield: 50% m.p.=149° C.

IR (KBr)$\nu$=2,950; 1,715; 1,620; 1,505; 1,342; 1,260; 1,065 cm$^{-1}$.

NMR (CDCl$_3$)$\delta$=1.63 ppm (d,J=7z,3H,CH$_3$—CH—); 1.8-2.3 ppm (m, 8H,cyclopentyl); 3.24 (s,3H,NCH$_3$); 3.58(s,3H,N-CH$_3$); 4.22 (q,J=7 Hz,1H,CH$_3$—CH—); 6.85 (d,J=8 Hz,1H,Ar); 7.55 (dd,J=8 Hz,J'=1.8 Hz,1H,Ar); 7.67 (d,J=1.8 Hz,1H,Ar).

EXAMPLE 20

5'-(3,6-Dihydro-2-oxo-2H-1,3,4-thiadiazin-5-yl)-spiro [thiolane-2,3'-[3H]-indol]-2'(1'H)-one

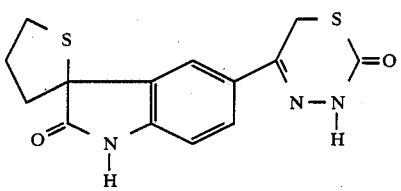
(E20)

Starting from 5'-[(2-Chloro-1-oxo)ethyl]-spiro thiolane-2, 3'- 3H -indol -2(1'H)-one and following the procedure of Example 10, afforded the desired compound.

Yield: 40%.

m.p.=284° C.

IR (KBr)$\nu$=3,150; 1,712; 1,632; 1,610; 1,495 cm$^{-1}$.

NMR (DMSO-d$_6$)$\delta$=2.1-3.5 ppm (m,6H,CH$_2$CH$_2$CH$_2$S); 4.19 (s,2H, CH$_2$S); 6.90 (d,J=8 Hz,1H,Ar); 7.68 (dd,J=8 Hz,J'=1.8 Hz, 1H, Ar); 7.81 (d,J'=1.8 Hz,1H,Ar); 10.64(s,1H,exch.D$_2$O,NH);11.44 (s,1H,exch.D$_2$O,NH).

EXAMPLE 21

5'-(3,6-Dihydro-6-methyl-2-oxo-2H-1,3,4-thiadiazin-5-yl)-spiro-[thiolane-2,3'-[3H]-indol]-2'(1'H-one

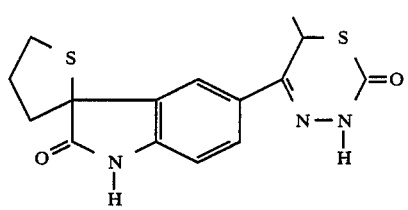
(E21)

Starting from 5,-[(2-Chloro-1-oxo)propyl]-spiro thiolane-2, 3'-[3H]-indol]-2(1'H)-one and following the procedure of Example 10, afforded the desired compound.

Yield : 46%.

m.p.=205° C.

IR (KBr)$\nu$=3,200; 1,705; 1,620; 1,490 cm$^{-1}$.

NMR (DMSO-d$_6$)$\delta$=1.47 (2d,at 1.46 and 1.48 ppm,J=7.1 Hz,3H, C$\underline{H}_3$CH); 2.1–2.6 (m,4H,C$\underline{H}_2$C$\underline{H}_2$CH$_2$S); 3.1–3.2 (m,2H,C$\underline{H}_2$S); 4.75 (2q,2 diastereoisomers at 4.73 ppm and 4.77 ppm,J=7.1 Hz,1H, CH$_3$C$\underline{H}$); 6.90 (d,J=8.2 Hz,1H,Ar); 7.70 (m,1H,Ar); 7.83 (s,1H, Ar); 10.71 (s,1H,exch.D$_2$O,N$\underline{H}$); 11.61 (s,1H,exch.D$_2$O,N$\underline{H}$).

EXAMPLE 22

1-Benzoyl-1,3-dihydro-5-(3,6-dihydro-6-methyl-2-oxo-2H-1,3, 4-thiadiazin-5-yl)-3,3-dimethyl-2H-indol-2-one

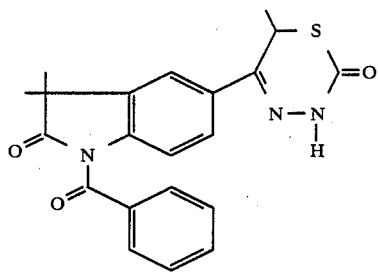
(E22)

Starting from 1-benzoyl-5-[(2-chloro-1-oxo)propyl]-1,3-dihydro-3,3-dimethyl-2H-indol-2-one (D19) and following the procedure of Example 3 afforded the desired compound.

m.p.=200° C.

IR (KBr)$\nu$=3,200; 1,760; 1,690; 1,630; 1,275 cm$^{-1}$.

NMR (DMSO-d$_6$)$\delta$=1.46 ppm (s,6H,C$\underline{H}_3$); 1.51 (d,3H,J=7.1 Hz,C$\underline{H}_3$); 4.77 (q,1H,J=7.1 Hz,C$\underline{H}$); 7.5–7.9 (m,8H,Ar); 11.64 (s,1H,exch. D$_2$O,N$\underline{H}$).

EXAMPLE 23

1,3-Dihydro-5-(3,6-dihydro-6-methyl-2-oxo-2H-1,3,4-thiadiazin-5-yl)-3,3-dimethyl-1-[(4-pyridyl)carbonyl-2H-indol]-2-one

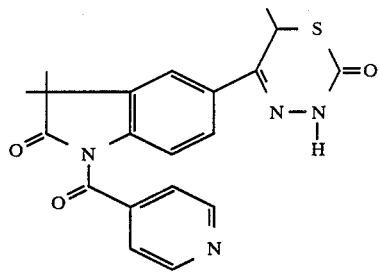
(E23)

1 g (3.45 mmol) 1,3-Dihydro-5-(3,6-dihydro-6-methyl-2-oxo-2H-1,3,4-thiadiazin-5-yl)-3,3 dimethyl-2H-indol-2-one (Example 3) dissolved in 15 ml DMF were added to a suspension of 0.3 g (7.5 mmol) washed potassium hydride in 15 ml DMF. The mixture was stirred 30mn at room temperature under argon, and 0.65 g (3,6 mmol) isonicotinoyl chloride hydrochloride were added in one portion. Stirring 30mn at room temperature. 50 ml water were added, and the solution was extracted with ethylacetate after slight basification with sodium hydrogenocarbonate. The organic layers were washed with brine and dried over magnesium sulfate. Purification by chromatography on silica (eluent:-chloroform/methanol:95/5), followed by a second chromatography (chloroform/methanol:98/2). The crystals were then triturated with isopropyl ether and dried under vacuum.

Yield: 750 mg (55%).

m.p.=234° C.

IR (KBr)$\nu$=3,200; 3,160; 2,975; 2,910; 1,765; 1,690; 1,642; 1,615; 1,485; 1,345; 1,305; 1,235; 1,140 cm$^{-1}$.

EXAMPLE 24

1,3-Dihydro-5-(3,6-dihydro-6-methyl-2-oxo-2H-1,3,4-thiadiazin-5-yl)-3,3 dimethyl-1-[(3-pyridyl)carbonyl]-2H-indol-2-one

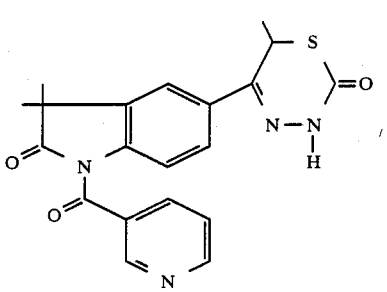
(E24)

Starting from 1,3-dihydro-5(3,6-dihydro-6-methyl-2-oxo-2H-1,3,4 thiadiazin-5-yl)-3,3 dimethyl-2H-indol-2-one (Example 3) and according to the method described in Example 23, but using nicotinoyl chloride instead of isonicotinoyl chloride, afforded the desired compound.

Yield: 55% m.p.=245° C.

IR (KBr)$\nu$=3,225; 3,050; 2,975; 1,755; 1,700; 1,640; 1,618; 1,345; 1,305 cm$^{-1}$.

NMR (CDCl₃)δ=1.53 (s,6H,CH₃CCH₃); 1.71 (d,J=7 Hz,3H,CH₃CH); 4.33 (q,J=7 Hz,1H,CHCH₃); 7.45 (dd,J=4.8 Hz,J'=7.8 Hz,1H, Ar); 7.64 (dd,J=4.9 Hz,J'=8.6 Hz,1H,Ar); 7.82 (d,J'=1.8 Hz,1H,Ar); 7.98 (dd,J=2.0 Hz,J'=4.0 Hz,1H,Ar); 8.04 (d,J=8.6 Hz,1H,Ar); 8.81 (dd,J=1.7 Hz,J'=4.9 Hz,1H,Ar); 8.89 (d,J=1.8 Hz,1H,Ar); 9.30 (s,1H,exch.D₂O,NH).

EXAMPLE 25

1,3-Dihydro-5-(3,6-dihydro-6-methyl-2-oxo-2H-1,3,4-thiadiazin-5-yl)-3,3-dimethyl-1-(4-nitrobenzoyl)-2H-indol-2-one

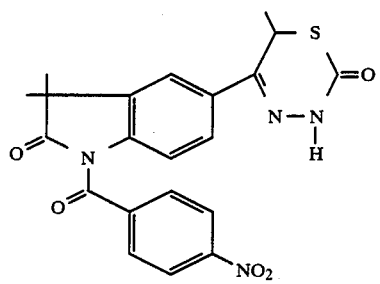
(E25)

2.9 g (10 mmol) 1,3-dihydro-5(3,6-dihydro-6-methyl-2-oxo-2H-1,3,4 thiadiazin-5-yl)-3,3 dimethyl-2H-indol-2-one (Example 3), 0.4 g (10 mmol) sodium hydroxyde and 100 ml ethanol were refluxed 30mn. After evaporation of the solvent, the residue was dissolved in 50 ml DMF and 1.86 g (10 mmol) p-nitrobenzoyl chloride were added while keeping the temperature under 30° C. The mixture was stirred 2 hrs at room temperature, diluted with 100 ml water, extracted with ethyl acetate. The organic layers were washed with brine and dried over magnesium sulfate. The residue was purified by column chfomatography on silica (eluent:ethylacetate/hexane:1/1) and the major fraction was triturated in isopropyl ether and dried under vacuum.

Yield: 1.3 g (30%).
m.p.=226°-228° C.
IR (KBr)ν=3,375; 3,075; 2,975; 1,770; 1,692; 1,645; 1,615; 1,525; 1,340; 1,305 cm⁻¹.

EXAMPLE 26

1,3-Dihydro-5(3,6-dihydro-6-methyl-2-oxo-2H-1,3,4-thiadiazin-5-yl)-3,3-dimethyl-1-(phenylmethylcarbonyl)-2H-indol-2-one

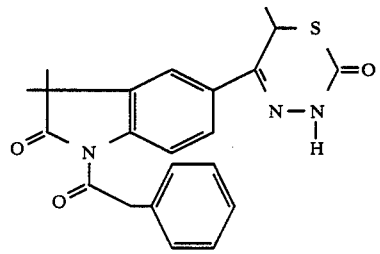
(E26)

Starting from 1,3-dihydro-5(3,6-dihydro-6-methyl-2-oxo-2H-1,3,4-thiadiazin-5-yl)-3,3-dimethyl-2H-indol-2-one (Example 3), this compound was synthesised according to the method described for Example 23 using only one equivalent of potassium hydride and phenylacetyl chloride instead of isonicotinoyl chloride. If an excess of potassium hydride is used in this reaction (2 equivalents) a by-product (described in Example 28) is obtained as the major fraction.

Yield: 11%
m.p.=219° C.
IR (KBr)ν=3,200; 3,075; 2,975; 2,925; 1,760; 1,712; 1,630; 1,615; 1.348; 1.265; 1,130 cm⁻¹.

NMR (CDCl₃)δ=1.47 (s,6H,2xCH₃); 1.68 (d,J=7 Hz,3H,CH₃CH); 4.29 (q,J=7 Hz,1H,CH₃CH-); 4.45 (s,2H,CH₂,Ar); 7.20–7.40 (m, 5H,Ar); 7.55 (dd,J=1.9 Hz,J'=8.6 Hz,1H,Ar); 7.75 (d,J=1.9 Hz, 1H,Ar); 8.28 (d,J'=8.6 Hz,1H,Ar); 9.12 (s,1H,exch.D₂O,NH).

EXAMPLE 27

5'-(3 6-Dihydro-6-methyl-2-oxo-2H-1,3,4-thiadiazin-5-yl)-1'-[(4 pyridyl)carbonyl]-spiro[cyclopentane-1,3'-[3H]indol]-2'(1'H)-one

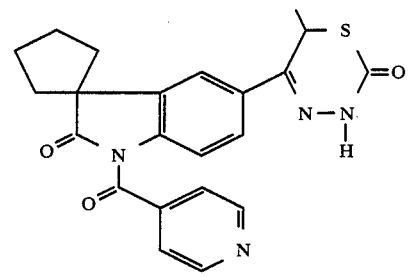
(E27)

Starting from 1',3'-dihydro-5'-(3,6-dihydro-6-methyl-2-oxo-2H-1,3,4 thiadiazin-5-yl)-spiro cyclopentane-1,3'-2H-indol -2'-one (Example 6) and following the procedure described in Example 23, the desired compound was obtained.

Yield: 19%.
m.p.=219°-20° C.
IR (KBr)ν=3,400; 3,325; 3,050; 2,950; 1,760; 1,690; 1,635; 1,618; 1,350; 1,305 cm⁻¹.

NMR (DMSO-d₆)δ=1.50 (d,J=7 Hz,3H, CH₃CH); 1.7–2.3 (m,8H, cyclopentyl); 4.85 (q,J=7 Hz,1H,CH₃-CH); 7.63 (d,J=6 Hz,2H, pyridine); 7.85 (d,J=9 Hz,1H,Ar); 7.87 (s,1H,Ar); 8.04 (d,J=9 Hz,1H,Ar); 8.74 (d,J=6 Hz,2H,pyridine); 11.74 (s,1H, exch.D₂O,NH).

EXAMPLE 28

1-[2,3-Dihydro-5-(3,6-dihydro-6-methyl-2-oxo-2H-1,3,4-thiadiazin-5-yl)-3,3-dimethyl-2-oxo-1H-indolyl]-2,4-diphenyl-1,3-butanedione

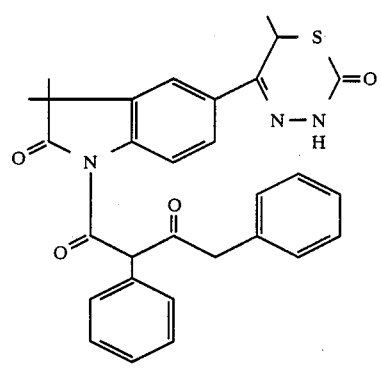
(E28)

Starting from 1,3-Dihydro-5(3,6-dihydro-6-methyl-2-oxo-2H-1,3,4-thiadiazin-5-yl)-3,3-dimethyl-2H-indol-2-one (Example 3), this compound was obtained as a major product if synthesised according to the method described in Example 26 using an excess of potassium hydride.

Yield: 13%.
m.p.=175° C.
IR (KBr)ν=3,210; 3,050; 2,975; 2,925; 1,755; 1,715; 1,650 1,620 cm⁻¹.
NMR (CDCl₃)δ=1.47 ppm (d,J=8 Hz,6H,2xCH₃); 1.67 (d,J=7 Hz, 3H,CH₃CH); 3.89 (A₂B₂,$J_{aa}$=17 Hz,$J_{ab}$;42 Hz,2H,CH₂,Ar); 4.28 (q,J=7 Hz,1H,CH₃CH); 6.03 (s,1H,CH,Ar); 6.9–7.4 (m,10H,2xAr) 7.53 (d,J=8.7 Hz,1H,Ar); 7.74 (m,1H,Ar); 8.30 (d,J=8.7 Hz,1H, Ar); 9.05 (s,1H,exch.-D₂O,NH).

EXAMPLE 29

5-(3,6-dihydro-6-methyl-2-oxo-1,3,4-thiadiazin-5-yl)-1,3-dihydro-3,3,4-trimethyl-2H-indol-2-one

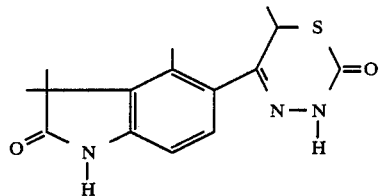
(E29)

A mixture of 2 g (6.45 mmol) 5-[(2-Bromo-1-oxo)propyl]-1,3-dihydro-3,3,4-trimethyl-2H-indol-2-one (D22a), 0.95 g (6.45 mmol) 0-t butylthiocarbazate, 0.75 g (7.5 mmol) triethylamine and 50 ml ethanol was refluxed for 3 hrs and then concentrated to dryness. The residue was poured in 200 ml water, extracted twice with 50 ml ethyl acetate. The organic phase was washed twice with 50 ml water, dried over MgSO4, treated with activated carbon and concentrated to dryness. The residue was purified by chromatography on silica (hexane/ethylacetate:1.5/1) to yield 0.42 g of the desired compound.

m.p.=279° C.
IR (KBr)ν=3,200; 1,700; 1,650; 1,615; 1,230 cm⁻¹.
NMR (DMSO-d₆)δ=1.35 ppm (s,6H,CH₃); 1.40 (d,3H,J=7.1 Hz,CH₃); 2.34 (s,3H,CH₃,Ar); 4.18 (q,1H,J=7.1 Hz,CH); 6.77 (d,1H,J=7.9 Hz,Ar); 7.15 (d,1H,J=7.9 Hz,Ar); 10.53 (s,1H,exch.D₂O,NH); 11.55 (s,1H,exch.D₂O,NH).

EXAMPLE 30

5-(3,6-Dihydro-6-methyl-2-oxo-1,3,4-thiadiazin-5-yl)-1,3-dihydro-3,3,6-trimethyl-2H-indol-2-one

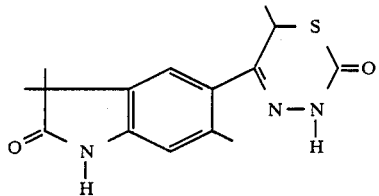
(E30)

Starting from 5-[(2-Bromo-1-oxo)propyl]-1,3-dihydro-3,3,6-trimethyl-2H-indol-2-one (D22b) and following the procedure of Example 29 afforded the desired compound.

m.p.=240° C.
IR (KBr)ν=3,200; 1,730; 1,660; 1,630; 1,205 cm⁻¹.
NMR (CDCl₃)δ=1.41 ppm (s,6H,CH₃); 1.58 (d,3H,J=7.2 Hz, CH₃); 2.40 (s,3H,CH₃Ar); 3.92 (q,1H,J=7.2 Hz,CH); 6.83 (s,1H, Ar); 7.09 (s,1H,Ar); 8.13 (s,1H,exch.D₂O,NH); 8.90 (s,1H, exch.D₂O,NH).

EXAMPLE 31

5-(3,6-Dihydro-6-methyl-2-oxo-2H-1,3,4-thiadiazin-5-yl)-1,3-dihydro-3,3,7-trimethyl-2H-indol-2-one

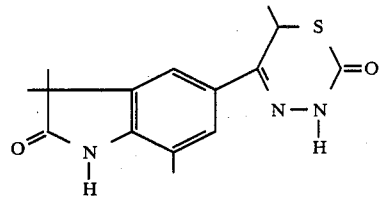
(E31)

Starting from 5-[(2-Bromo-1-oxo)propyl]-1,3-dihydro-3,3,7-trimethyl-2H-indol-2-one and following the procedure of Example 29 afforded the desired compound.

m.p.=260° C.
IR (KBr)ν=3,200; 1,710; 1,620; 1,220 cm⁻¹.
NMR (DMSO-d₆)δ=1.27 ppm (s,6H,CH₃); 1.47 (d,3H,J=7.1 Hz, CH₃); 2.26 (s,3H,CH₃,Ar); 4.71 (q,1H,J=7.1 Hz,CH); 7.48 (s,1H,Ar); 7.59 (s,1H,Ar); 10.65 (s,1H,exch.H₂O,NH); 11.57 (s,1H,exch.D₂O,NH).

EXAMPLE 32

1,3-Dihydro-5-(3,6-dihydro-6,6-dimethyl-2-oxo-2H-1,3,4-thiadiazin-5-yl)-3,3-dimethyl-2H-indol-2-one

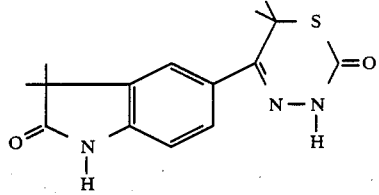
(E32)

A mixture of 2 g (6.45 mmol) 5-[(bromo-2-methyl-1-oxo)propyl]-1,3-dihydro-3,3-dimethyl-2H-indol-2-one(D24), 0.68 g (6.45 mmol) O-methylthiocarbazate, 0.84 g (6.50 mmol) diisopropyl ethylamine and 25 ml DMF were treated overnight at 80° C. The solvent was evapored under vacuum, the residue dissolved in 100 ml ethylacetate, washed twice with water, dried over MgSO4 and concentrated to dryness. The residue was purified by two successive chromatographies on silica (1st: isopropyl ether; 2nd: ethylacetate) to yield 0.040 g of the desired compound.

IR (KBr)ν=3,250; 1,700; 1,655; 1,620; 1,220 cm⁻¹.
NMR (CDCl₃)δ=1.43 ppm (s,6H,CH₃); 1.62 (s,6H,CH₃); 6.95 (d,1H,J=7.9 Hz,Ar); 7.3 (m;2H,Ar); 8.72 (s,1H,exch.D₂O,NH); 9.26 (s,1H,exch.D₂O,NH).

EXAMPLE 33

1,3-Dihydro-5-(3,6-dihydro-6-methyl-2-oxo-2H-1,3,4-thiadiazin-5-yl)-3-hydroxy-3-methyl-2H-indol-2-one

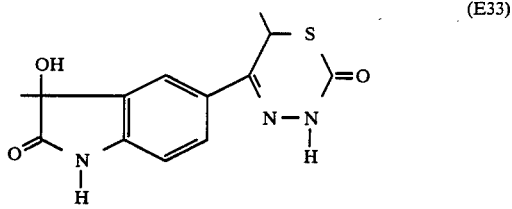
(E33)

1 g (3,6 mmol) 5-(3,6-dihydro-6-methyl-2-oxo-2H-1,3,4-thiadiazin-5-yl)-1H-indole-2,3 dione (Example 12) were dissolved under argon in 25 ml dry THF in a flame dried flask. 12 ml 3M methyl magnesium bromide in ether (10 eq) were added dropwise at 0°-5° C. The mixture was stirred overnight. 50 ml water were added, and extracted with ethyl acetate. The organic layers were washed with water and dried over magnesium sulfate. Purification by chromatography on silica (eluent:methylene chloride/ethyl acetate: 2/1), yielded 300 mg (28%) of the desired compound.

m.p.: 240° C. dec.

IR (KBr)$\nu$=3,200; 1,710; 1,645; 1,622; 1,495; 1,190 cm$^{-1}$.

NMR (DMSO-d$_6$)$\delta$=1.39 (s,3H,CH$_3$COH); 1.47 (d,J=7 Hz, 3H,CH$_3$CH); 4.71 (d,J=7 Hz,1H,CH$_3$CH); 6.00 (s,1H,exch.D$_2$O,OH); 6.88 (d,J=8 Hz,1H,Ar); 7.68 (m,1H,Ar); 7.78 (s,1H,Ar); 10.51 (s,1H,exch.D$_2$O,NH); 11.62 (s,1H,exch.D$_2$O,NH).

EXAMPLE 34

Ethyl 2,3-Dihydro-5-(3,6-dihydro-6-methyl-2-oxo-2H-1,3,4-thiadiazin-5-yl)-3,3-dimethyl-2-oxo-1H-indol-1-carboxylate

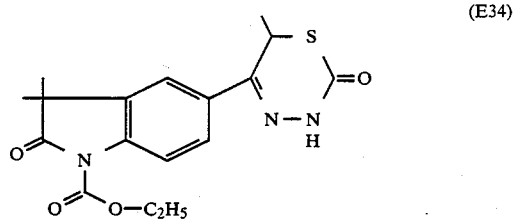
(E34)

1.16 g 5-(3,6-Dihydro-6-methyl-2-oxo-2H-1,3,4-thiadiazin-5-yl)-1,3-dihydro-3,3-dimethyl-2H-indol-2-one (Example 3) in 30 ml DMF were cooled to 0° C. 0.175 g sodium hydride from a 55% dispersion in mineral oil was added and the mixture was successively stirred for 0.5 hr at 0° C. and 0.5 hr at 20° C. After cooling to 0° C. a solution of 0.43 g ethyl chloroformate in 2 ml DMF was added dropwise. The reactional mixture was stirred at room temperature for 16 hrs, 250 ml ethyl acetate were added and the organic solution was washed with water. The aqueous phase was extracted with 2×100 ml methylene chloride and the organic solutions were mixed, dried on magnesium sulfate and evaporated to dryness. The residue was purified by chromatography on silica (methylene chloride-ethyl acetate: 4/1) then washed with isopropyl ether to yield 1.11 g of crystals.

m.p.: 246° C.

IR (KBr)$\nu$=3,260; 2,980; 2,930; 1,755; 1,735; 1,655; 1,620; 1,370; 1,300; 1,280 cm$^{-1}$.

NMR (CDCl$_3$)$\delta$=1.44-1.51 ppm (m,9H,CH$_3$); 1.69 (d,3H,J=7.3 Hz,CH$_3$); 4.30 (q,1H,J=7.3 Hz,CH); 4.50 (q,2H,J=7.1 Hz,CH$_2$); 7.59 (dd, 1H,J$_1$=2.0 Hz,J$_2$=8.6 Hz,Ar); 7.72 (d,1H,J=2.0 Hz,Ar); 7.99 (d,1H,J=8.6 Hz,Ar); 8.95 (s,1H,exch.D$_2$O,NH).

EXAMPLE 35

3,4-Dihydro-6-(3,6-dihydro-6-methyl-2-oxo-2H-1,3,4-thiadiazin-5-yl)-4,4-dimethyl-2(1H)-quinolinone

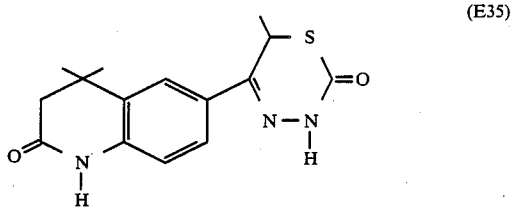
(E35)

2.14 g 6- (2-Bromo-1-oxo)-propyl -3,4-dihydro-4,4-dimethyl-2 (1H)-quinolinone, (D32), 0.732 g methoxy thiocarbonyl hydrazine and 40 ml acetonitrile were refluxed for 4 hrs. After 15 hrs at room temperature a precipitate was filtered off, washed with acetonitrile and dried to yield 1.25 g of the title compound.

m.p.: 288° C.

IR (KBr)$\nu$=3,170; 2,950; 1,675; 1,610; 1,510; 1,365; 1,240 cm$^{-1}$.

NMR (DMSO-d$_6$)$\delta$=1.31 ppm (s,6H,CH$_3$); 1.53 (d,3H,J=7.2 Hz,CH$_3$); 4.56 (q,1H,J=7.2 Hz,CH); 6.92 (d,1H, J=8.3 Hz,Ar); 7.54 (d,1H,J=8.3 Hz,Ar); 7.70 (s,1H,Ar); 10.21 (s,1H,exch.D$_2$O,NH); 11.31 (s,1H,exch.D$_2$O,NH).

EXAMPLE 36

3,4-Dihydro-6-(3,6-dihydro-6-methyl-2-oxo-2H-1,3,4-thiadiazin-5-yl)-3,3-dimethyl-2(1H)-quinolinone

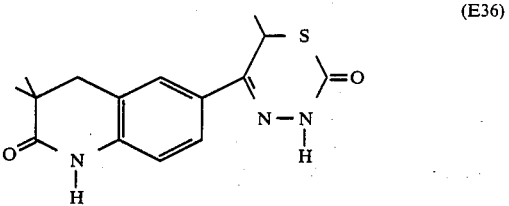
(E36)

1.9 g 6-]2-Bromo-1-oxo)propyl]-3,4-dihydro-3,3-dimethyl-2-(1H)-quinolinone (D31), 0.65 g methoxy thiocarbonyl hydrazine and 35 ml acetonitrile were refluxed for 12 hrs. After cooling to room temperature, the precipitate was filtered off, washed with 5 ml acetonitrile and dried to yield 0.6 g of crystals.

m.p.=245° C.

IR (KBr)$\nu$=3,250; 3,170; 3,050; 2,960; 1,670; 1,615; 1,510; 1,390; 1,245 cm$^{-1}$.

NMR (DMSO-d$_6$)$\delta$=1.10 ppm (s,6H,CH$_3$); 1.51 (d,3H,J=7.0 Hz, CH$_3$); 2.84 (s,2H,CH$_2$); 4.72 (q,1H,J=7.0 Hz,CH); 6.95 (d,1H,J=8.1 Hz,Ar); 7.65 (m,2H,Ar); 10.30 (s,1H,exch.D$_2$O, NH); 11.64 (s,1H,exch.D$_2$O,NH).

EXAMPLE 37

1,3-Dihydro-5-(1,2,3,6-tetrahydro-6-methyl-2-oxo-1,3,4-triazin-5-yl)-3,3-dimethyl-2H-indol-2-one

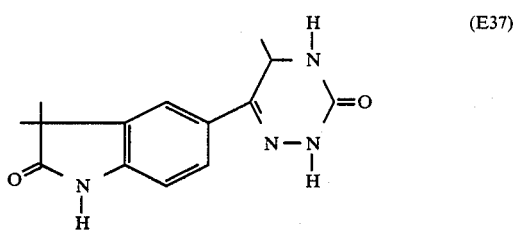
(E37)

6.3 g Ethyl 2-[2-(3,3-dimethyl-2-oxo-1H-indol-5-yl)-1-methyl-2-oxo-ethyl]-carbamate, (D28), 10.5 ml hydrazine hydrate, ml H₂O and 5 ml ethanol were mixed and heated to reflux under stirring for 16 hrs. After cooling to room temperature a precipitate was filtered off, washed with H₂O and dried. The crystals were washed with a diisopropyl ether-acetone mixture (15-1) and dried to yield 3.3 g of white crystals.

m.p.=292° C.

IR (KBr)$\nu$=3,570; 3,220; 3,100; 2,970; 1,720; 1,670; 1,620; 1,500; 1,440 cm⁻¹.

NMR (DMSO-d₆)$\delta$=1.19 ppm (d,3H,J=6.5 Hz,CH₃); 1.27 (s,6H,CH₃); 4.62 (q,1H,J=6.5 Hz,CH); 6.87 (d,1H,J=8.2 Hz,Ar); 7.44 (s,1H,exch.D₂O,NH); 7.53 (d,1H,J=8.2 Hz,Ar); 7.70 (s,1H,Ar); 9.92 (s,1H,exch.D₂O,NH); 10.51 (s,1H,exch.D₂O,NH).

EXAMPLE 38

1,3-Dihydro-5-(3,6-dihydro-6-methyl-2-oxo-2H-1,3,4-oxadiazin-5-yl)-3,3-dimethyl-2H-indol-2-one

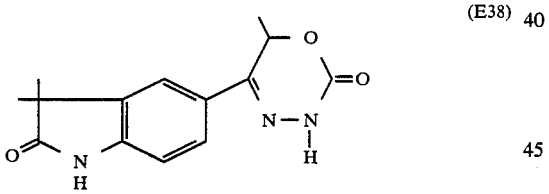
(E38)

A sodium ethylate solution prepared from 1.72 g sodium and ml ethanol was added dropwise to a suspension of 2.55 g ethyl 2-[1-(2-hydroxy-propyliden)-1-(3,3-dimethyl-2-oxo-1H-indol-5-yl)]hydrazinecarboxylate (D30) in 50 ml ethanol. At the end of the addition, the precipitate was dissolved and the resulting solution was stirred at room temperature for 3 hrs. The solvent was evaporated and the residue was taken up in 50 ml water acidified with 0.1N HCl. The precipitate was filtered off, washed with water and dried to yield 1.8 g of crystals.

m.p.=239° C.

IR (KBr)$\nu$=3,200; 3,100; 2,970; 2,930; 1,700; 1,635; 1,265 cm⁻¹.

NMR (DMSO-d₆)$\delta$=1.28 ppm (s,6H,CH₃); 1.43 (d,3H,J=6.9 Hz, CH₃); 5.76 (q,1H,J=6.9 Hz,CH); 6.91 (d,1H,J=8.2 Hz,Ar); 7.57 (d,1H,J=8.2 Hz,Ar); 7.72 (s,1H,Ar); 10.60 (s,IH,exch.D₂O,NH); 11.01 (s,1H,exch.D₂O,NH).

EXAMPLE 39

1,3 Dihydro-5-(3,6-dihydro-6-methyl-2-oxo-2H-1,3,4-thiadiazin-5-yl)-1-(3,4 dimethoxybenzoyl)-3,3-dimethyl-2H-indol-2-one

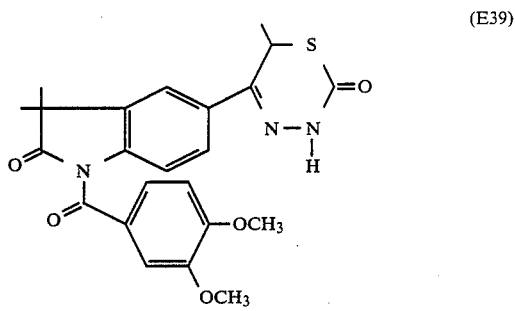
(E39)

Starting from 1,3-dihydro-5-(3,6-dihydro-6-methyl-2-oxo-2H-1,3,4-thiadiazin-5-yl)-3,3 dimethyl-2H-indol-2-one (Example 3) and following the method described in Example 23, but using 3,4-dimethoxy benzoyl chloride instead of isonicotinoyl chloride, afforded the desired compound.

Yield: 19%.

m.p.=218°–200° C.

IR (KBr)$\nu$=3,320; 2,970; 1,730; 1,715; 1,655; 1,625; 1,605; 1,518; 1,420; 1,270; 1,215; 1,160 cm⁻¹.

NMR (DMSO-d₆)$\delta$=1.27 and 1.29 ppm (2s,6H,2xCH₃); 1.75 (d,J=7.1 Hz,3H,CH₃-CH); 3.83 (s,3H,OCH₃); 3.87 (s,3H,OCH₃); 4.98 (q,J=7.1 Hz,1H,CH₃-CH); 6.97 (d,J=8.2 Hz,1H,Ar); 7.15 (d,J=8.5 Hz,1H,Ar); 7.41 (d,J=2.0 Hz,1H,Ar); 7.48 (dd,J₁=8.5 Hz,J₂=2.0 Hz,1H,Ar); 7.72 (dd,J₁=8.3 Hz,J₂=1.7 Hz,1H,Ar); 7.78 (s,1H,Ar); 10.70 (s,1H,exch.D₂O,NH).

EXAMPLE 40

Phenyl 2,3-dihydro-5-(3,6-dihydro-6-methyl-2-oxo-2H-1,3,4-thiadiazin-5-yl)-3,3-dimethyl-2-oxo-1H-indole-1-carboxylate

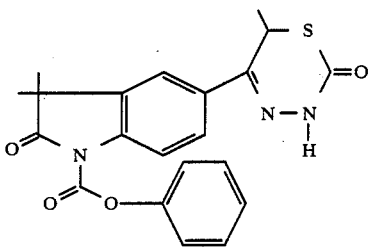
(E40)

1.0 g 5-(3,6-Dihydro-6-methyl-2-oxo-2H-1,3,4-thiadiazin-5-yl) -1,3-dihydro-3,3-dimethyl-2H-indol-2-one (Example 3) in 30 ml DMF was cooled at 0° C. 0.145 g sodium hydride from a 55% dispersion in mineral oil was added and the mixture was stirred at 0° C. for 0.5 hr, then 0.5 hr at 20° C. After cooling to 0° C. a solution of 0.582 g phenyl chloroformiate in 2 ml DMF was added dropwise. The reactional mixture was stirred at room temperature for 16 hrs and the solvent evaporated under vacuum. The oily residue was taken up in 250 ml methylene chloride, washed with water and dried on magnesium sulfate. The solvent was evaporated and the crude compound was purified by chromatography on silica (methylene chloride-ethyl acetate:9/1), then triturated in diethyl ether to yield 0.61 g of crystals.

m.p.=248° C.

IR (KBr)ν=3,400; 3,200; 3,080; 2,995; 2,930; 1,800; 1,760; 1,720; 1,630; 1,605 cm⁻¹.

NMR (CDCl₃)δ=1.55 ppm (s,6H,CH₃); 1.70 (d,3H,J=7.2 Hz,CH₃); 4.31 (q,1H,J=7.2 Hz,CH); 7.26–7.51 (m,5H,Ar); 7.61 (dd,1H,J₁=1.9 Hz,J₂=8.6 Hz,Ar); 7.77 (d,1H,J₁=1.9 Hz,Ar); 8.05 (d,1H,J₂=8.6 Hz,Ar); 8.91 (s,1H,exch.D₂O,NH).

EXAMPLE 41

5'-(3,6-Dihydro-6--methyl-2-oxo-2H-1,3,4-thiadiazin-5-yl)-1'-[(4-nitrophenyl)carbonyl]-spiro[cyclopentane-1,3'-[3H]indol]-2'(1'H)-one

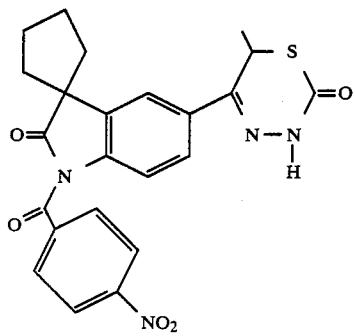
(E41)

Starting from 1',3'-dihydro-5'-(3,6-dihydro-6-methyl-2-oxo-2H-1,3,4-thiadiazin-5-yl)-spiro[cyclopentane-1,3'-2H-indol]-2(1'H)-one (Example 6) and 4-nitrobenzoyl chloride and following the procedure described in Example 23, the desired compound was obtained.

Yield: 41%.

m.p.=231°–3° C.

IR (KBr): ν=3,250; 2,950; 1,765; 1,680; 1,660; 1,618; 1,530; 1,345; 1,310 cm⁻¹.

NMR (CDCl₃): δ=1.71 ppm (d,J=7.3 Hz,3H,CH₃CH); 1.9–2.4 (m,8H,cyclopentane); 4.32 (q,7.3 Hz,1H,CH₃CH); 7.63 (dd,1H, J=1.9 Hz,J'=8.6 Hz,Ar); 7.80 (d,J=8.7 Hz,2H,ArNO₂); 7.79 (d, 1H,J=1.9 Hz,Ar); 8.07 (d,J'=8.6 Hz,1H,Ar); 8.33 (d,J=8.7 Hz, 2H,ArNO₂); 9.01 (s,1H,exch.D₂O,NH).

EXAMPLE 42

1,3-Dihydro-5-(3,6-dihydro-6-methyl-2-oxo-2H-1,3,4-thiadiazin-5-yl)-3,3-dimethyl-1-[(4-aminophenyl)carbonyl]-2H-indol-2-one

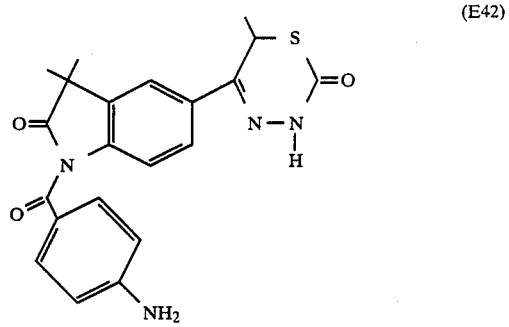
(E42)

A mixture of 2 g (4.56 mmol) 1,3-dihydro-5-(3,6-dihydro-6-methyl-2-oxo-2H-1,3,4-thiadiazin-5-yl)-3,3-dimethyl-1-(4-nitrobenzoyl)-2H-indol-2-one (Example 25), 5.15 g (115 mmol) tin (II) chloride, dihydrate in 50 ml ethanol was stirred 20 hrs at room temperature. The solution was concentrated, suspended in 50 ml ethyl acetate. 50 ml of a saturated solution of sodium hydrogenocarbonate were added. The mixture was filtered, decanted and the organic layer was washed with water, dried over magnesium sulfate and concentrated to 10 ml. The crystals were filtered, washed with ethyl acetate/hexane: 1/1 and dried under vacuum.

Yield: 75%.

m.p.=245° C.

IR (KBr): ν=3,370; 3,200; 1,745; 1,635; 1,605; 1,340; 1,270 cm⁻¹.

NMR (CDCl₃): δ=1.52 ppm (s,6H,2×CH₃); 1.69 (d,J=7.2 Hz, 3H,CH₃CH); 4.31 (q,J=7.2 Hz,1H,CH₃CH); 4.2–4.4 (m,2H,exch. D₂O,NH₂); 6.66 (d,J=8.7 Hz,1H,Ar); 7.57 (dd,J=8.7 Hz, J'=1.7 Hz,1H,Ar); 7.63 (d,J=4.4 Hz,2H,ArNH₂); 7.67 (d, J=4.4 Hz,2H,ArNH₂); 7.76 (d,J'=1.7 Hz,1H,Ar); 8.98 (s,1H, exch.D₂O,NH).

EXAMPLE 43

2,3-Dihydro-5-(3,6-dihydro-6-methyl-2-oxo-2H-1,3,4-thiadiazin-5-yl)-3,3-dimethyl-2-oxo-1H-indole-1-carboxamide

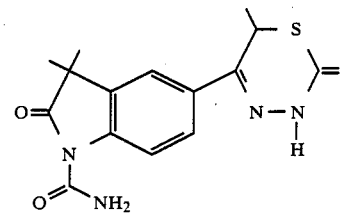
(E43)

1.45 g (5 mmol) 5-(3,6-dihydro-6-methyl-2-oxo-2H-1,3,4-thiadiazin-5-yl)-1,3-dihydro-3,3-dimethyl-2H-indol-2-one (Example 3) in 30 ml DMF were cooled to 0° C. 0.12 g (5 mmol) sodium hydride from a 55% dispension in mineral oil was added and the mixture was stirred for 0.5 hr at 0° C. then 0.5 hr at 20° C. After cooling to 0° C. a solution of 1 g trichloroacetyl isocyanate in 5 ml dry methylene chloride was added dropwise. The reactional mixture was stirred at room temperature overnight. The solvent was evaporated under vacuum, the residue taken up in 50 ml ethyl acetate and 40 g neutral aluminum oxide was added. The compound was then extracted from the aluminum oxide on a column with ethyl acetate. The solvent was evaporated and the residue was purified by chromatography on silica (eluent:methylene chloride/ethyl acetate: 2/1) to yield 0.37 g (22%) of the desired compound.

m.p.=192° C. (dec).

IR (KBr): $\nu$=3,400; 3,200; 1,750; 1,730; 1,645; 1,600; 1,475; 1,355; 1,310; 1,235 cm$^{-1}$.

NMR (DMSO-d$_6$): $\delta$=1.41 ppm (s,6H,C$\underline{H}_3$-C); 1.50 (d,J=7.0 Hz, C$\underline{H}_3$CH); 4.77 (q,1H,J=7.0 Hz,C$\underline{H}$-CH$_3$); 7.77 (dd,1H,J=8.0 Hz,J'=1.6 Hz,Ar); 7.88 (d,1H,J'=1.6 Hz,Ar); 7.95 (d,2H, exch.D$_2$O,NH$_2$); 8.15 (d,1H,J=8.0 Hz,Ar); 11.70 (s,1H, exch.D$_2$O,N$\underline{H}$).

EXANPLE 44

Ethyl 1,2,3-tetrahydro-6-(3,6-dihydro-6-methyl-2-oxo-2H-1,3,4-thiadiazin-5-yl)-4,4-dimethyl-2-oxo-1-quinoline carboxylate

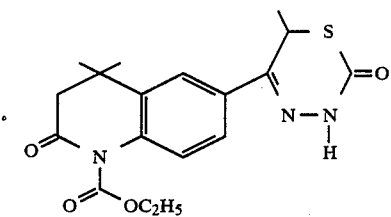

(E44)

0.70 g (2.3 mmol) 3,4-Dihydro-6-(3,6-dihydro-6-methyl-2-oxo-2H-1,3,4-thiadiazin-5yl)-4,4-dimethyl-2(1H)-quinoline (Example 35) in 17.2 ml DMP were cooled to 0° C. 0.055 g (2.3 mmol) sodium hydride from a 55% dispersion in mineral oil was added and the mixture was stirred for 0.5 hr at 0° C., then 0.5 hr at 20° C. After cooling to 0° C., a solution of 0.25 g (2.3 mmol) ethyl chloroformate in 1.5 ml DMF was added dropwise. The reactional mixture was stirred at room temperature overnight, 3 ml water were added and the solvent was evaporated. the residue was taken up in 80 ml methylene chloride, washed three times with water and dried over magnesium sulfate. The solvent was evaporated and the residue was triturated with a mixture of ethyl ether and ispropyl ether to yield 0.70 g (80%) of the desired compound.

m.p.=140° C.

IR (KBr): $\nu$=3,450; 2,900; 1,765; 1,685; 1,610; 1,515; 1,370; 1,240 cm$^{-1}$.

NMR (CDCl$_3$): $\delta$=1.38 ppm (S,6H, C$\underline{H}_3$-C); 1.43 (T, 3H, J=7.1 Hz, CH$_3$CH$_2$); 1.73 (d,3H, J=3.6 Hz,C$\underline{H}_3$-CH); 2.54 (s, 2H, C$\underline{H}_2$); 4.26 (S,1H, J=3.6 Hz, C$\underline{H}$CH$_3$); 4.46 (q,2H, J=7.1 Hz,C$\underline{H}_2$-CH$_3$); 6.92 (d,1H,J=8.3 Hz,AR); 7.57 (dd, 1H,J'=1.6 Hz, J=8.3 Hz,Ar); 7.84 (d,1H,J'=1.6 Hz,AR); 9.06 (s,1H, exch.D$_2$O, N$\underline{H}$).

EXAMPLE 45

5'-(3,6-Dihydro-6-methyl-2-oxo-2H-1,3,4-thiadiazin-5-yl)-spiro [imidazolidine-4,3'-[3H]indole]-2,2'(1'H),5-trione

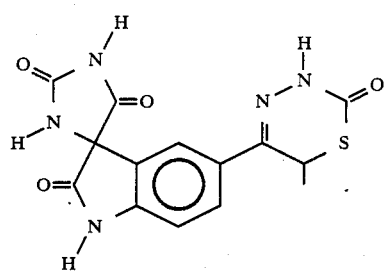

(E45)

A mixture of 1.1 g (4 mmol) 1,3-dihydro-5-(3,6-dihydro-6-methyl-2-oxo-2H-1,3,4-thiadiazin-5-yl)-3H-indole-2,3(1H)-dione, 0.32 g (5 mmol) potassium cyanide and 4.6 g (48 mmol) ammonium carbonate in 25 ml ethanol was heated at 50° C. for 4h30. After addition of 1 g charcoal the mixture was heated another hour. The suspension was filtered, the residue washed with hot water/ethanol and 100 ml water was added to the filtrate. This latter was extracted with 3×100 ml methylene chloride. The combined organic layers were washed with water, decolorized with charcoal. After concentration the residue was washed with chloroform/methanol: 9/1 to yield pure compound.

Yield: 45%. m.p.:>300° C.

IR (KBr): $\nu$=3,200 (large); 1,790; 1,730; 1,620; 1,500; 1,390; 1,210 cm$^{-1}$.

NMR (DMSO-d$_6$):$\delta$=1.45 ppm (d,J=6.9 Hz,3H,C$\underline{H}_3$-CH); 4.75 (m, 1H,CH$_3$C$\underline{H}$); 7.02 (d,J=8.2 Hz, 1H,Ar); 7.83 (m,2H,Ar); 8.63 (m,1H,exch.-D$_2$O,N$\underline{H}$); 11.24 (m,2H, exch.D$_2$O,N$\underline{H}$,N$\underline{H}$; 11.67 (m, 1H,exch.D$_2$O,N$\underline{H}$).

Pharmacological Data

1. Measurement of myofibrillar Ca++-dependent Mg++ATPase activity the effect on myofibrillar Ca++sensitivity and on maximal activity of myofibrillar Ca++-dependent Mg++-ATPase was determined on canine cardiac myofibrils.

(a) Contractile protein preparation

Cardiac myofibrils free of membrane contaminants were prepared from left ventricular tissue of dog hearts using a modification of the method described by SOLARO et al, Biochem. Biophys. Acta, 245, 259–262, (1971). Before centrifugration, the heart homogenate was filtered through gauze.

After Triton X-100 treatments, the myofibrillar fraction was washed once by resuspension and centrifugation in 10 volumes of 1 mM EGTA, 60 ml KCl, 30 mM imidazole, 2 mM MgCl$_2$, pH 7.0. The pellet was then washed three times in 10 volumes of the same buffer without EGTA. Before the last centrifugation, the suspension of myofibrils was filtered through a stainless steel sieve with 0.25 mm meshes.

Myofibrils were kept in pellet overnight. Before use, the pellet was suspended in a small amount of buffer, the protein concentration was determined by the method of BRADFORD M., Anal. Biochem., 1976, 72, 248 and adjusted in order to have a concentration between 6 and 7 mg/ml.

(b) Myofibrillar ATPase activity

Ca++-dependent myfibrillar ATPase activity was determined at 21° C., pH 7.0, by measuring the rate of release of inorganic phosphate. All assays were performed within 24 hrs. of final purification, using the method described by SOLARO and RUEGG, CIRC. RES., 51, 290-4, (1982). Reaction mixtures (4 ml) containing 0.6-0.7 mg/ml myofibrillar protein, 80 mM KCl, 20 mM imidazole, 3 mM $MgCl_3$, 1 mM EGTA, the desired amount of $CaCl_2$, and the indicated concentration of drug or appropriate vehicle were preincubated for 6 min. prior to assay. The amount of $CaCl_2$ was varied between 0 and 0.9 mM and the pCA (-log free Ca++) computed using $2.514 \times 10^6 M^{-1}$ as the apparent affinity of Ca++ for EGTA at pH 7.0.

Reactions were initiated by the addition of $Na_2ATP$ to final concentration of 2 mM. After an incubation period of 12 min., reactions were quenched by the addition of an equal volume of ice-cold 10% trichloroacetic acid. The protein was pelleted by centrifugation (2000 g, 15 min.) and Pi was assayed in the supernatant fraction using a modification of the method described by LANZETTA et al, Anal. Biochem., 100, 95-97, (1979).

The following solutions were prepared:
(1) 3.7% ammonium heptamolybdate in 0.12N $H_2SO_4$
(2) 0.074% malachite green oxalate in 1% polyvinylic alcohol.

the colour reagent was prepared by mixing an equal volume of solution (1) and (2) 15 min. before the assay. For the assay, 1700 μl of 1% $H_2SO_4$ and 1 ml of colour reagent were added to 100 μl of sample. Colour development occurred at room temperature for 30 min. and was quenched by the addition of 200 μl of 1M tri-potassium citrate. The absorbance was measured at 620 millimicrons.

The effect of each compound, tested at the indicated concentration, on the relation between pCa and percent activation was determined taking 100% for the maximum ATPase activity obtained with vehicle alone. The effect on Ca++ sensitivity was quantified by measuring the shift of the pCa giving 50% of the maximal control ATPase activity.

The effect on maximal ATPase activity was expressed as the percent change of ATPase activity for pCa=5.47.

| Results Canine cardiac myofibrillar $Ca^{++}$-dependent $Mg^{++}$ ATPase. | | | |
|---|---|---|---|
| Example No. | Concentration ($\times 10^{-5}$ molar) | $Ca^{2+}$ sensitivity p $CA_{50}$ | Max ATPase activity (%) |
| 1 | 20 | 0.38 ± 0.03 | −3 ± 2 |
| 2 | 20 | 0.16 ± 0.07 | −9 ± 2 |
| 3 | 20 | 0.32 ± 0.06 | −12 ± 2 |
| 4 | 20 | 0.15 ± 0.03 | −6 ± 2 |
| 5 | 20 | 0.40 ± 0.08 | −8 ± 1 |
| 7 | 20 | 0.37 ± 0.06 | −2 ± 3 |
| 10 | 3 | 0.36 ± 0.02 | −9 ± 5 |
| 11 | 20 | 0.36 ± 0.05 | +1 ± 0 |
| 13 | 3 | 0.58 ± 0.04 | −11 ± 5 |
| 14 | 3 | 0.71 ± 0.09 | +4 ± 1 |
| 15 | 3 | 0.37 ± 0.11 | −4 ± 1 |
| 17 | 3 | 0.41 ± 0.07 | −17 ± 4 |
| 18 | 3 | 0.19 ± 0.03 | +3 ± 3 |
| 20 | 3 | 0.21 ± 0.05 | −5 ± 3 |
| 21 | 1 | 0.46 ± 0.04 | −7 ± 2 |
| 27 | 3 | 0.47 ± 0.10 | +2 ± 5 |
| 35 | 3 | 0.45 ± 0.05 | −1 ± 2 |
| 36 | 3 | 0.33 ± 0.07 | −4 ± 3 |
| 40 | 3 | 0.15 ± 0.01 | +2 ± 2 |
| 42 | 3 | 0.17 ± 0.03 | −9 ± 2 |

Cardiotonic activity in the conscious instrumented Dog

Male Beagle dogs, at least 2 years old, weighing 12 to 18 kg were anaesthetised with pentobarbital sodium (30 mg/kg i.v.). Respiration was maintained by a Harward pump, model 613a. The heart was exposed through a left thoracotomy and a pericardial cardle was formed. A high fidelity micromanometer (Koenigsberg $P_5$–$P_7$) was inserted into left venitricular lumen through a stab incision at the apex. Wires were exteriorised to the back of the animals, placed into a size adapted jacket, and the chest closed. The experiments were conducted on the conscious dogs, 1 or 2 weeks after the surgery, when the animals had completely recovered.

Measured parameters were : first derivative of left ventricular pressure, (dP/dt, mmHg/sec); heart rate (HR, beats/min.). A control period recording of 90 min. was made with the dogs placed in a quiet room, the recordings being made outside. Compounds to be tested were administered orally in gelatin capsules and the parameters measured for 5 hrs. at least.

Results were expressed as the percentage of the maximum±SEM.

| Results Conscious Dog | | | |
|---|---|---|---|
| Example No. | Dose (mg/kg p.o.) | H.R. | dP/dt Max |
| 1 | 0.30 | +17 ± 5 | +53 ± 6 |
| 3 | 0.03 | +8 ± 5 | +71 ± 3 |
| 5 | 0.03 | +16 ± 8 | +45 ± 5 |
| 6 | 0.30 | +7 ± 4 | +33 ± 3 |
| 7 | 0.01 | +9 ± 4 | +41 ± 5 |
| 9 | 10.00 | +16 ± 8 | +68 ± 14 |
| 11 | 3.00 | +7 ± 4 | +51 ± 14 |
| 12 | 0.30 | +10 ± 4 | +51 ± 14 |
| 13 | 0.30 | +15 ± 4 | +43 ± 4 |
| 14 | 0.30 | +22 ± 15 | +30 ± 8 |
| 16 | 0.03 | +21 ± 4 | +105 ± 14 |
| 17 | 3.00 | +9 ± 6 | +40 ± 11 |
| 18 | 0.30 | +28 ± 7 | +74 ± 7 |
| 20 | 3.00 | +8 | +45 |
| 21 | 0.30 | +9 ± 6 | +42 ± 4 |
| 22 | 0.03 | +14 ± 5 | +56 ± 5 |
| 27 | 1.00 | +15 ± 2 | +63 ± 9 |
| 35 | 0.10 | +20 ± 5 | +49 ± 9 |
| 36 | 0.10 | +7 ± 3 | +46 ± 10 |
| 37 | 0.03 | +24 ± 8 | +85 ± 8 |

We claim:

1. A compound of formula (I), or a pharmaceutically acceptable salt thereof,

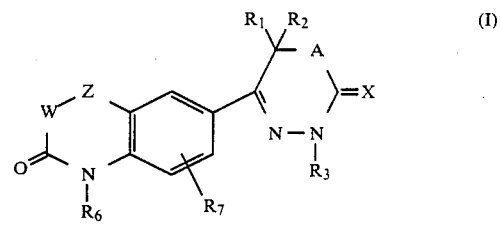

in which, $R_1$ is hydrogen, lower alkyl or $CH_2OR_6$; $R_2$ is hydrogen or lower alkyl; $R_3$ is hydrogen or lower alkyl;

each of W and Z, which are different, is —CR$_4$R$_5$— or —(CR$_x$R$_y$)$_n$—, in which, R$_4$ is hydrogen, alkyl of 1 to 3 carbon atoms, alkylthio of 1 to 3 carbon atoms or alkoxy of 1 to 3 carbon atoms; R$_5$ is alkyl of 1 to 3 carbon atoms, alkylthio of 1 to 3 carbon atoms or alkoxy of 1 to 3 carbon atoms; or R$_4$ and R$_5$ together with the carbon atom to which they are attached form a 3- to 6-membered carboxylic ring, or a 3- to 6-membered heterocyclic ring containing one or two ring oxygen, nitrogen or sulphur atoms; or R$_4$ and R$_5$ together form an oxo or methylene moiety; each of R$_x$ and R$_y$ is hydrogen or alkyl of 1 to 3 carbon atoms; n is zero or 1; R$_6$ is hydrogen, lower alkyl, lower alkylcarbonyl, arylcarbonyl, aralkylcarbonyl, heteroarylcarbonyl, aminocarbonyl, lower alkoxycarbonyl or aryloxycarbonyl wherein the aryl moiety is a carbocyclic aromatic moiety of 6 to 12 carbon atoms, the aralkyl moiety is a carbocyclic aromatic moiety of 6 to 12 carbon atoms linked to an alkylene moiety of 1 to 6 carbon atoms which alkylene moiety is unsubstituted or itself substituted by a carbocyclic aromatic moiety of 6 to 12 carbon atoms, and the heteroaryl moiety is a ring system of 5 to 12 ring atoms having up to 4 heteroatoms selected from the group consisting of oxygen, nitrogen and sulphur; R$_7$ is hydrogen or lower alkyl; X is oxygen or sulphur; and A is sulphur, oxygen or —Nh—.

2. A compound according to claim 1, in which n is zero.

3. A compound according to claim 1, in which A is sulphur.

4. A compound according to claim 1, in which X is oxygen.

5. A compound according to claim 1 in which R$_4$ is methyl and R$_5$ is methyl or thiomethyl, or R$_4$ and R$_5$ together with the carbon atom to which they are attached form a cyclopropyl, cyclopentyl, cyclohexyl, ethylenedithio, propylenedithio or propylenethio moiety.

6. A compound according to claim 1 selected from the group consisting of:
1,3-Dihydro-5-(3,6-dihydro-2-oxo-2H-1,3,4-thiadiazin-5-yl)-3-methyl-3-methylthio-2H-indol-2-one;
1,3-dihydro-5-(3,6-dihydro-2-oxo-2H-1,3,4-thiadiazin-5-yl)-3,3-dimethyl-2H-indol-2-one;
1,3-Dihydro-5-(3,6-dihydro-6-methyl-2-oxo-2H-1,3,4-thiadiazin-5-yl)-3,3-dimethyl-2H-indol-2-one;
1,3-Dihydro-5-(3,6-dihydro-2-oxo-2H-1,3,4-thiadiazin-5-yl)-3-methyl-2H-indol-2-one;
1,3-Dihydro-5-(3,6-dihydro-6-methyl-2-oxo-2H-1,3,4-thaidiazin-5-yl)-3-methyl-3-methylthio-2H-indol-2-one;
5'-(3,6-Dihydro-6-methyl-2-oxo-2H-1,3,4-thiadiazin-5-yl)-spiro[cyclopentane-1,3'-[3H]-indol]-2'(1'H)-one
1-Acetyl-1,3-dihydro-5-(3,6-dihydro-6-methyl-2-oxo-2H-1,3,4-thiadiazin-5-yl)-3,3-dimethyl-2H-indol-2-one;
1-Acetyl-1,3-dihydro-5-(3,6-dihydro-2-oxo-2H-1,3,4-thiadiazin-5-yl)-3-methyl-2H-indol-2-one
1-Acetyl-1,3-dihydro-5-(3,6-dihydro-2-oxo-2H-1,3,4-thiadiazin-5-yl)-3-methyl-3-methylthio-2H-indol-2-one
1,3-Dihydro-5-)3,6-dihydro-6-methyl-2-oxo-2H-1,3,4-thiadiazin-5-yl)-3-methylthio-2H-indol-2-one
1,3-Dihydro-5-(3,6-dihydro-2-oxo-2H-1,3,4-thiadiazin-5-yl)-3-methylthio-2H-indol-2-one
5-(3,6-Dihydro-6-methyl-2-oxo-2H-1,3,4-thaidiazin-5-yl)-1H-indole-2,3-dione
5'-(3,6-Dihydro-6-methyl-2-oxo-2H-1,3,4-thiadiazin-5-yl)-spiro[1,3-dithiolane-2,3'-[3H]indol]-2(1'H)-one
5'-(3,6-Dihydro-6-methyl-2-oxo-2H-1,3,4-thiadiazin-5-yl)-spiro[1,3-dithiane-2,3'-[3H]indol]-2'-(1'H)-one
1,3-Dihydro-5-(3,6-dihydro-6-methyl-2-oxo-2H-1,3,4-thiadiazin-5-yl)-3,3-di (methylthio)-2H-indol-2-one
5'-(3,6-Dihydro-6-methyl-2-oxo-2H-1,3,4-thiadiazin-5-yl)-spiro[cyclopropane-1,3'-[3H]indol]-2'-(1'H)-one;
5'-(3,6-Dihydro-6-methyl-2-oxo-2H-1,3,4-thiadiazin-5yl)-spiro [cyclohexane-1,3'-[3H]indol]-2'-(1'H)-one
1,3-Dihydro-5-(3,6-dihydro-6-methyl-2-oxo-2H-1,3,4-thiadiazine-5-yl)-1,3,3-trimethyl-2H-indol-2-one
5'-(3,6-Dihydro-3,6-dimethyl-2-oxo-2H-1, 3,4-thiadiazin-5-yl)-1'-methyl-spiro[cyclopentane-1,3'-[3H]indol]-2'(1'H)-one
5'-(3,6-Dihydro-2-oxo-2H-1,3,4-thiadiazin-5-yl)-spiro[thiolane-2,3'-[3H]indol]-2'(1'H)-one
5'-(3,6-Dihydro-6-methyl-2-oxo-2H-1,3,4-thiadiazin-5-yl)-spiro [thiolane-2,3'-[2,3'-[3H]-indol]-2'(1'H)-one
1-Benzoyl-1,3-dihydro-5-(3,6-dihydro-6-methyl-2-oxo-2H-1,3,4-thiadiazin-5-yl)-3,3-dimethyl-2H-indol-2-one
1,3-Dihydro-5-(3,6-dihydro-6-methyl-2-oxo-2H-1,3,4-thiadiazin-5-yl)-3,3-dimethyl-1-[4-pyridyl)carbonyl]-2H-indol-2-one
1,3-Dihydro-5-(3,6-dihydro-6-methyl-2-oxo-2H-1,3,4-thiadiazin-5-yl)-3,3-dimethyl-1-[(3-pyridyl)carbonyl]-2H-indol-2-one
1,3-Dihydro-5-(3,6-dihydro-6-methyl-2-oxo-2H-1,3,4-thiadiazin-5-yl)-3,3-dimethyl-1-(4-nitrobenzoyl)-2H-indol-2-one
1,3-Dihydro-5-(3,6-dihydro-6-methyl-2-oxo-2H-1,3,4-thiadiazin-5-yl)-3,3-dimethyl-1-(phenylmethyl carbonyl)-2H-indol-2-one
5'-(3,6-Dihydro-6-methyl-2-oxo-2H-1,3,4-thiadiazin-5-yl(1'-[(4-pyridyl)carbonyl]-spiro[cyclopentane-1,3'-[3H]indol]-2'(1'H)-one
1-[2,3-Dihydro-5-(3,6-dihydro-6-methyl-2-oxo-2H-1,3,4-thiadiazin-5-yl)-3,3-dimethyl-2-oxo-1H-indol-1-yl]-2,4-diphenyl-1,3 butanedione
1,3-Dihydro-5-(3,6-dihydro-6-methyl-2-oxo-2H-1,3,4-thiadiazin-5-yl)-3,3,4-trimethyl-2H-indol-2-one
1,3-Dihydro-5-(3,6-dihydro-6-methyl-2-oxo-2H-1,3,4-thiadiazin-5-yl)-3,3,6-triamethyl-2H-indol-2-one
1,3-Dihydro-5-(3,6-dihydro-6-methyl-2-oxo-2H-1,3,4-thiadiazin-5-yl)-3,3,7-trimethyl-2H-indol-2-one
1,3-Dihydro-5-(3,6-dihydro-6,6-dimethyl-2-oxo-2H-1,3,4-thiadiazin-5-yl)-3,3-dimethyl-2H-indol-2-one
1,3-Dihydro-5-(3,6-dihydro-6-methyl-2-oxo-2H-1,3,4-thiadiazin-5-yl)-3-hydroxy-3-methyl-2H-indol-2-one
Ethyl 2,3-dihydro-5-(3,6-dihydro-6-methyl-2-oxo-2H-1,3,4-thiadiazin-5-yl)-3,3-dimethyl-2-oxo-1H-indol-1-carboxylate
1,3-Dihydro-5-(1,2,3-6-tetrahydro-6-methyl- 2-oxo-1,3,4-triazin-5-yl)-3,3-dimethyl-2H-indol- 2-one
1,3-Dihydro-5-(3,6-dihydro-6-methyl-2-oxo-2H- 1,3,4-oxadiazin 5-yl)-3,3-dimethyl-2H-indol-2-one
1,3-Dihydro-5-(3,6-dihydro-6-methyl-2-oxo-2H-1,3,4-thiadiazin-5-yl)-1-(3,4-dimethoxybenzoyl)-3,3-dimethyl-2H-indol-2-one
Phenyl 2,3-dihydro-5-(3,6-dihydro-6-methyl-2- oxo-2H-1,3,4-thiadiazin-5-yl)-3,3-dimethyl-2-oxo-1H-indole-1-carboxylate
3,4-Dihydro-6-(3,6-dihydro-6-methyl-2-oxo-2H-1,3,4-thiadiazin-5-yl)-4,4-dimethyl-2(1H-quinolinone
3,4-Dihydro-6-(3,6-dihydro-6-methyl-2-oxo-2H- 1,3,4-thiadiazin-5-yl)-3,3-dimethyl-2(1H)-quinolinone 5'-(3,6-Dihydro-6-methyl-2-oxo-2H-1,3,4-thiadiazin-5-yl)-1'](4-nitrophenylcarbonyl]-spiro[cyclopentane-1,3'-[3H]indol]-2'(1H)-one 1,3-Dihydro-5-(3,6-dihydro-6-methyl-2-oxo-2H-1,3,4-thiadiazin-5-yl)-3,3-dimethyl-1-[4-aminophenyl)carbonyl]-2-H-indol-2-one 2,3-Dihydro-5-(3,6-dihydro-6-methyl-2-oxo-2H-1,3,4-thiadiazin-5-yl)-3,3-dimethyl-2-oxo-1H-indole-1-carboxamide Ethyl 1,2,3,4-tetrahydro-6-(3,6-dihydro-6-methyl-2-oxo-2H-1,3,4-thiadiazin-5-yl)-4,4-dimethyl-2-oxo-1-quinoline carboxylate 5'-(3,6-Dihydro-6-methyl-2-oxo-2H-1,3,4-thiadiazin-5-yl)-spiro-[imidazolidine-4,3'-[3H]indole]-2,2'-(1'H), 5-trione.

7. A pharmaceutical composition useful for treating heart disease and asthmatic conditions in mammals which comprises a therapeutically effective amount of a compound of the formula (I):

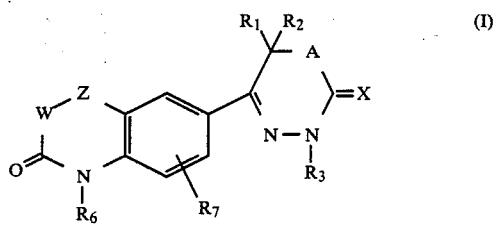

in which, $R_1$ is hydrogen, lower alkyl or $CH_2OR_6$; $R_2$ is hydrogen or lower alkyl; $R_3$ is hydrogen or lower alkyl; each of W and Z, which are different, is $-CR_4R_5-$ or $-(CR_xR_y)_n-$, in which, $R_4$ is hydrogen, alkyl of 1 to 3 carbon atoms, alkylthio of 1 to 3 carbon atoms or alkoxy of 1 to 3 carbon atoms; $R_5$ is alkyl of 1 to 3 carbon atoms, alkylthio of 1 to 3 carbon atoms or alkoxy of 1 to 3 carbon atoms; or $R_4$ and $R_5$ together with the carbon atom to which they are attached form a 3- to 6-membered carbocyclic ring, or a 3- to 6-membered heterocyclic ring containing one or two ring oxygen, nitrogen or sulphur atoms; or $R_4$ and $R_5$ together form an oxo or methylene moiety; each of $R_x$ and $R_y$ is hydrogen or alkyl or 1 to 3 carbon atoms; n is zero or 1; $R_6$ is hydrogen, lower alkyl, lower alkylcarbonyl, arylcarbonyl, aralkylcarbonyl, heteroarylcarbonyl, aminocarbonyl, lower alkoxycarbonyl or aryloxycarbonyl wherein the aryl moiety is a carbocyclic aromatic moiety of 6 to 12 carbon atoms, the aralkyl moiety is a carbocyclic aromatic moiety of 6 to 12 carbon atoms linked to an alkylene moiety of 1 to 6 carbon atoms which alkylene moiety is unsubstituted or itself substituted by a carbocyclic aromatic moiety of 6 to 12 carbon atoms, and the heteroaryl moiety is a ring system of 5 to 12 ring atoms having up to 4 heteroatoms selected from the group consisting of oxygen, nitrogen and sulphur; $R_7$ is hydrogen or lower alkyl; X is oxygen or sulphur: and A is sulphur, oxygen or $-NH-$, in combination with a pharmaceutically acceptable carrier.

8. A composition according to claim 7, in which n is zero.

9. A composition according to claim 7, in which A is sulphur.

10. A composition according to claim 7, in which X is oxygen.

11. A composition according to claim 7, in which $R_4$ is methyl and $R_5$ is methyl or thiomethyl, or $R_4$ and $R_5$ together with the carbon atom to which they are attached form a cyclopropyl, cyclopentyl, cyclohexyl, ethylenedithio, propylenedithio or propylenethio moiety.

12. A composition according to claim 7, wherein the compound is selected from the group consisting of:
1,3-dihydro-5-(3,6-dihydro-2-oxo-2H-1,3,4-thiadiazin-5-yl)-3-methyl-3-methylthio-2H-indol-2-one;
1,3-dihydro-5-(3,6-dihydro-2-oxo-2H-1,3,4-thiadiazin-5-yl)-3,3-dimethyl-2H-indol-2-one;
1,3-dihydro-5-(3,6-dihydro-6-methyl-2-oxo-2H-1,3,4-thiadiazin-5-yl)-3,3-dimethyl-2H-indol-2-one;
1,3-dihydro-5-(3,6-dihydro-2-oxo-2H-1,3,4,-thiadiazin-5- yl)-3-methyl-2H-indol-2-one;
1,3-dihydro-5-(3,6-dihydro-6-methyl-2-oxo-2H-1,3,4-thiadiazin--5-yl)-3-methyl-3-methylthio-2H-indol-2-one;
5'-(3,6-dihydro-6-methyl-2-oxo-2H-1,3,4-thiadiazin-5-yl)-spiro[cyclopentane-1,3,'-[3H]-indol]-2'(1'H)-one;
1-acetyl-1,3-dihydro-5-(3,6-dihydro-6-methyl-2- oxo-2H-1,3,4-thiadiazin-5-yl)-3,3-dimethyl-2H-indol-2-one;
1-Acetyl-1,3-dihydro-5-(3,6-dihydro-2-oxo-2H- 1,3,4-thiadiazin-5-yl)-3-methyl-2H-indol-2-one;
1-Acetyl-1,3-dihydro-5-(3,6-dihydro-2-oxo-2H-1,3,4-thiadiazin-5-yl)-3-methyl-3-methylthio-2H-indol-2-one
1,3-Dihydro-5-(3,6-dihydro-6-methyl-2-oxo-2H-1,3,4-thaidiazin-5-yl)-3-methylthio-2H-indol-2-one
1,3-Dihydro-5-(3,6-dihydro-2-oxo-2H-1,3,4-thiadiazin-5-yl)-3-methylthio-2H-indol-2-one
5-(3,6-Dihydro-6-methyl-2-oxo-2H-1,3,4-thiadiazin-5-yl)1H-indole-2,3-dione
5'-(3,6-Dihydro-6-methyl-2-oxo-2H-1,3,4-thiadiazin-5-yl)-spiro[1,3-dithiolane-2,3'-[3H]indol]-2(1'H)-one
5'-(3,6-Dihydro-6-methyl-2-oxo-2H-1,3,4-thiadiazin-5-yl)-spiro[1,3-dithiane-2,3'-[3H]indol-2'(1'H)-one
1,3-Dihydro-5-(3,6-dihydro-6-methyl-2-oxo-2H-1,3,4-thiadiazin-5-yl)-3,3-di(methylthio)-2H-indol-2-one
5-(3,6-Dihydro-6-methyl-2-oxo-2H-1,3,4-thiadiazin-5-yl)-spiro[cyclopropane-1,3'-[3H]indol]-2'-(1'H)-one
5'-(3,6-Dihydro-6-methyl-2-oxo-2H-1,3,4-thiadiazin-5-yl)-spiro[cyclohexane-1,3'-[3H]indol]-2'-(1'H)-one
1,3-Dihydro-5-(3,6-dihydro-6-methyl-2-oxo-2H-1,3,4-thiadiazin-5-yl)-1,3,3-triemthyl-2H-indol-2-one
5'- (3,6-dihydro-3,6-dimethyl-2-oxo-2H-1,3,4-thiadiazin-5-yl)-1'-methyl-spiro[cyclopentane-1,3'-[3H]indol]-2'(1'H)-one
5'-(3,6-Dihydro-2-oxo-2H-1,3,4-thiadiazin-5-yl)-spiro[thiolane-2,3'-[3H]-indol]-2'(1'H)-one
5'-(3,6-Dihydro-6-methyl-2-oxo-2H-1,3,4-thiadiazin-5-yl)-spiro[thiolane-2,3'-[3H]-indol]-2'(1'H)-one
1-Benzoyl-1,3-dihydro-5-(3,6-dihydro-6-methyl-2-oxo-2H-1,3,4-thiadiazin-5-yl)-3,3-dimethyl-2H-indol-2-one
1,3-Dihydro-5-(3,6-dihydro-6-methyl-2-oxo-2H-1,3,4-thiadiazin-5-yl)-3,3-dimethyl-1-[(4-pyridyl)carbonyl-2H-indol]-2-one
1,3-Dihydro-5-(3,6-dihydro-6-methyl-2-oxo-2H-1,3,4-thiadiazin-5-yl)-3,3-dimethyl-1-[(3-pyridyl)carbonyl]-2H-indol-2-one
1,3-Dihydro-5-(3,6-dihydro-6-methyl-2-oxo-2H-1,3,4-thiadiazin-5-yl)-3,3-dimethyl-1-(4-nitrobenzoyl)-2H-indol-2-one
1,3-Dihydro-5-(3,6-dihydro-6-methyl-2-oxo-2H-1,3,4-thiadiazin-5-yl)-3,3-dimethyl-1-(phenylmethylcarbonyl)-2H-indol-2-one 5'-(3,6-Dihydro-6-methyl-2-oxo-2H-1,3,4-thiadiazin-5-yl-1'-[(4-pyridyl)carbonyl]-spiro[cyclopentane-1,3'-[3H]-indol]-2'(1H)-one 1-[2,3-Dihydro-5-(3,6-dihydro-6-methyl-2-oxo-2H-1,3,4-thiadiazin-5-yl)-3,3-dimethyl-2-oxo-1H-indol-1-yl]-2,4-diphenyl-1,3-butanedione 1,3-Dihydro-5-(3,6-dihydro-6-methyl-2-oxo-2H-1,3,4-thiadiazin-5-yl)-3,3,4-trimethyl-2H-indol-2-one 1,3-Dihydro-5-(3,6-dihydro-6-methyl-2-oxo-2H-1,3,4-thiadiazin-5-yl)-3,3,6-trimethyl-2H-indol-2-one 1,3-Dihydro-5-(3,6-dihydro-6-methyl-2-oxo-2H-1,3,4-thiadiazin-5-yl)-3,3,7-trimethyl-2H-indol-2-one 1,3-Dihydro-5-(3,6-dihydro-6,6-dimethyl-2-oxo-2H-1,3,4-thiadiazin-5-yl)-3,3-dimethyl-2H-indol-2-one 1,3-Dihydro-5-(3,6-dihydro-6-methyl-2-oxo-2H-1,3,4-thiadiazin-5-yl)-3-hydroxy-3-methyl-2H-indol-2-one Ethyl 2,3-dihydro-5-(3,6-dihydro-6-methyl-2-oxo-2H-1,3,4-thiadiazin-5-yl)-3,3-dimethyl-2-oxo-1H-indol-1-carboxylate 1,3-Dihydro-5-(1,2,3,6-tetrahydro-6-methyl-2-oxo-1,3,4-triazin-5-yl)-3,3-dimethyl-2H-indol-2-one 1,3-Dihydro-5-(3,6-dihydro-6-methyl-2-oxo-2H-1,3,4-oxadiazin-5-yl)-3,3-dimethyl-2H-indol-2-one 1,3-Dihydro-5-(3,6-dihydro-6-methyl-2-oxo-2H-2,3,4-thiadiazin-5-yl)-1-(3,4-dimethoxybenzoyl)-3,3-dimethyl-2H-indol-2-one Phenyl 2,3-dihydro-5-(3,6-dihydro-6-methyl-2-oxo-2H-1,3,4-thiadiazin-5-yl)-3,3-dimethyl-2-oxo-1H-indole-1-carboxylate 3,4-Dihydro-6-(3,6-dihydro-6-methyl-2-oxo-2H-1,3,4-thiadiazin-5-yl)-4,4-dimethyl-2(1H)-quinolinone 3,4-Dihydro-6-(3,6-dihydro-6-methyl-2-oxo-2H-1,3,4-thiadiazin-5-yl)-3,3-dimethyl-2(1H)-quinolione 5'-(3,6-Dihydro-6-methyl-2-oxo-2H-1,3,4-thiadiazin-5-yl)-1'[(4-nitrophenyl)carbonyl]-spiro[cyclopentane-1,3'-[3H]indol]-2'(1'H)-one 1,3-Dihydro-5-(3,6-dihydro-6-methyl-2-oxo-2H1,3,4-thiadiazin-5-yl)-3,3-dimethyl-1-[4-aminophenyl)carbonyl-2H-indol-2-one 2,3-Dihydro-5-(3,6-Dihydro-6-methyl-2-oxo-2H-1,3,4-thiadiazin-5-yl)-3,3-dimethyl-2-oxo-1H-indol-1-carboxamide Ethyl 1,2,3,4-tetrahydro-6-(3,6-dihydro-6-methyl-2-oxo-2H-1,3,4-thiadiazin-5-yl)-4,4-dimethyl-2-oxo-1-quinoline carboxylate and 5'-(3,6-Dihydro-6-methyl-2-oxo-2H-1,3,4-thiadiazin-5-yl)-spiro[imidazolidine-4,3'-[3H]indole]-2,2'(1'H), 5-trione.

13. A method of treating heart disease in mammals which comprises administering to a mammal in need thereof a therapeutically effective amount of a compound of the formula (I):

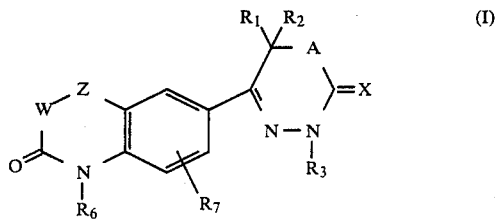

in which, $R_1$ is hydrogen, lower alkyl or $CH_2OR_6$; $R_2$ is hydrogen or lower alkyl; $R_3$ is hydrogen or lower alkyl; each of w and Z, which are different, is —$CR_4R_5$— or —$(CR_xR_y)_n$—, in which, $R_4$ is hydrogen, alkyl of 1 to 3 carbon atoms, alkylthio of 1 to 3 carbon atoms or alkoxy of 1 to 3 carbon atoms; $R_5$ is alkyl of 1 to 3 carbon atoms, alkylthio of 1 to 3 carbon atoms or alkoxy of 1 to 3 carbon atoms; or $R_4$ and $R_5$ together with the carbon atom to which they are attached form a 3- to 6-membered carbocyclic ring, or a 3- to 6-membered heterocyclic ring containing one or two ring oxygen, nitrogen or sulphur atoms; or $R_4$ and $R_5$ together form an oxo or methylene moiety; each of $R_x$ and $R_y$ is hydrogen or alkyl of 1 to 3 carbon atoms; n is zero or 1; $R_6$ is hydrogen, lower alkyl, lower alkylcarbonyl, arylcarbonyl, aralkylcarbonyl, heteroarylcarbonyl, aminocarbonyl, lower alkoxycarbonyl or aryloxycarbonyl wherein the aryl moiety is a carbocyclic aromatic moiety of 6 to 12 carbon atoms, the aralkyl moiety is a carbocyclic aromatic moiety of 6 to 12 carbon atoms linked to an alkylene moiety of 1 to 6 carbon atoms which alkylene moiety is unsubstituted or itself substituted by a carbocyclic aromatic moiety of 6 to 12 carbon atoms, and the heteroaryl moiety is a ring system of 5 to 12 ring atoms having up to 4 heteroatoms selected from the group consisting of oxygen, nitrogen and sulphur; $R_7$ is hydrogen or lower alkyl; X is oxygen or sulphur; and A is sulphur, oxygen or —NH—, in combination with a pharmaceutically acceptable carrier.

14. A method according to claim 13, in which n is zero.

15. A method according to claim 13, in which A is sulphur.

16. A method according to claim 13, in which X is oxygen.

17. A method according to claim 13, in which $R_4$ is methyl and $R_5$ is methyl or thiomethyl, or $R_4$ and $R_5$ together with the carbon atom to which they are attached form a cyclopropyl, cyclopentyl, cyclohexyl, ethylenedithio, propylenedithio or propylenethio moiety.

18. A method according to claim 13, wherein the compound is selected from the group consisting of:

1,3-dihydro-5-(3,6-dihydro-2-oxo-2H-1,3,4-thiadiazin-5-yl)-3-methyl-3-methylthio-2H-indol-2-one;

1,3-dihydro-5-(3,6-dihydro-2-oxo-2H-1,3,4-thiadiazin-5-yl)-3,3-dimethyl-2H-indol-2-one;

1,3-dihydro-5-(3,6-dihydro-6-methyl-2-oxo-2H-1,3,4-thiadiazin-5-yl)-3,3-dimethyl-2H-indol-2-one;

1,3-dihydro-5-(3,6-dihydro-2-oxo-2H-1,3,4-thiadiazin-5-yl)-3-methyl-2H-indol-2-one;

1,3-dihydro-5-(3,6-dihydro-6-methyl-2-oxo-2H- 1,3,4-thiadiazin-5-yl)-3-methyl-3-methylthio-2H-indol-2-one;

5'(3,6-dihydro-6-methyl-2-oxo-2H-1,3,4-thiadiazin-5-yl)-spiro[cyclopentane-1,3'-[3H]-indol]-2'(1'H)-one;

1-acetyl-1,3-dihydro-5-(3,6-dihydro-6-methyl-2-oxo-2H-1,3,4-thiadiazin-5-yl)-3,3-dimethyl-2H-indol-2-one;

1-Acetyl-1,3-dihydro-5-(3,6-dihydro-2-oxo-2H-1,3,4-thiadiazin-5-yl)-3-methyl-2H-indol-2-one 1-Acetyl-1,3-dihydro-5-(3,6-dihydro-2-oxo-2H-1,3,4-thiadiazin-5-yl)-3-methyl-3-methylthio-2H-indol-2-one 1,3-Dihydro-5-(3,6-dihydro-6-methyl-2-oxo-2H-1,3,4-thiadiazin-5-yl)-3-methylthio-2H-indol-2-one 1,3-Dihydro-5-(3,6-dihydro-2-oxo-2H-1,3,4-thiadiazin-5-yl)-3-methylthio-2H-indol-2-one 5-(3,6-Dihydro-6-methyl-2-oxo-2H-1,3,4-thiadiazin-5-yl)1H-indole-2,3-dione 5'-(3,6-Dihydro-6-methyl-2-oxo-2H-1,3,4 thiadiazin-5-yl)-spiro[1,3-dithiolane-2,3 '-[3H]indol]-2(1'H)-one 5'-(3,6-Dihydro-6-methyl-2-oxo-2H-1,3,4-thiadiazin-5-yl)-spiro[1,3-dithiane-2,3'-[3H]indol-2'(1'H)-one
1,3-Dihydro-5-(3,6-dihydro-6-methyl-2-oxo-2H-1,3,4-thiadiazin-5-yl)-3,3-di(methylthio)-2H-indol-2-one
5-(3,6-Dihydro-6-methyl-2-oxo-2H-1,3,4-thiadiazin-5-yl)-spiro[cyclopropane-1,3'-[3H]indol]-2'(1'H)-one
5'-(3,6-Dihydro-6-methyl-2-oxo-2H-1,3,4-thiadiazin-5-yl)-spiro[cyclohexane-1,3'-[3H]indol-2'-(1'H)-one
1,3-Dihydro-5-(3,6-dihydro-6-methyl-2-oxo-2H-1,3,4-thiadiazin-5-yl)-1,3,3-trimethyl-2H-indol-2-one
5'-(3,6-dihydro-3,6-dimethyl-2-oxo-2H-1, 3,4-thiadiazin-5-yl)-1'-methyl-spiro[cyclopentane-1, 3'-[3H]indol]-2'(1'H)-one
5'-(3,6-Dihydro-2-oxo-2H-1,3,4-thiadiazin-5-yl)-spiro[-thiolane-2,3,'-[3H]-indol]-2'(1'H)-one
5'-(3,6-Dihydro-6-methyl-2-oxo-2H-1,3,4-thiadiazin-5-yl)-spiro[thiolane-2,3'-[3H]-indol]-2'(1'H)-one
1-Benzoyl-1,3-dihydro-5-(3,6-dihydro-6-methyl-2-oxo-2H-1,3,4-thiadiazin-5-yl)-3,3-dimethyl-2H-indol-2-one
1,3-Dihydro-5-(3,6-dihydro-6-methyl-2-oxo-2H-1,3,4-thiadiazin-5-yl)-3,3-dimethyl-1-[(4-pyridyl)carbonyl-2H-indol]-2-one
1,3-Dihydro-5-(3,6-dihydro-6-methyl-2-oxo-2H-1,3,4-thiadiazin-5-yl)-3,3-dimethyl-1-[(3-pyridyl)carbonyl]-2H-indol-2-one
1,3-Dihydro-5-(3,6-dihydro-6-methyl-2-oxo-2H-1,3,4-thiadiazin-5-yl)-3,3-dimethyl-1-(4-nitrobenzoyl)-2H-indol-2-one
1,3-Dihydro-5-(3,6-dihydro-6-methyl-2-oxo-2H-1,3,4-thiadiazin-5-yl)-3,3-dimethyl-1-(phenylmethyl carbonyl)-2H-indol-2-one
5'-(3,6-Dihydro-6-methyl-2-oxo-2H-1,3,4-thiadiazin-5-yl1'-[(4pyridyl)carbonyl]-spiro[cyclopentane-1,3'-[3H]-indol]-2'(1'H)-one
1-[2,3-Dihydro-5-(3,6-dihydro-6-methyl-2-oxo-2H-1,3,4-thiadiazin-5-yl)-3,3-dimethyl-2-oxo-1H-indol-1-yl]-2,4-diphenyl-1,3-butanedione
1,3-Dihydro-5-(3,6-dihydro-6-methyl-2-oxo- 2H-1,3,4-thiadiazin-5-yl)-3,3,4-trimethyl-2H-indol- 2-one
1,3-Dihydro-5-(3,6-dihydro-6-methyl-2-oxo-2H-1,3,4-thiadiazin-5-yl)-3,3,6-trimethyl-2H-indol-2-one
1,3-Dihydro-5-(3,6-dihydro-6-methyl-2-oxo-2H-1,3,4-thiadiazin-5-yl)-3,3,7-trimethyl-2H-indol-2-one
1,3-Dihydro-5-(3,6-dihydro-6,6-dimethyl-2-oxo-2H-1,3,4-thiadiazin-5-yl)-3,3-dimethyl-2H-indol-2-one
1,3-Dihydro-5-(3,6-dihydro-6-methyl-2-oxo-2H-1,3,4-thiadiazin-5-yl)-3-hydroxy-3-methyl-2H-indol-2-one
Ethyl 2,3-dihydro-5-(3,6-dihydro-6-methyl-2-oxo-2H-1,3,4-thiadiazin-5-yl)-3,3-dimethyl-2-oxo-1H-indol-1-carboxylate
1,3-Dihydro-5-(1,2,3,6-tetrahydro-6-methyl-2-oxo-1,3,4-triazin-5-yl)-3,3-dimethyl-2H-indol-2-one
1,3-Dihydro-5-(3,6-dihydro-6-methyl-2-oxo-2H-1,3,4-oxadiazin-5-yl)-3,3-dimethyl-2H-indol-2-one
1,3-Dihydro-5-(3,6-dihydro-6-methyl-2-oxo-2H-1,3,4-thiadiazin-5-yl)-1-(3,4-dimethoxybenzoyl)-3,3-dimethyl-2H-indol-2-one
Phenyl 2,3-dihydro-5-(3,6-dihydro-6-methyl-2-oxo-2H-1, 3,4-thiadiazin-5-yl)-3,3-dimethyl-2-oxo-1H-indole-1-carboxylate
3,4-Dihydro-6-(3,6-dihydro-6-methyl-2-oxo-2H-1,3,4-thiadiazin-5-yl)-4,4-dimethyl-2-(1H)-quinolinone
3,4-Dihydro-6-(3,6-dihydro-6-methyl-2-oxo-2H-1,3,4-thiadiazin-5-yl)-3,3-dimethyl-2(1H)-quinolinone
5'-(3,6-Dihydro-6-methyl-2-oxo-2H-1,3,4-thiadiazin-5-yl)-1'[(4nitrophenyl)carbonyl]-spiro[cyclopentane-1,3'-[3H]indol]-2'(1'H)-one
1,3-Dihydro-5-(3,6-dihydro-6-methyl-2-oxo-2H-1,3,4-thiadiazin-5-yl)-3,3-dimethyl-1-[4-aminophenyl)carbonyl-2H-indol-2-one
2,3-Dihydro-5-(3,6-Dihydro-6-methyl-2-oxo-2H-1,3,4-thiadiazin-5-yl)-3,3-dimethyl-2-oxo-1H- indol-1-carboxamide
Ethyl 1,2,3,4-tetrahydro-6-(3,6-dihydro-6-methyl-2-oxo-2H-1,3,4-thiadizain-5-yl)-4,4-dimethyl- 2-oxo-1-quinoline carboxylate and
5'-(3,6-Dihydro-6-methyl-2-oxo-2H-1,3,4-thiadiazin-5-yl)-spiro[imidazolidine-4,3'-[3H]indole]- 2,2'(1'H),5-trione.

19. A method of treating asthmatic conditions in mammals which comprises administering to a mammal in need thereof a therapeutically effective amount of a compound of the formula (I):

$$\text{(I)}$$

in which, $R_1$ is hydrogen, lower alkyl or $CH_2OR_6$; $R_2$ is hydrogen or lower alkyl; $R_3$ is hydrogen or lower alkyl; each of W and Z, which are different, is —$CR_4R_5$— or —$(CR_xR_y)_n$—, in which, $R_4$ is hydrogen, alkyl of 1 to 3 carbon atoms, alkylthio of 1 to 3 carbon atoms or alkoxy of 1 to 3 carbon atoms; $R_5$ is alkyl of 1 to 3 carbon atoms, alkylthio of 1 to 3 carbon atoms or alkoxy of 1 to 3 carbon atoms; or $R_4$ and $R_5$ together with the carbon atom to which they are attached form a 3- to 6-membered carbocyclic ring, or a 3- to 6-membered heterocyclic ring containing one or two ring oxygen, nitrogen or sulphur atoms; or $R_4$ and $R_5$ together form an oxo or methylene moiety; each of $R_x$ and $R_y$ is hydrogen or alkyl of 1 to 3 carbon atoms; n is zero or 1; $R_6$ is hydrogen, lower alkyl, lower alkylcarbonyl, arylcarbonyl, aralkylcarbonyl, heteroarylcarbonyl, aminocarbonyl, lowr alkoxycarbonyl or aryloxycarbonyl wherein the aryl moiety is a carbocyclic aromatic moiety of 6 to 12 carbon atoms, the aralkyl moiety is a carbocyclic aromatic moiety of 6 to 12 carbon atoms linked to an alkylene moiety of 1 to 6 carbon atoms which alkylene moiety is unsubstituted or itself substituted by a carbocyclic aromatic moiety of 6 to 12 carbon atoms, and the heteroaryl moiety is a ring system of 5 to 12 ring atoms having up to 4 heteroatoms selected from the group consisting of oxygen, nitrogen and sulphur; $R_7$ is hydrogen or lower alkyl; X is oxygen or sulphur; and A is sulphur, oxygen or —NH—, in combination with a pharmaceutically acceptable carrier.

20. A method according to claim 19, in which n is zero.

21. A method according to claim 19, in which A is sulphur.

22. A method according to claim 19, in which X is oxygen.

23. A method according to claim 19, in which $R_4$ is methyl and $R_5$ is methyl or thiomethyl, or $R_4$ and $R_5$ together with the carbon atom to which they are attached form a cyclopropyl, cyclopentyl, cyclohexyl, ethylenedithio, propylenedithio or propylenethio moiety.

24. A method according to claim 19, wherein the compound is selected from the group consisting of:

1,3-dihydro-5-(3,6-dihydro-2-oxo-2H-1,3,4-thiadiazin-5-yl)-3-methyl-3-methylthio-2H-indol-2-one;

1,3-dihydro-5-(3,6-dihydro-2-oxo-2H-1,3,4-thiadiazin-5-yl)-3,3-dimethyl-2H-indol-2-one;

1,3-dihydro-5-(3,6-dihydro-6-methyl-2-oxo-2H-1,3,4-thiadiazin-5-yl)-3,3-dimethyl-2H-indol-2-one;

1,3-dihydro-5-(3,6-dihydro-2-oxo-2H-1,3,4-thiadiazin-5-yl)-3-methyl-2H-indol-2-one;

1,3-dihydro-5-(3,6-dihydro-6-methyl-2-oxo-2H-1,3,4-thiadiazin-5-yl)-3-methyl-3-methylthio-2H-indol-2-one;

5'-(3,6-dihydro-6-methyl-2-oxo-2H-1,3,4-thiadiazin-5-yl)-spiro[cyclopentane-1,3'-[3H]-indol]-2'(1'H)-one;

1-acetyl-1,3-dihydro-5-(3,6-dihydro-6-methyl-2-oxo-2H-1,3,4-thiadiazin-5-yl)-3,3-dimethyl-2H-indol-2-one;

1-Acetyl-1,3-dihydro-5-(3,6-dihydro-2-oxo-2H-1,3,4-thiadiazin-5-yl)-3-methyl-2H-indol-2-one 1-Acetyl-1,3-dihydro-5-(3,6-dihydro-2-oxo-2H-1,3,4-thiadiazin-5-yl)-3-methyl-3-methylthio-2H-indol-2-one 1,3-Dihydro-5-(3,6-dihydro-6-methyl-2-oxo-2H-1,3,4-thiadiazin-5-yl)-3-methylthio-2H-indol-2-one 1,3-Dihydro-5-(3,6-dihydro-2-oxo-2H-1,3,4-thiadiazin-5-yl)-3-methylthio-2H-indol-2-one 5-(3,6-Dihydro-6-methyl-2-oxo-2H-1,3,4-thiadiazin-5-yl)1H-indole-2,3-dione 5'-(3,6-Dihydro-6-methyl-2-oxo-2H-1,3,4-thiadiazin-5-yl)-spiro[1,3-dithiolane-2,3'-[3H]indol]-2(1'H)-one 5'-(3,6-Dihydro-6-methyl-2-oxo-,2H-1,3,4-thiadiazin-5-yl)-spiro[1,3-dithiane-2,3'-[3H]indol-2'(1'H)-one 1,3-Dihydro-5-(3,6-dihydro-6-methyl-2-oxo-2H-1,3,4-thiadiazin-5-yl)-3,3-di(methylthio)-2H-indol-2-one 5-(3,6-Dihydro-6-methyl-2-oxo-2H-1,3,4-thiadiazin-5-yl)-spiro[cyclopropane-1,3'-[3H]indol]-2'(1'H)-one 5'-(3,6-Dihydro-6-methyl-2-oxo-2H-1,3,4-thiadiazin-5-yl)-spiro[cyclohexane-1,3'-[3H]indol]-2'-(1'H)-one 1,3-Dihydro-5-(3,6-dihydro-6-methyl-2-oxo-2H-1,3,4-thiadiazin-5-yl)-1,3,3-trimethyl-2H-indol-2-one 5'-(3,6-dihydro-3,6-dimethyl-2-oxo-2H-1,3,4-thiadiazin-5-yl)-1'-methyl-spiro[cyclopentane-1, 3'-[3H]indol]-2'(1'H)-one 5'-(3,6-Dihydro-2-oxo-2H-1,3,4-thiadiazin-5-yl)-spiro[thiolane-2,3'-[3H]-indol]-2'(1'H)-one 5'-(3,6-Dihydro-6-methyl-2-oxo-2H-1,3,4-thiadiazin-5-yl)-spiro[thiolane2,3'-[3H]-indol]-2'(1'H)-one 1-Benzoyl-1,3-dihydro-5-(3,6-dihydro-6-methyl-2-oxo-2H-1,3,4-thiadiazin-5-yl)-3,3-dimethyl-2H-indol-2-one 1,3-Dihydro-5-(3,6-dihydro-6-methyl-2-oxo-2H-1,3,4-thiadiazin-5-yl)-3,3-dimethyl-1-[(4-pyridyl)carbonyl-2H-indol]-2-one 1,3-Dihydro-5-(3,6-dihydro-6-methyl-2-oxo-2H-1,3,4-thiadiazin-5-yl)-3,3-dimethyl-1-[(3-pyridyl)carbonyl]-2H-indol-2-one 1,3-Dihydro-5-(3,6-dihydro-6-methyl-2-oxo-2H-1,3,4-thiadiazin-5-yl)-3,3-dimethyl-1-(4-nitrobenzoyl)-2H-indol-2-one 1,3-Dihydro-5-(3,6-dihydro-6-methyl-2-oxo-2H-1,3,4-thiadiazin-5-yl)-3,3-dimethyl-1-(phenylmethyl carbonyl)-2H-indol-2-one 5'-(3,6-Dihydro-6-methyl-2-oxo-2H-1,3,4-thiadiazin-5-yl1'-[(4pyridyl)carbonyl]-spiro[cyclopetane-1,3'-[3H]-indol-2'(1'H)-one 1-[2,3-Dihydro-5-(3,6-dihydro-6-methyl-2-oxo-2H-1,3,4-thiadiazin-5-yl)-3,3-dimethyl-2-oxo-1H-indol-1-yl]-2,4-diphenyl-1,3 butanedione 1,3-Dihydro-5-(3,6-dihydro-6-methyl-2-oxo-2H-1,3,4-thiadiazin-5-yl)-3,3,4-trimethyl-2H-indol-2-one 1,3-Dihydro-5-(3,6-dihydro-6-methyl-2-oxo-2H-1,3,4-thiadiazin-5-yl)-3,3,6-trimethyl-2H-indol-2-one 1,3-Dihydro-5-(3,6-dihydro-6-methyl-2-oxo-2H-1,3,4-thiadiazin-5-yl)-3,3,7-trimethyl-2H-indol-2-one 1,3-Dihydro-5-(3,6-dihydro-6,6-dimethyl-2-oxo-2H-1,3,4-thiadiazin-5-yl)-3,3-dimethyl-2H-indol-2-one 1,3-Dihydro-5-(3,6-dihydro-6-methyl-2-oxo-2H-1,3,4-thiadiazin-5-yl)-3-hydroxy-3-methyl-2H-indol-2-one Ethyl 2,3-dihydro-5-(3,6-dihydro-6-methyl-2-oxo-2H-1,3,4-thiadiazin-5-yl)-3,3-dimethyl-2-oxo-1H-indol-1-carboxylate 1,3-Dihydro-5-(1,2,3,6-tetrahydro-6-methyl-2-oxo-1,3,4-triazin-5-yl)-3,3-dimethyl-2H-indol-2-one 1,3-Dihydro-5-(3,6-dihydro-6-methyl-2-oxo-2H-1,3,4-oxadiazin-5-yl)-3,3-dimethyl-2H-indol-2-one 1,3-Dihydro-5-(3,6-dihydro-6-methyl-2-oxo-2H-1,3,4-thiadiazin-5-yl)-1-(3,4-dimethoxybenzoyl)-3,3-dimethyl-2H-indol-2-one Phenyl 2,3-dihydro-5-(3,6-dihydro-6-methyl-2-oxo-2H-1,3,4-thiadiazin-5-yl)-3,3-dimethyl-2-oxo-1H-indole-1-carboxylate 3,4-Dihydro-6-(3,6-dihydro-6-methyl-2-oxo-2H-1,3,4-thiadiazin-5-yl)-4,4-dimethyl-2-(1H)-quinolinone 3,4-Dihydro-6-(3,6-dihydro-6-methyl-2-oxo-2H-1,3,4-thiadiazin-5-yl)-3,3-dimethyl-2(1H)-quinolinone 5'-(3,6-Dihydro-6-methyl-2-oxo-2H-1,3,4-thiadiazin-5-yl)-1'[(4-nitrophenyl)carbonyl]-spiro[cyclopentane-1,3'-[3H]indol]-2'(1'H)-one 1,3-Dihydro-5-(3,6-dihydro-6-methyl-2-oxo-2H-1,3,4-thiadiazin-5-yl)-3,3-dimethyl-1-[4-aminophenyl)carbonyl]-2H-indol-2-one 2,3-Dihydro-5-(3,6-dihydro-6-methyl-2-oxo-2H-1,3,4-thiadiazin-5-yl)-3,3-dimethyl-2-oxo-1H-indole-1-carboxamide Ethyl 1,2,3,4-tetrahydro-6-(3,6-dihydro-6-methyl-2-oxo-2H-1,3,4-thiadiazin-5-yl)-4,4-dimethyl-2-oxo-1-quinoline carboxylate and 5'-(3,6-Dihydro-6-methyl-2-oxo-2H-,1,3,4-thiadiazin-5-yl)-spiro[imidazolidine-4,3'-[3H]indole]-2,2'-(1'H),5-trione.

* * * * *